(12) United States Patent
Brooke et al.

(10) Patent No.: US 12,167,876 B2
(45) Date of Patent: Dec. 17, 2024

(54) BONE FASTENER TOWER ASSEMBLY FOR SPINAL SURGERY

(71) Applicant: Zimmer Biomet Spine, Inc., Westminster, CO (US)

(72) Inventors: Douglas Brooke, Golden, CO (US); Heidi Farmer, Superior, CO (US); Guillaume Quetier, Lakewood, CO (US); James Vincent Eaton, Denver, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 0 days.

(21) Appl. No.: 17/886,833

(22) Filed: Aug. 12, 2022

(65) Prior Publication Data
US 2023/0049503 A1  Feb. 16, 2023

Related U.S. Application Data

(60) Provisional application No. 63/233,046, filed on Aug. 13, 2021.

(51) Int. Cl.
*A61B 17/70* (2006.01)
(52) U.S. Cl.
CPC ........ *A61B 17/7086* (2013.01); *A61B 17/708* (2013.01); *A61B 17/7085* (2013.01); *A61B 17/7052* (2013.01)
(58) Field of Classification Search
CPC .................. A61B 17/7085; A61B 17/7086
See application file for complete search history.

(56) References Cited

U.S. PATENT DOCUMENTS

| | | |
|---|---|---|
| 5,941,885 A | 8/1999 | Jackson |
| 2010/0063552 A1 | 3/2010 | Chin |
| 2011/0184469 A1 | 7/2011 | Ballard |
| 2013/0090697 A1 | 4/2013 | George |
| 2013/0110124 A1* | 5/2013 | Gleason ............. A61B 17/7076 606/104 |

(Continued)

FOREIGN PATENT DOCUMENTS

EP  3539491  9/2019

OTHER PUBLICATIONS

Official Action (with English machine translation) for French Patent Application No. FR2208266, dated Nov. 7, 2022 6 pages.

(Continued)

*Primary Examiner* — Julianna N Harvey
(74) *Attorney, Agent, or Firm* — Sheridan Ross P.C.

(57) ABSTRACT

Systems and methods of operating a tower extender in conjunction with a bone anchor housing can comprise positioning a plurality of deflectable members of a distal end of the tower extender proximate the bone anchor housing, pushing the distal end of the tower extender into engagement with the bone anchor housing to flex the plurality of deflectable members around the bone anchor housing to attach the tower extender relative to the bone anchor housing, rotating a knob to lock the plurality of deflectable members from deflecting away from the bone anchor housing, performing a portion of a surgical procedure with the tower extender, rotating the knob to deflect the plurality of deflectable members away from the bone anchor housing and puling the tower extender away from the bone anchor housing.

18 Claims, 33 Drawing Sheets

(56) References Cited

U.S. PATENT DOCUMENTS

| | | | |
|---|---|---|---|
| 2013/0245705 A1* | 9/2013 | McBride | A61B 17/708 606/86 R |
| 2015/0105831 A1 | 4/2015 | Yim | |
| 2015/0351810 A1 | 12/2015 | Lindner | |
| 2015/0359571 A1* | 12/2015 | Biedermann | A61B 17/708 606/86 R |
| 2016/0331420 A1* | 11/2016 | Dandanopoulos | A61B 17/708 |
| 2018/0214190 A1 | 8/2018 | Erramilli | |
| 2019/0142471 A1* | 5/2019 | Lindner | A61B 17/7037 606/266 |
| 2019/0365425 A1 | 12/2019 | Casey | |
| 2020/0187987 A1 | 6/2020 | Parker et al. | |
| 2020/0188034 A1 | 6/2020 | Lequette | |
| 2020/0305932 A1* | 10/2020 | Park | A61B 17/7091 |
| 2023/0052647 A1 | 2/2023 | Brooke et al. | |

OTHER PUBLICATIONS

Official Action for Great Britain Patent Application No. GB 2212049.7, dated Jan. 26, 2023 6 pages.

Notice of Allowance for Great Britain Patent Application No. GB 2212049.7, dated Sep. 25, 2023 2 pages.

Official Action for U.S. Appl. No. 17/886,851, dated Dec. 20, 2023 13 pages.

Notice of Allowance for U.S. Appl. No. 17/886,851, dated Apr. 4, 2024 9 pages.

* cited by examiner

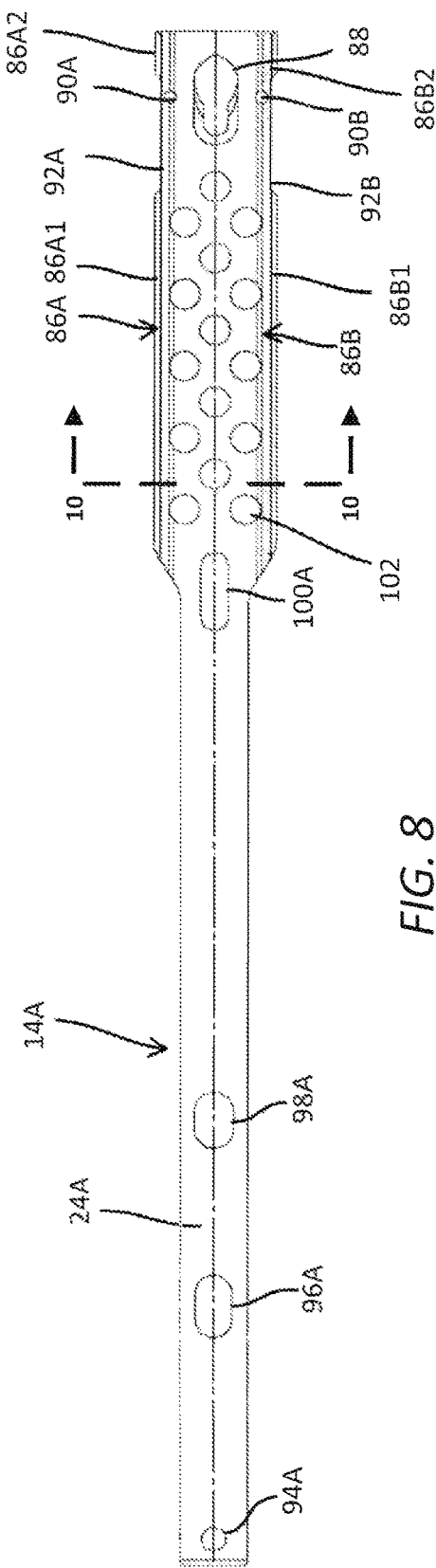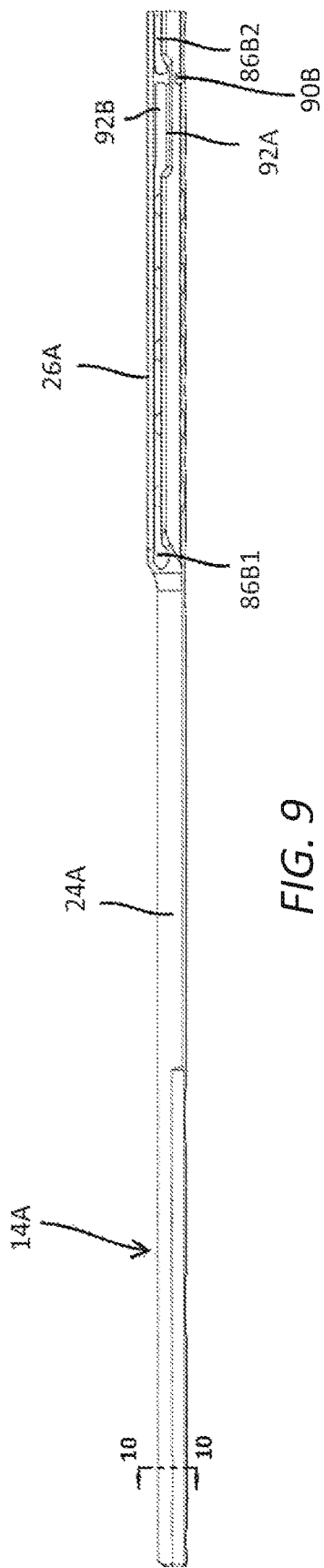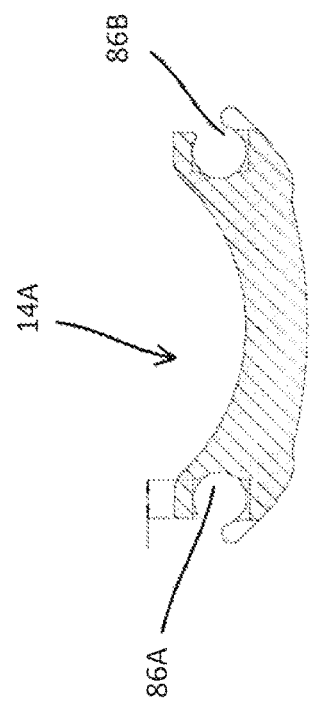

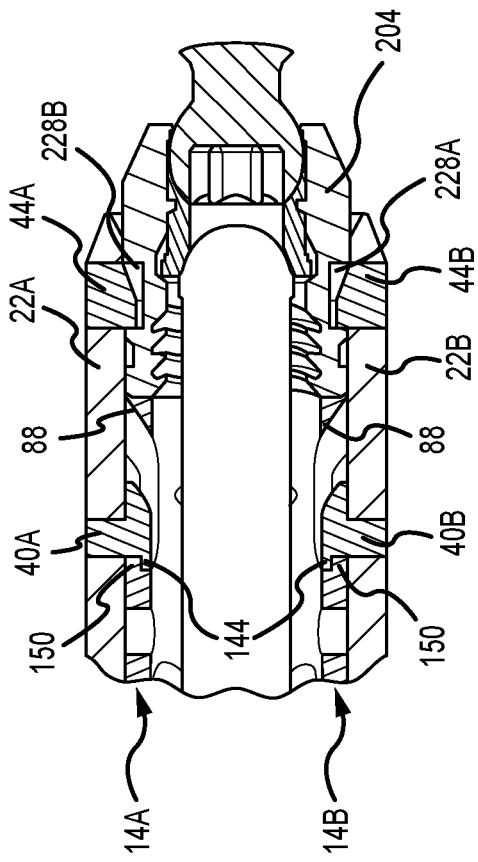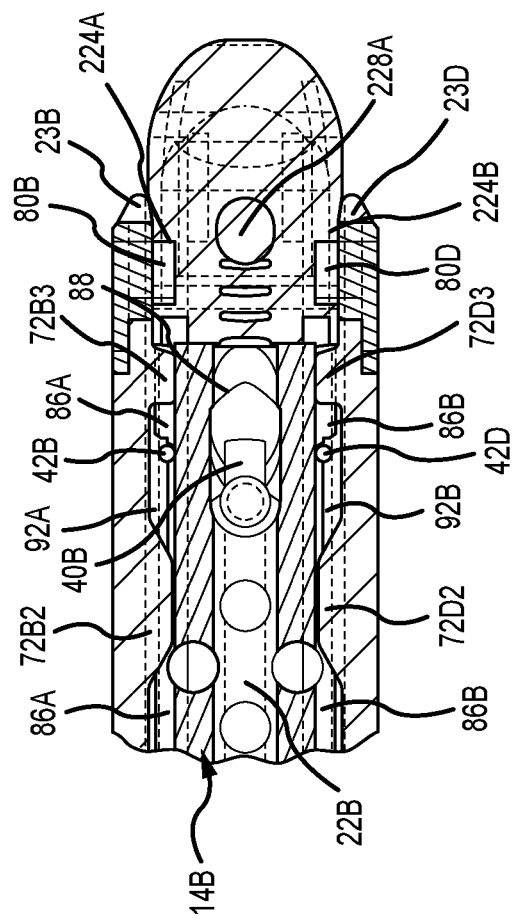

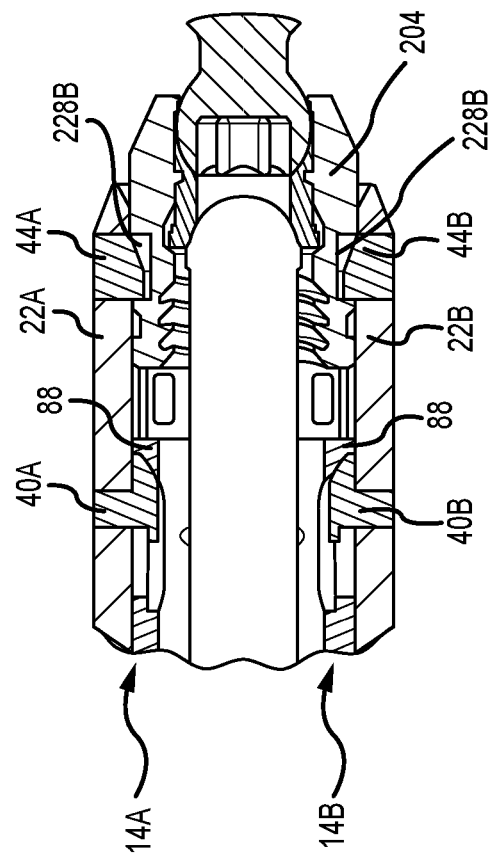
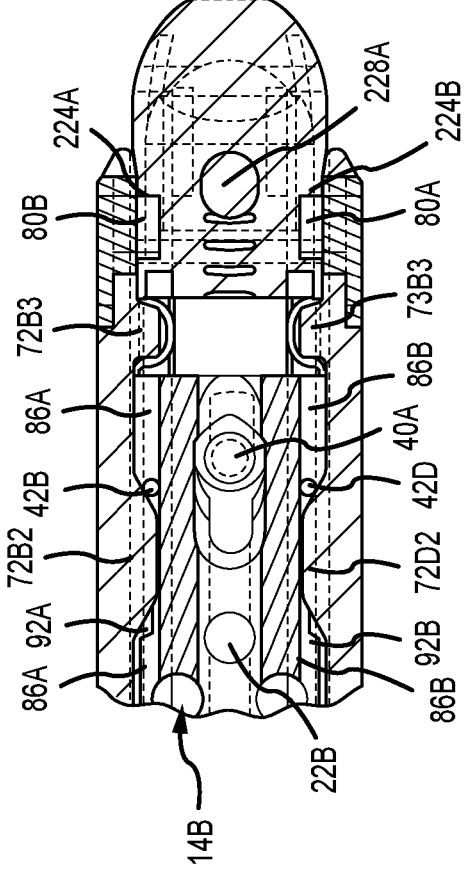
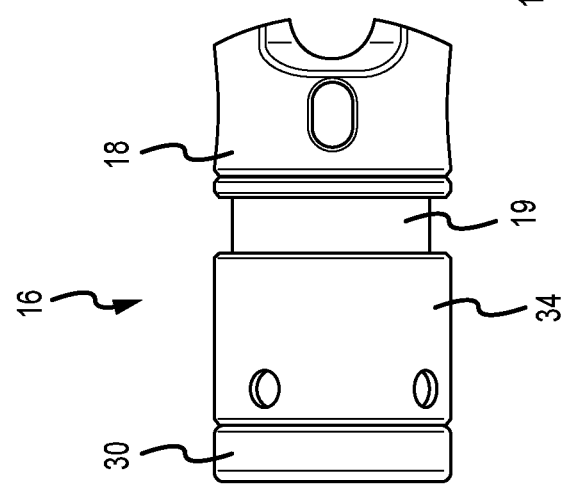

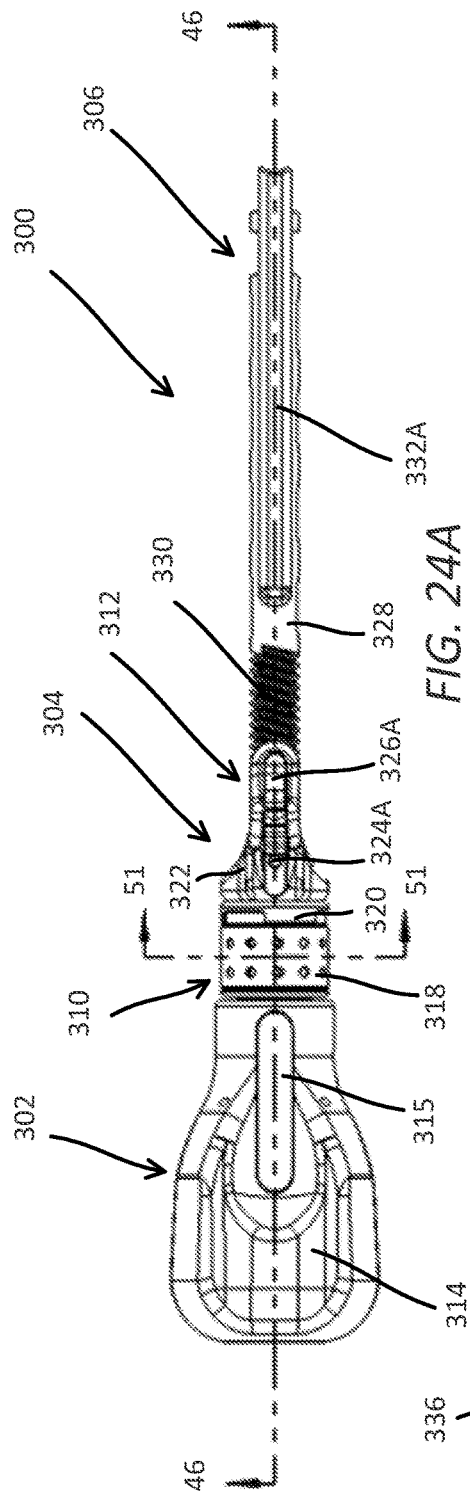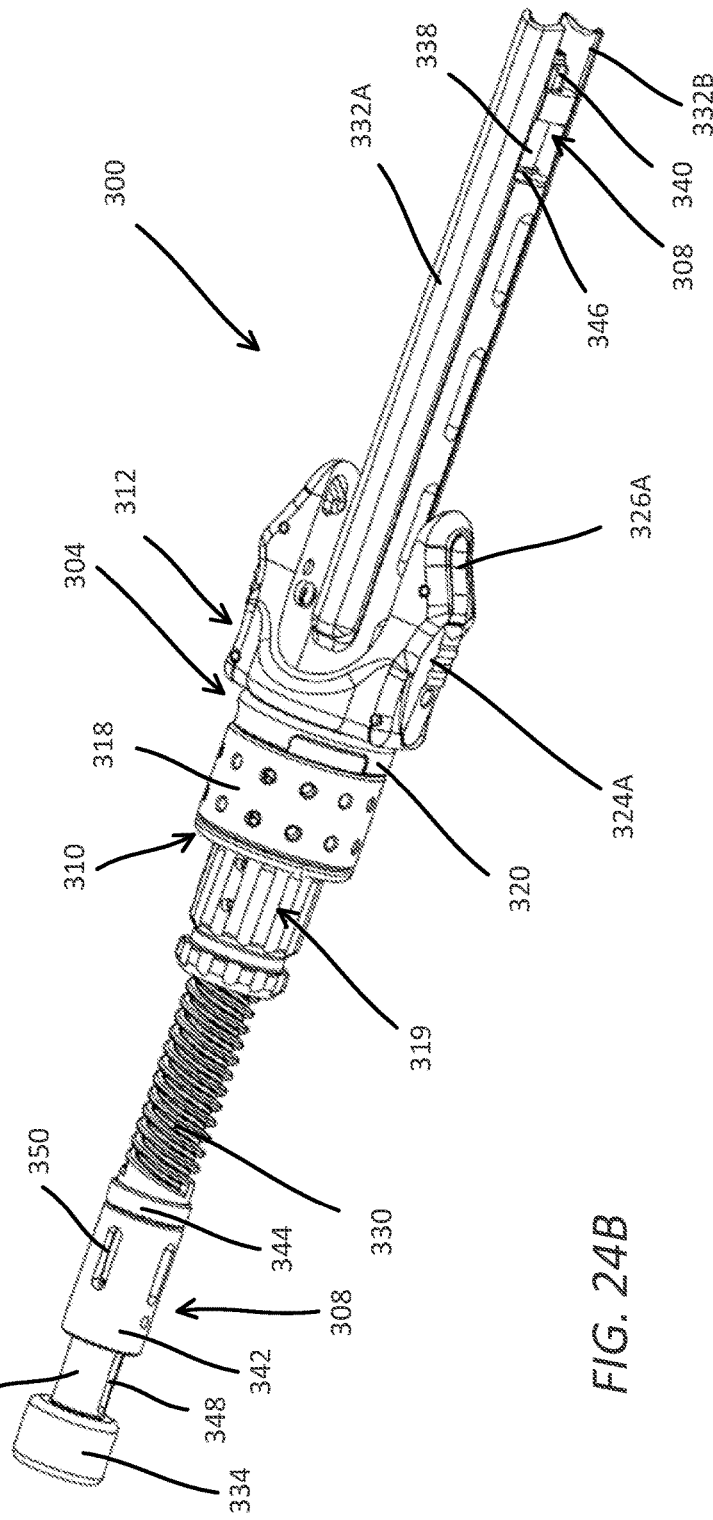

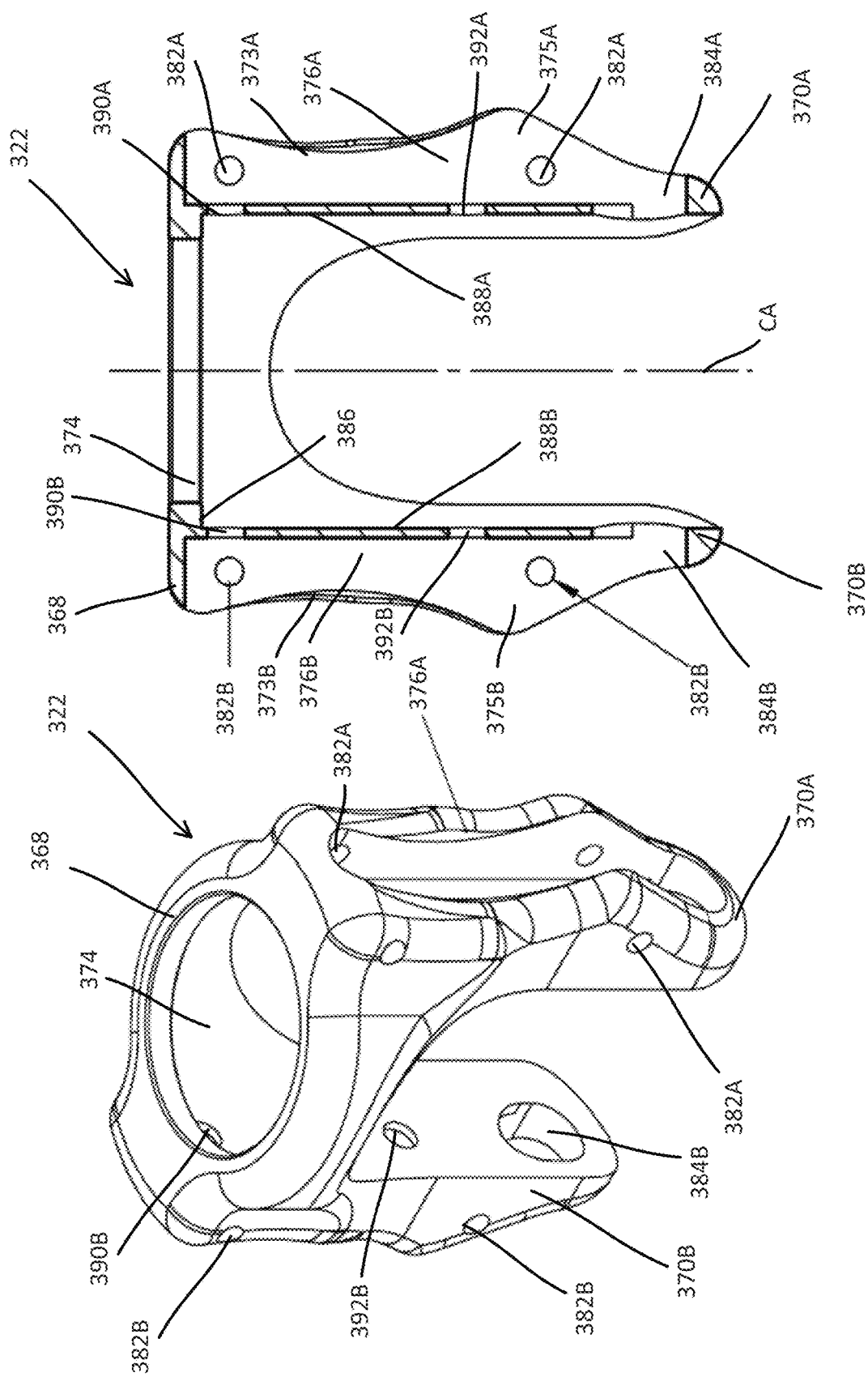

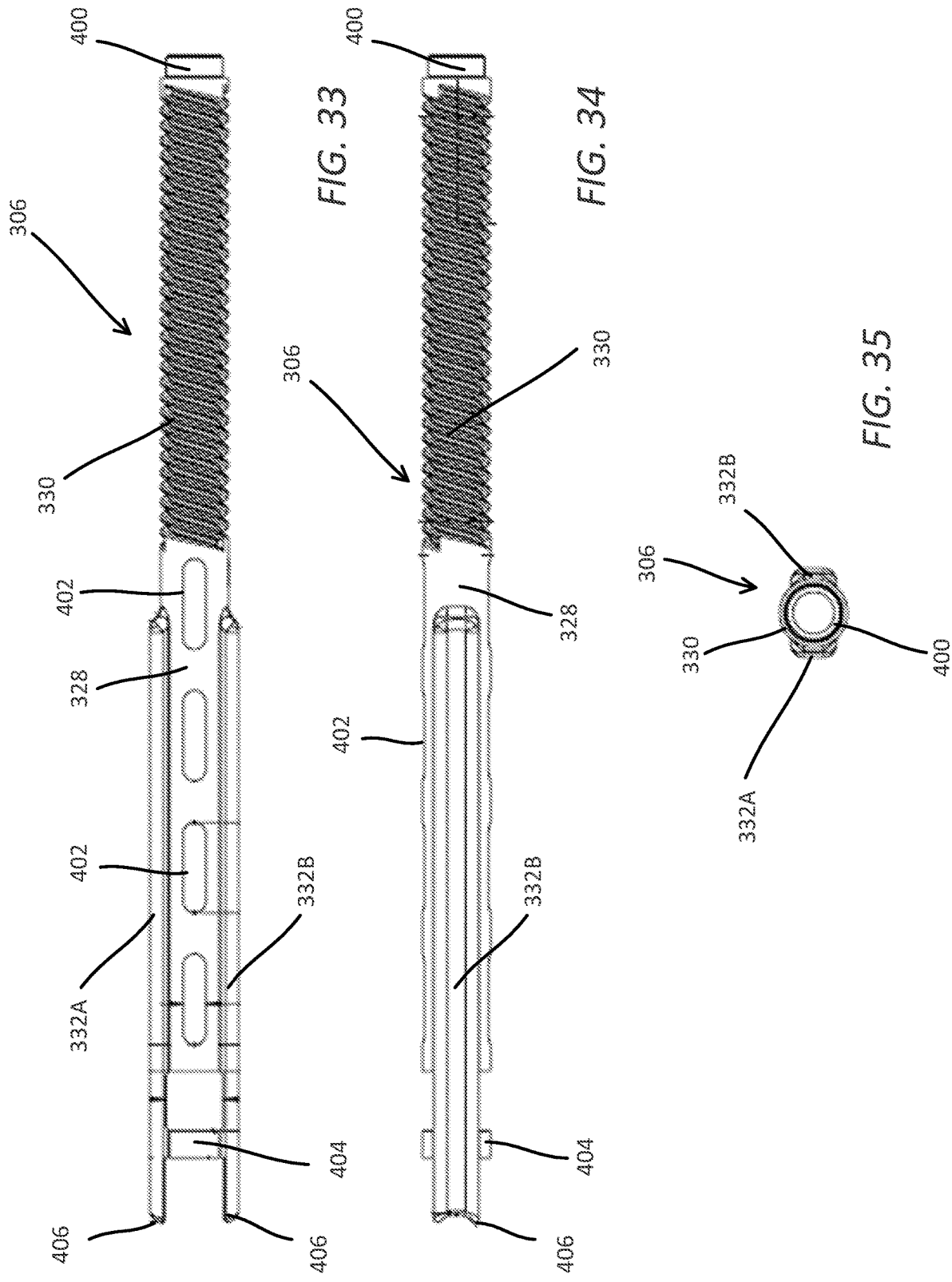

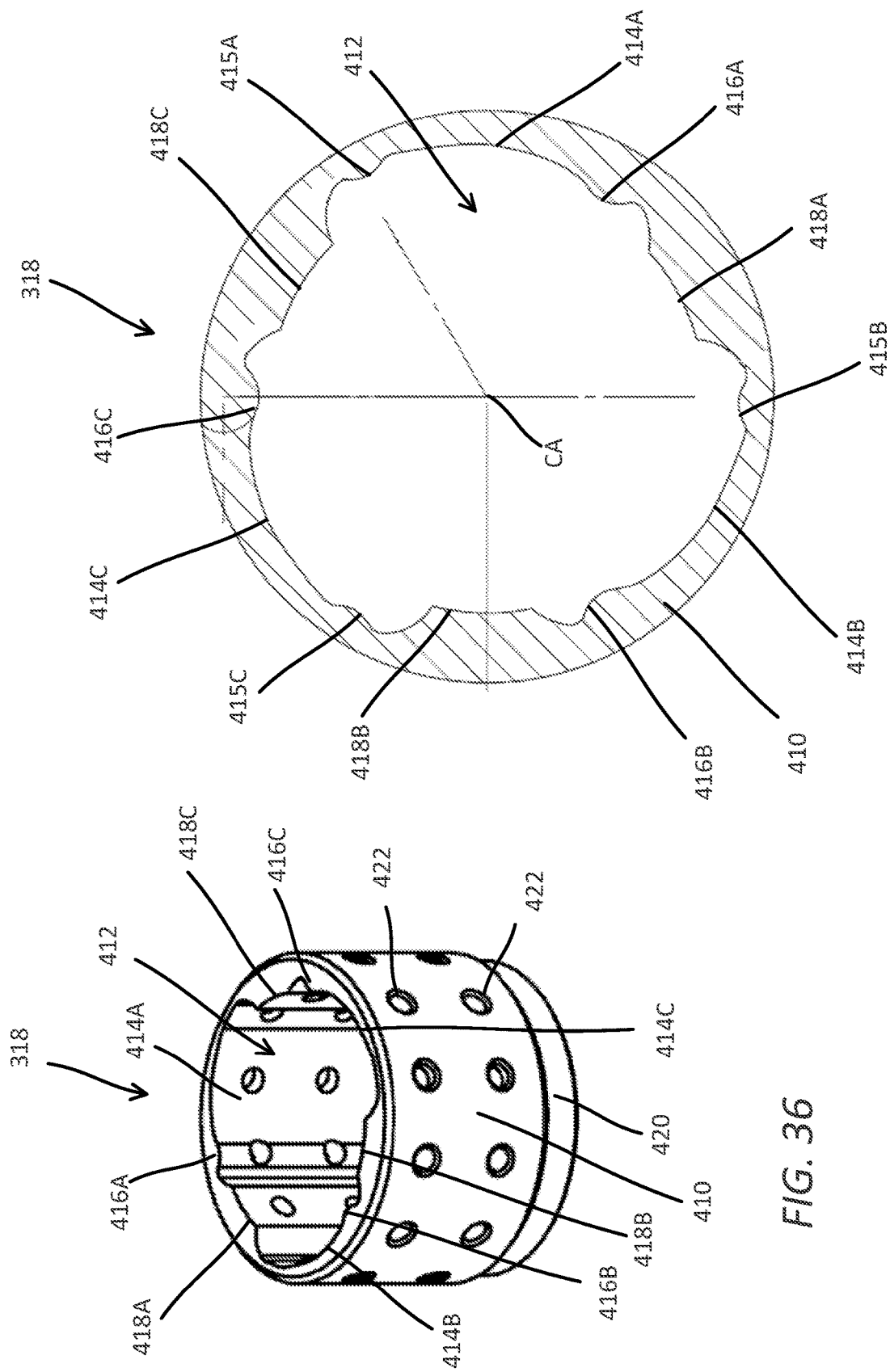

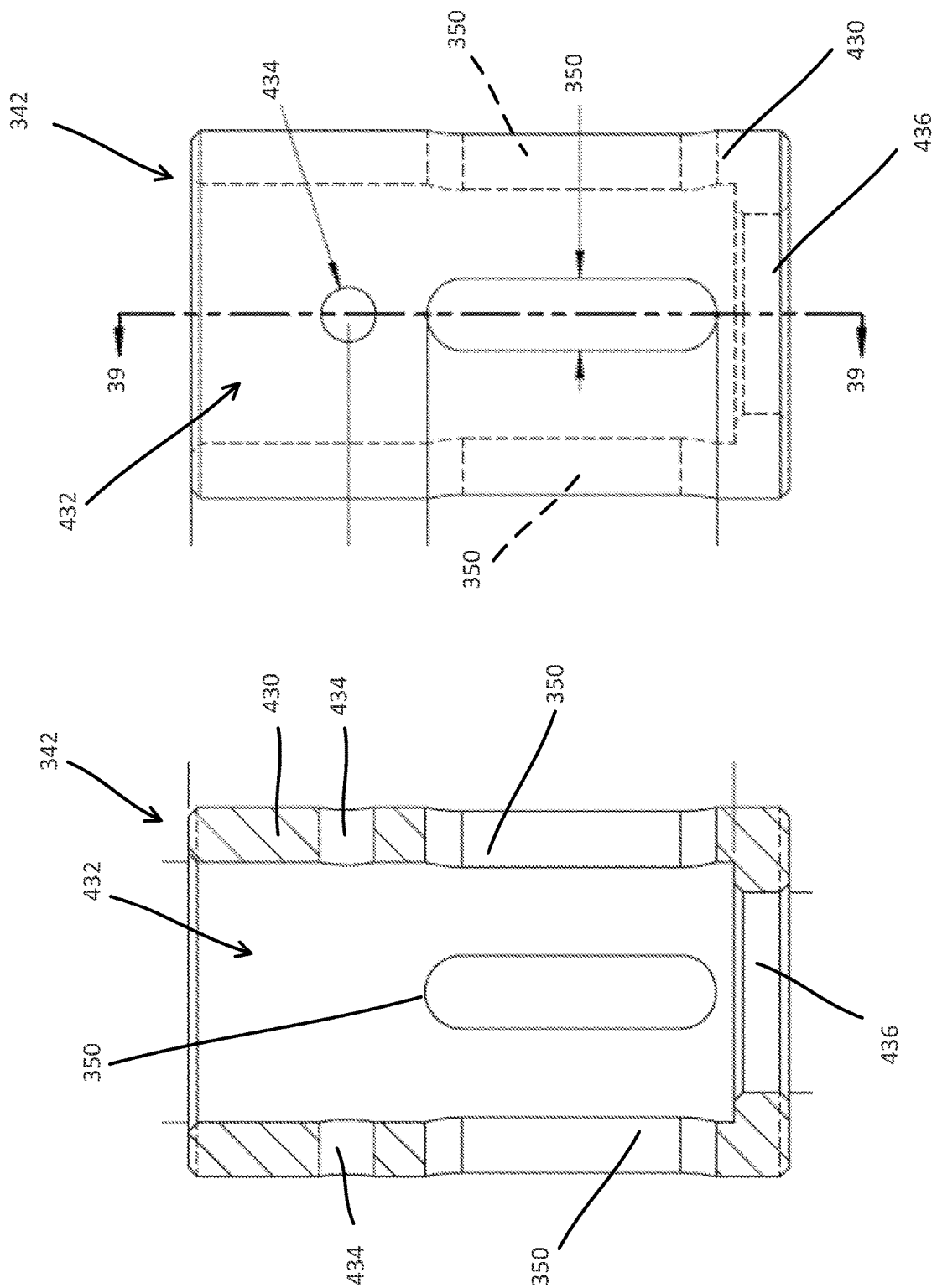

BONE FASTENER TOWER ASSEMBLY FOR SPINAL SURGERY

CROSS REFERENCE TO RELATED APPLICATIONS

This application claims the benefit of U.S. Provisional Application No. 63/233,046, filed on Aug. 13, 2021, which application is incorporated herein by reference in its entirety.

TECHNICAL FIELD

This document pertains generally, but not by way of limitation, to devices and methods for surgical procedures involving bones, such as those involving the use of bone fasteners. More specifically, but not by way of limitation, the present application relates to extension devices for providing sub-dermal access to implanted pedicle screws of the spinal column.

BACKGROUND

Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a spinal column to one or more vertebrae to stabilize a region of the spine. Surgical procedures for the spinal column have become less invasive by the use of specialized instrumentation and implants that utilize extension devices to provide sub-dermal access through portals without having to make an access portal extending along the entire region of the spine. However, some of the instruments used in minimally invasive spinal procedures can be difficult for the surgeon to use intraoperatively or provide unsatisfactory performance.

SUMMARY

Problems to be solved in performing surgical procedures on the spine with extension devices or towers include balancing the ability to attach and detach the extender from a pedicle screw housing, the ability of the extender to stay attached to the pedicle screw housing while performing a procedure, and the ability to perform the desired procedure using the extender. For example, increasing the capability of the extender to stay attached to a pedicle screw can make operation of the extender more difficult. An example tower is described in Pub. No. US 2020/0187987A1 to Parker et al. titled "Split Tower for a Bone Anchor" and is herein incorporated by reference.

The present subject matter can provide a solution to these and other problems, such as by providing a bone anchor extender for use with pedicle screws and other anchor types that can be easily operated, robustly attached to a pedicle screw housing, and allow for desired interaction with other instruments. In examples, the present application provides tower extenders that can include a plurality of pairs of deflectable members that attach to a bone anchor housing at different circumferential locations. A control knob can be set to allow the deflectable members to freely deflect, to lock the deflectable members to prevent deflection and to push the deflectable members radially outward.

In at least one example, an extender tower that is configured to couple to a bone anchor can comprise an outer tower body extending along a longitudinal axis from a proximal portion to a distal portion, a cap, a first inner slide and a second inner slide. The tower body can comprise first and second deflectable arms at the distal portion configured to engage with a housing of a bone anchor, first and second ramp-locks located on the first and second deflectable arms, respectively, and a threaded portion located at the proximal portion. The cap can be configured to engage the threaded portion. The first inner slide can comprise a first coupling portion configured to engage the cap and a first window configured to engage the first ramp-lock. The second inner slide can comprise a second coupling portion configured to engage the cap and a second window configured to engage the second ramp-lock. The cap can be rotated to move the first and second inner slides to engage the first and second ramp-locks to push the first and second deflectable arms outward and move the first and second inner slides to engage the first and second ramp-locks to prevent outward movement of the first and second deflectable arms.

In another example, an extender tower for a bone anchor can comprise an outer tower body extending along a longitudinal axis, a slide arrangement and a cap. The tower body can comprise first and second deflectable arms disposed in an opposing arrangement in a first radial direction and first and second deflectable prongs disposed in an opposing arrangement in a second radial direction. The slide arrangement can be configured to slide within the outer tower body to engage the first and second deflectable arms and the first and second deflectable prongs. The cap can be connected to the slide arrangement and configured to move axially relative to the outer tower body to move the slide arrangement. The slide engagement can be configured to engage the first and second deflectable arms and the first and second deflectable prongs in different axial positions including a first axial position configured to radially interlock the slide arrangement with the first and second deflectable arms and the first and second deflectable prongs, a second axial position configured to allow the first and second deflectable arms and the first and second deflectable prongs to freely deflect, and a third axial position configured to push the first and second deflectable arms and the first and second deflectable prongs radially outward.

In other examples, a method of operating a tower extender in conjunction with a bone anchor housing can comprise positioning a plurality of deflectable members of a distal end of the tower extender proximate the bone anchor housing, pushing the distal end of the tower extender into engagement with the bone anchor housing to flex the plurality of deflectable members around the bone anchor housing to attach the tower extender relative to the bone anchor housing, rotating a knob to lock the plurality of deflectable members from deflecting away from the bone anchor housing, performing a portion of a surgical procedure with the tower extender, rotating the knob to deflect the plurality of deflectable members away from the bone anchor housing and puling the tower extender away from the bone anchor housing.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 8 is a first side view of an inner slide showing slide slots, a locking window and pin holes according to at least one embodiment of the present disclosure.

FIG. 9 is a second side view of the inner slide of FIG. 8 showing the side slots according to at least one embodiment of the present disclosure.

FIG. 10 is a cross-sectional view of the inner slide of FIGS. 8 and 9 showing cross-sectional profiles of the slide slots according to at least one embodiment of the present disclosure.

FIG. 19A is a side view of the cap assembly of FIG. 1 showing the cap in a fully advanced position to provide locking functionality with a pedicle screw housing according to at least one embodiment of the present disclosure.

FIG. 19B is cross-sectional view of the distal end of the tower of FIG. 1 showing arm ramps of deflectable arms locked with windows of inner slides and retainers of the deflectable arms engaged with a bone anchor housing according to at least one embodiment of the present disclosure.

FIG. 19C is side view of the distal end of the tower of FIG. 1 showing rail segments of deflectable prongs engaged with slots of an inner slide and bone anchor retainers of deflectable prongs engaged with the bone anchor housing according to at least one embodiment of the present disclosure.

FIG. 20A is a side view of the cap assembly of FIG. 1 showing the cap in a partially retracted position to provide attaching functionality with a pedicle screw housing according to at least one embodiment of the present disclosure.

FIG. 20B is cross-sectional view of the distal end of the tower of FIG. 1 showing arm ramps of deflectable arms positioned within windows of inner slides and retainers of the deflectable arms engaged with a bone anchor housing according to at least one embodiment of the present disclosure.

FIG. 20C is side view of the distal end of the tower of FIG. 1 showing rail segments of deflectable prongs disengaged with slots of an inner slide and bone anchor retainers of deflectable prongs engaged with the bone anchor housing according to at least one embodiment of the present disclosure.

FIG. 24A is a side view of a reducer for a pedicle screw tower of the present disclosure comprising a palm handle, a reducer assembly, a reducing shaft and a driver according to at least one embodiment of the present disclosure.

FIG. 24B is a perspective view of the reducer of FIG. 24A with the palm handle removed according to at least one embodiment of the present disclosure.

FIG. 29 is a perspective view of a reducer body of the reducer assembly of FIG. 28 according to at least one embodiment of the present disclosure.

FIG. 30 is a cross-sectional view of the reducer body of FIG. 29 according to at least one embodiment of the present disclosure.

FIG. 33 is a first side view of the reducing shaft of FIGS. 24-26 according to at least one embodiment of the present disclosure.

FIG. 34 is a second side view of the reducing shaft of FIGS. 24-26 according to at least one embodiment of the present disclosure.

FIG. 35 is an end view of the reducing shaft of FIGS. 24-26 according to at least one embodiment of the present disclosure.

FIG. 36 is a perspective view of a clutch knob of the reducer assembly of FIG. 27 according to at least one embodiment of the present disclosure.

FIG. 37 is a cross-sectional view of the clutch knob of FIG. 36 according to at least one embodiment of the present disclosure.

FIG. 38 is a side view of a plunger for a closure top starter of the driver of FIG. 26 according to at least one embodiment of the present disclosure.

FIG. 39 is a cross-sectional view of the plunger of FIG. 38 according to at least one embodiment of the present disclosure.

Figure 1:
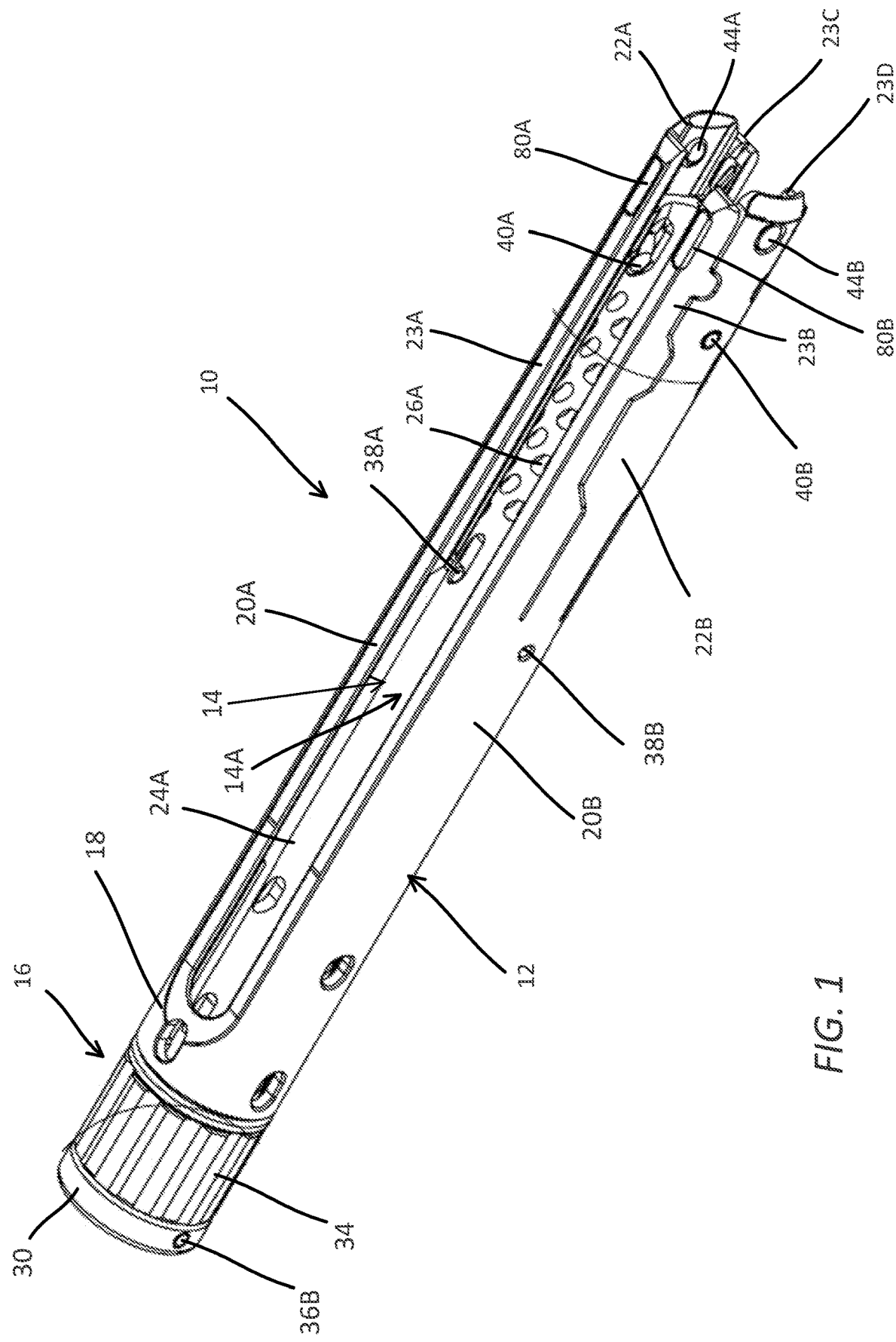
FIG. 1 is a perspective view of a bone anchor tower showing a tower body, an inner slide and a cap assembly according to at least one embodiment of the present disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

The systems and devices described below provide for a pedicle screw tower capable of attaching axially to, for example, a pedicle screw without rotational motion between the pedicle screw tower and the pedicle screw. In other words, the pedicle screw tower may be pushed onto the pedicle screw to thereby releasably attach the pedicle screw tower to the pedicle screw. Additionally, the pedicle screw tower can attach radially around the pedicle screw. Further, the pedicle screw tower may be moved between a first position to lock onto a pedicle screw housing, a second position to allow deflectable arms deflectable prongs of the tower to slip onto a pedicle screw housing by deflecting, and a third position to push the deflectable arms and the deflectable prongs outward to release a pedicle screw housing via a knob.

The systems and devices described below also provide for a reducer in which a load force can be carried by a reducing shaft of the reducer rather than the closure top. The reducer may include a clutch to help center the reducing shaft and also allow the reducing shaft to move between different positions.

Figure 2:
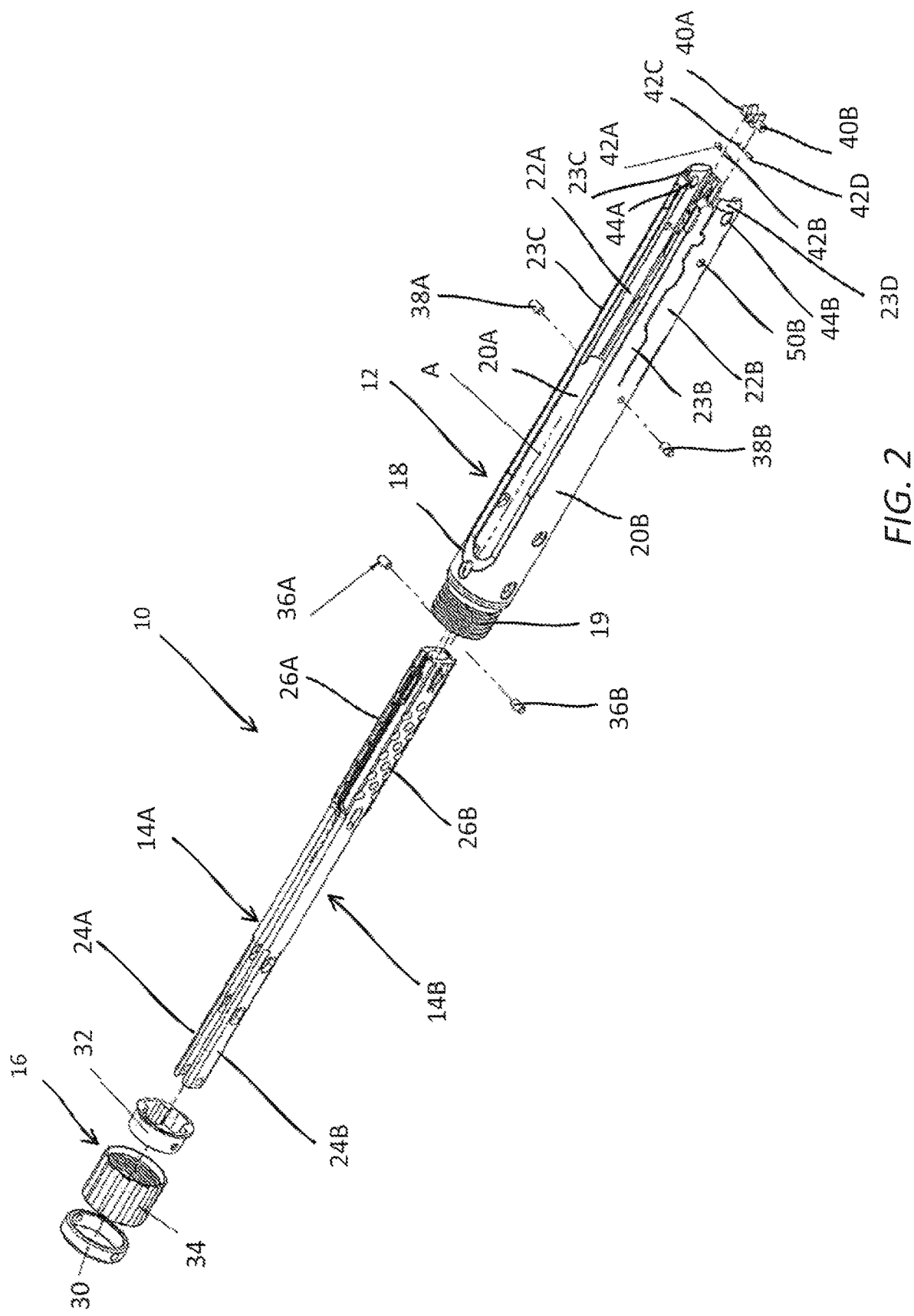
FIG. 2 is an exploded perspective view of the bone anchor tower of FIG. 1 showing a tower body, a pair of inner slides and a cap assembly according to at least one embodiment of the present disclosure.

Turning first to FIG. 1, a perspective view of a pedicle screw tower 10 is shown. The pedicle screw tower 10 includes a tower body 12, one or more inner slides 14 (visible in FIG. 2) and a cap assembly 16. The one or more inner slides 14 may comprise two inner slides 14A and 14B as illustrated, though in other embodiments the one or more inner slides 14 may comprise any number of slides. FIG. 2 is an exploded perspective view of the pedicle screw tower 10 of FIG. 1. FIGS. 1 and 2 are discussed concurrently.

The tower body 12 can comprise a proximal portion 18, a threaded end 19, one or more extenders such as a first extender 20A and a second extender 20B, one or more deflectable arms such as a first deflectable arm 22A and a second deflectable arm 22B, and one or more deflectable prongs 23 such as deflectable prongs 23A-23D. It will be appreciated that in other embodiments the one or more extenders may comprise any number of extenders, the one or more deflectable arms may comprise any number of deflectable arms, and the one or more deflectable prongs may comprise any number of deflectable prongs. The inner slide 14A can comprise a coupling portion 24A and an actuation portion 26A and the inner slide 14B can comprise a coupling portion 24B and an actuation portion 26B. The cap assembly 16 can comprise an outer ring 30, an inner ring 32, and a cap 34. The pedicle screw tower 10 can further comprise one or more cap pins comprising cap pins 36A and 36B, one or more slide pins comprising slide pins 38A and 38B, one or more arm ramps comprising arm ramps 40A and 40B, one or more prong pins comprising prong pins 42A-42D and one or more pedicle screw retainers comprising pedicle screw retainers 44A and 44B. It will be appreciated that in other embodiments the one or more cap pins may comprise any number of cap pins, the one or more arm ramps may comprise any number of arm ramps, the one or more prong pins may comprise any number of prong pins, and the one or more pedicle screw retainers may comprise any number of pedicle screw retainers.

The cap 34 can be rotated to push and pull the inner slides 14A and 14B along the first extender 20A and the second extender 20B, respectively. The inner slides 14A and 14B can engage with the arm ramps 40A and 40B mounted to the deflectable arms 22A and 22B to cause the deflectable arms 22A and 22B to splay outward to release engagement with a housing 204 of a pedicle screw 200 (shown in FIG. 23). Likewise, the prong pins 42A-42D can be assembled with the inner slides 14A and 14B to engage with protrusions (e.g., one or more slide rails comprising slide rails 72A-72D) of the deflectable prongs 23A-23D to cause the deflectable prongs 23A-23D to splay outward to release engagement with the housing 204 of the pedicle screw 200 (shown in FIG. 23). The prong pins 42A-42D can thus comprise actuation features. Additionally, as discussed in greater detail below, the inner slides 14A and 14B can lock with the deflectable arms 22A and 22B and the deflectable prongs 23A-23D to prevent outward deflection.

The knob 34 can therefore be rotated to a first position (shown in FIGS. 19A-19C) to lock a tower 10 onto a pedicle screw housing, a second position (shown in FIGS. 20A-20C) to allow the deflectable arms 22A and 22B and the deflectable prongs 23A-23D to slip onto a pedicle screw housing by deflecting, and a third position (shown in FIGS. 21A-21C) to push the deflectable arms 22A and 22B and the deflectable prongs 23A-23D outward to release a pedicle screw housing.

Figure 3:
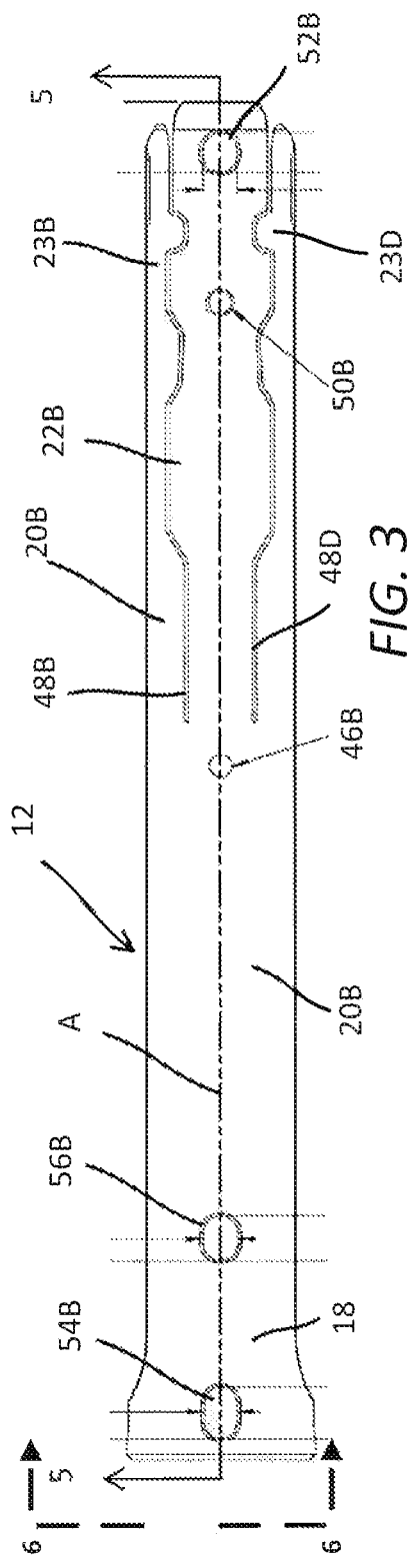
FIG. 3 is a first side view of the tower body of FIGS. 1 and 2 showing a deflectable arm in the tower body according to at least one embodiment of the present disclosure.

Turning to FIG. 3, a side view of the tower body 12 showing a deflectable arm 22B within a second extender 20B is shown. In particular, the deflectable arm 22B is shown positioned between the deflectable prongs 23B and 23D. The tower body 12 can comprise an end portion 18 at a proximal end. The end portion 18 can comprise a ring or other annular structure from which the first extender 20A and the second extender 20B can extend in a distal direction.

The second extender 20B can include a pin hole 46B configured to receive the pin 38B (visible in FIG. 2). The second deflectable arm 22B can be formed from a portion of second extender 20B via one or more break lines comprising break lines 48B and 48D. The second deflectable arm 22B can include a mounting bore 50B for the arm ramp 40B (visible in FIG. 2) and a coupler bore 52B for receiving the retainer 44B (visible in FIG. 2).

The first extender 20A can include a pin hole 46A configured to the receive pin 38A (visible FIG. 2). The first deflectable arm 22A can be formed from a portion of the first extender 20A via the one or more break lines comprising break lines 48A and 48C. The first deflectable arm 22A can include a mounting bore 50A for the arm ramp 40A (visible in FIG. 2) and a coupler bore 52A for receiving the retainer 44A (visible in FIG. 2).

The tower body 12 can additionally include one or more ports comprising ports 54B and 60B, as well as ports 54A and 60A (visible in FIG. 4), configured to receive mating components from a reducer or another component. It will be appreciated that in other embodiments the one or more ports may comprise any number of ports.

It will be appreciated that the first extender 20A and the second extender 20B can include similar components as described throughout with "A" and "B" designators.

Figure 4:
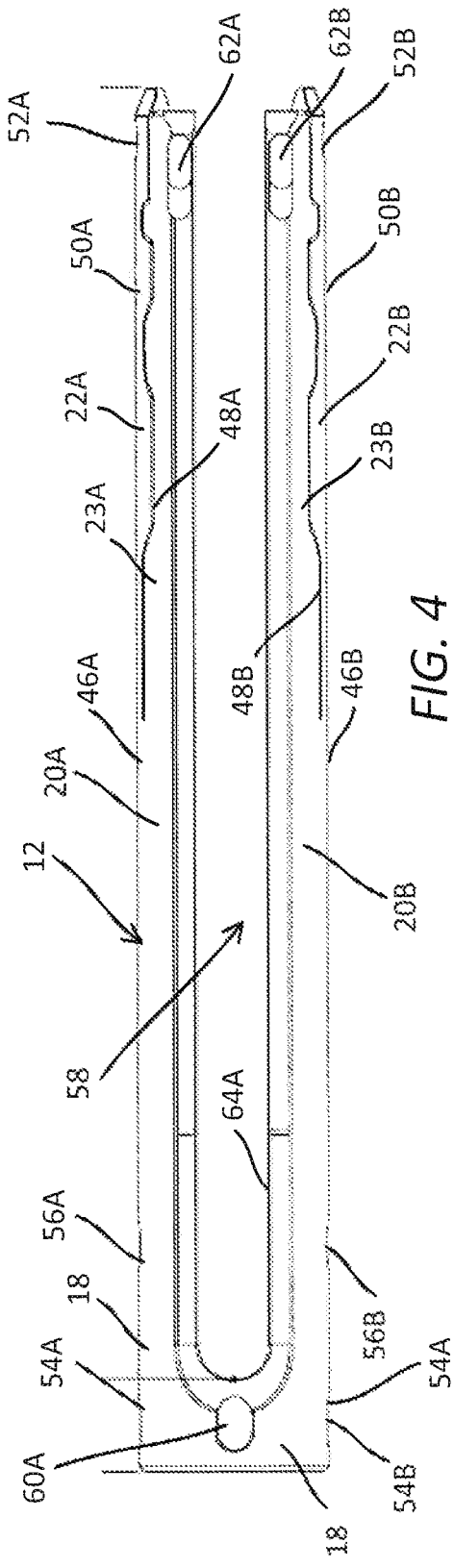
FIG. 4 is a second side view of the tower body of FIGS. 1 and 2 showing an opening for other instruments or implants such as rods according to at least one embodiment of the present disclosure.

Turning to FIG. 4, a side view of the tower body 12 showing an opening 58 between the extenders 20A and 20B is illustrated. The opening 58 is configured to allow for the passage of an elongate fixation member, such as a rod or tether, or other implants or instrumentation into or through the extenders 20A and 20B. The proximal portion 18 of the tower body 12 can comprise the ports 60A and 60B (visible in FIG. 5), which are configured to receive mating components from a reducer or another component. For example, the ports 54A, 54B, 60A and 60B form an array of equally spaced ports that can be coupled to a pair of tangs or projections from a reducer.

The expandable prong 23A can comprise a first coupler socket 62A and the expandable prong 23B can comprise a second coupler socket 62B. The expandable prongs 23A and 23B can form a portion of a u-shaped cutout 64A therebetween, along with portions from the extenders 20A and 20B and the proximal portion 18.

Figure 5:
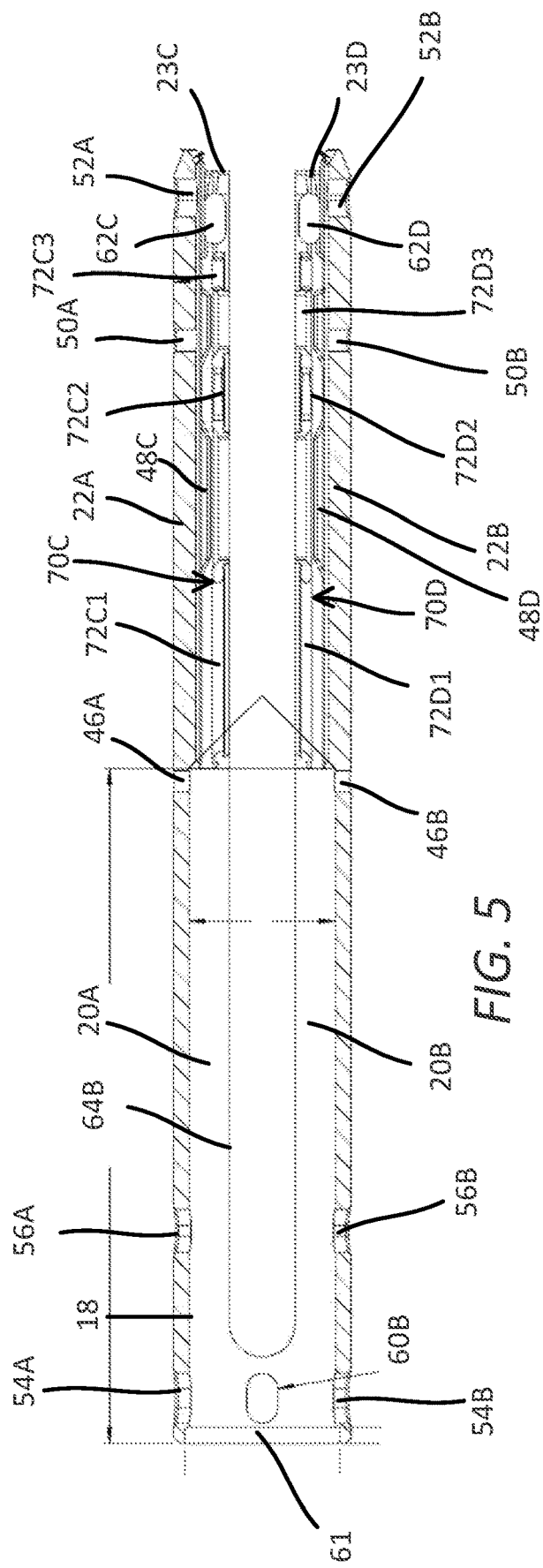
FIG. 5 is a cross-sectional view of the tower body of FIGS. 1 and 2 showing slide rails for the inner slides according to at least one embodiment of the present disclosure.

FIG. 5 is a cross-sectional view of the tower body 12 taken at a section line 5-5 shown in FIG. 3. As shown, the tower body 12 can comprise the extenders 20A and 20B, the expandable prongs 23C and 23D, the port 60B, and a proximal socket 61. The expandable prong 23C can comprise a third coupler socket 62C and the expandable prong 23D can comprise a fourth coupler socket 62D. The expandable prongs 23C and 23D can form a u-shaped cutout 64B therebetween, along with portions from the extenders 20A and 20B and the proximal portion 18.

Figure 6:
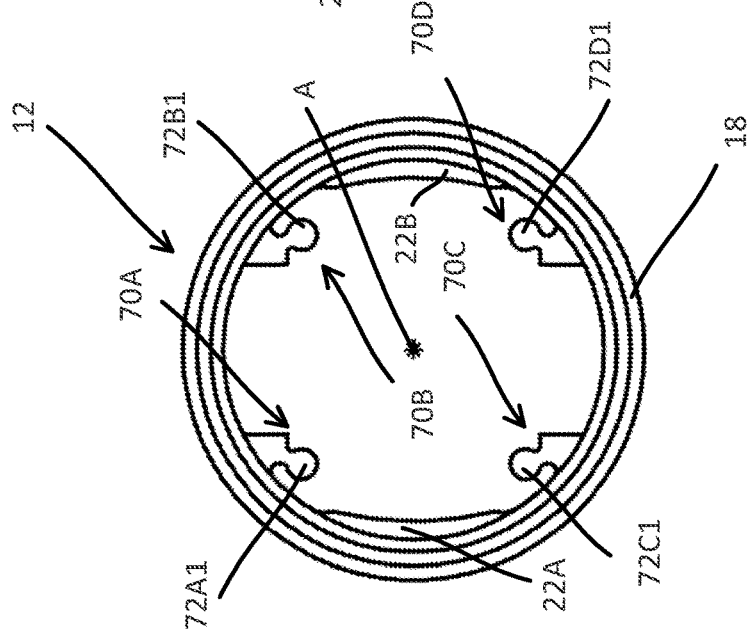
FIG. 6 is a proximal end view of the tower body showing rail segments for the inner slides according to at least one embodiment of the present disclosure.

As can be seen in FIG. 5, the expandable prongs 23C and 23D additionally include one or more slide rails comprising slide rails 70C and 70D. It will be appreciated that in other embodiments the one or more slide rails may comprise any number of slide rails. The slide rail 70C can comprise one or more rail segments comprising rail segments 72C1, 72C2 and 72C3. The slide rail 70D can comprise the one or more rail segments comprising rail segments 72D1, 72D2 and 72D3. As can be seen in FIG. 6, the expandable prongs 23A and 23B can include the one or more slide rails comprising slide rails 70A and 70B. The slide rail 70A can comprise the one or more rail segments comprising rail segments 72A1, 72A2 and 72A3 and the slide rail 70B can comprise the one or more rail segments comprising rail segments 72B1, 72B2 and 72B3 (visible in FIGS. 6 and 19C, 20C, and 21C). It will be appreciated that the half of the tower body 12 shown in FIG. 5 is a mirror image of the half of the tower body 12 shown on the other side of the section line 5-5 of FIG. 3.

The slide rails 70A-70D can interact with corresponding slots 86A and 86B (visible in FIGS. 8-10) disposed on the on the inner slides 14A and 14B to facilitate sliding of the inner slides 14A and 14B against the prongs 23A-23D. As discussed herein, the slide rails 70A-70D can each comprise three axially aligned segments (e.g., rail segments 72C1, 72C2 and 72C3) that interact with two axially aligned segments of the slot 86A or 86B (visible in FIGS. 8-10) on the inner slide 14A or 14B, thereby facilitating locking and expansion of the prongs 23A-23D as discussed herein. The rail segments 72C1, 72C2 and 72C3 can be formed in conjunction with the shape of the break line 48C. That is, where the break line 48C widens the width of the deflectable arm 22A, gaps between the rail segments 72C1, 72C2 and 72C3 are produced. Conversely, where the break line 48C narrows the width of the deflectable arm 22A, the rail segments 72C1, 72C2 and 72C3 are produced.

FIG. 6 is a proximal end view of the tower body 12 showing the slide rails 70A, 70B, 70C and 70D extending relative to an axis A. The slide rails 70A and 70B can be positioned closer to a first side of the proximal portion 18, while the slide rails 70C and 70D can be positioned closer to a second side opposite the first side of the proximal portion 18. As such, the inner slide 14A can slide on the rails 70A and 70C adjacent the deflectable arm 22A and the inner slide 14B can slide on the rails 78B and 70D adjacent the deflectable arm 22B.

As can be seen in FIG. 6, the slide rails 70A, 70B, 70C and 70D comprise cross-sectional profiles having lobed shapes. In the illustrated example, the lobed shaped comprise a circular profile that comprises approximately three-hundred degrees of a circle to provide a circular rail for the inner slides 14A and 14B to slide thereon. It will be appreciated that in other embodiments the lobed shapes may comprise a circular profile having greater than or less than three-hundred degrees of a circle. The lobed shape allows for immobilization of the inner slides 14A and 14B in five degrees of freedom, permitting only axial movement in the direction of axis A when engaged with the slots 86A and 86B, while restraining circumferential and radial movement.

Figure 7:
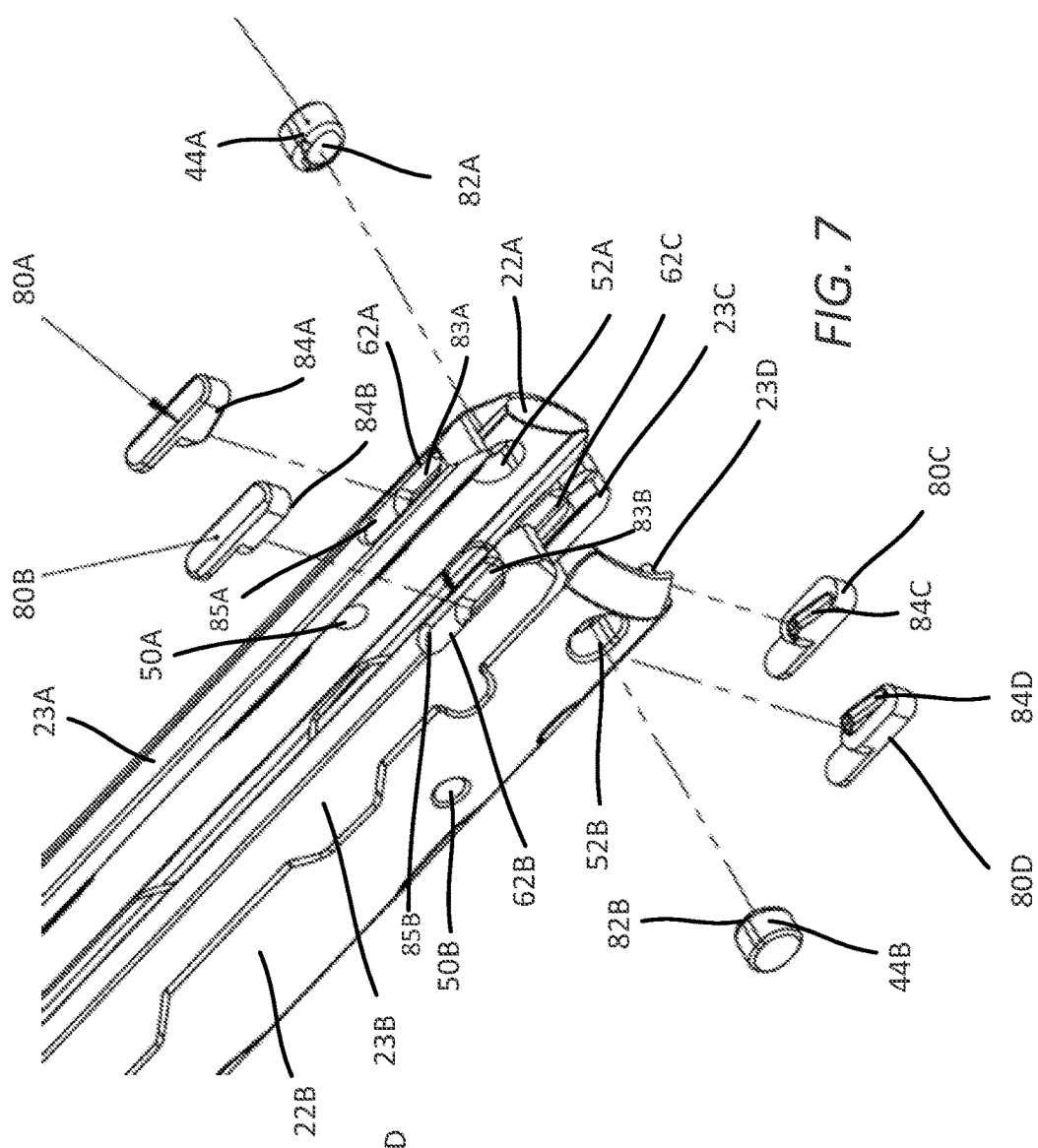
FIG. 7 is a close-up perspective view of a distal end of the tower body of FIGS. 3-5 showing bone anchor housing retainers exploded therefrom according to at least one embodiment of the present disclosure.

FIG. 7 is a close-up perspective view of a distal end of the tower body 12 of FIGS. 3-5 and showing one or more pedicle screw retainers comprising pedicle screw retainers 80A-80D and the retainers 44A and 44B exploded therefrom. It will be appreciated that in other embodiments the one or more pedicle screw retainers may comprise any number of pedicle screw retainers. The retainers 44A and 44B can be disposed within the bores 52A and 52B. The retainers 80A-80D can be disposed within the sockets 62A-62D, respectively. The retainers 44A and 44B and the retainers 80A-80D can include one or more radially inner surfaces comprising radially inner surfaces 82A and 82B and 84A-84D, respectively, that are ramped with respect to the axis A to allow the housing 204 (shown in FIG. 23) of the pedicle screw 200 (shown in FIG. 23) to be inserted proximally into the tower body 12. It will be appreciated that in other embodiments the one or more radially inner surfaces can comprise any number of radially inner surfaces. The radially inner surfaces 82A and 82B and 84A-84D also prevent the housing 204 from sliding distally out of the tower body 12 without the deflectable arms 22A and 22B and the deflectable prongs 23A-23D deflecting or splaying radially outward to release the retainers 44A and 44B and retainers 80A-80D from engagement with the housing.

Figure 21B:
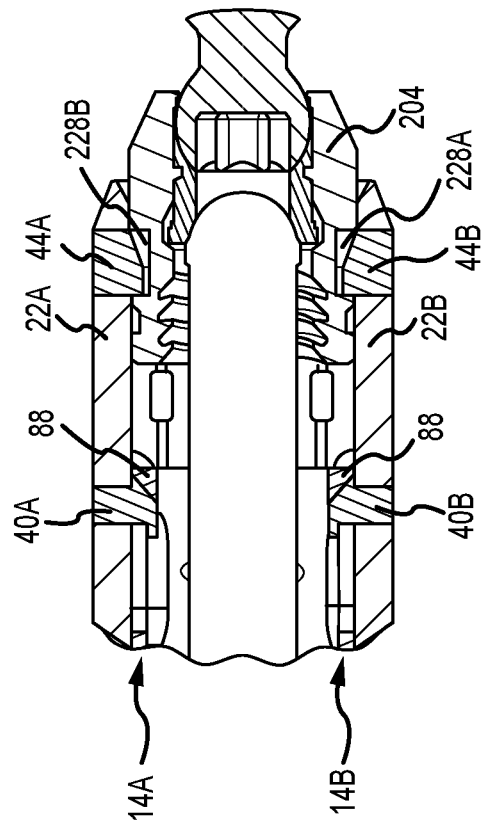
FIG. 21B is cross-sectional view of the distal end of the tower of FIG. 1 showing arm ramps of deflectable arms interfering with windows of inner slides according to at least one embodiment of the present disclosure.
Figure 21C:
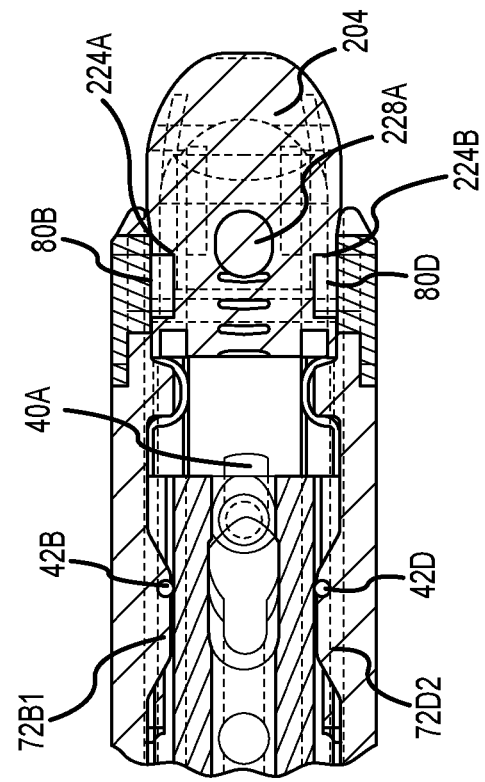
FIG. 21C is side view of the distal end of the tower of FIG. 1 showing rail segments of deflectable prongs interfering with prong pins of an inner slide according to at least one embodiment of the present disclosure.

The deflectable arms 22A and 22B can be provided with the bores 50A and 50B, respectively, to receive the ramps 40A and 40B (shown in FIG. 2). The ramps 40A and 40B can engage with the inner slides 14A and 14B to either lock the deflectable arms 22A and 22B (as shown in FIGS. 19B-19C), to not interfere with the deflectable arms 22A and 22B (as shown in FIGS. 20B-20C), or to push the deflectable arms 22A and 22B outward (as shown in FIGS. 21B-21C).

The ramps 40A and 40B, the retainers 44A and 44B, and the retainers 80A-80D can be configured to have interference fits with the bores 50A and 50B, the bores 52A and 52B, and the sockets 62A-62D, respectively. The bores 50A, 50B, 52A and 52B can comprise simple through bores. In other instances, the bores 50A, 50B, 52A and 52B can comprise any shaped bore. The sockets 62A-62D can comprise elongate, capsule shaped bores 83A-83D having counterbore portions 85A-85D extending from one side. In other embodiments, the sockets 62A-62D can comprise any shaped socket.

FIG. 8 is a first side view of the inner slide 14A showing the slide slots 86A and 86B, a locking window 88 and one or more pin holes comprising pin holes 90A and 90B. FIG. 9 is a second side view of the inner slide 14A of FIG. 8. FIGS. 8 and 9 are discussed concurrently. It will be appreciated that in other embodiments the one or more pin holes can comprise any number of pin holes. The inner slide 14A and inner slide 14B can include similar components with "A" and "B" designators.

The slide slots 86A and 86B can include one or more cutouts comprising cutouts 92A and 92B to break the slide slots 86A and 86B into proximal portions 86A1 and 86B1 and distal portions 86A2 and 86B2. It will be appreciated that in other embodiments the one or more cutouts can comprise any number of cutouts. The inner slide 14A can further comprise a pin hole 94A for interaction with the pin 36A (shown in FIGS. 1 and 2) and ports 96A and 98A for aligning with the ports 54A and 56A (shown in FIG. 5) of the tower body 12. The inner slide 14A can additionally include a slot 100A for interacting with the pin 38A (shown in FIGS. 1 and 2) and one or more through-bores 102 for lightening the inner slide 14A and enabling easier cleaning of the tower body 12 between usage. The pin holes 94A and pin 36A (shown in FIG. 2) can be used to assemble the inner slide 14A with the inner ring 32 (shown in FIG. 12) and the outer ring 30 (shown in FIG. 13). The slot 100A can interact with the pin 38A to help maintain the inner slide 14A in an axial alignment with the deflectable arm 22A, such as when the rail segments 72A1-72A3 and 72C1-72C3 disengage with the slide slots 86A and 86B.

FIG. 10 is a cross-sectional view of the inner slide 14A of FIGS. 8 and 9 showing a cross-sectional profile of the slide slots 86A and 86B. In the illustrated embodiment, the slide slots 86A and 86B have profiles shaped to receive rail segments 72A1-72A3 and 72C1-72C3 and can, thus, have circular profiles. However, in other embodiments, the rail segments 72A1-72A3 and 72C1-72C3 and the slide slots 86A and 86B can be configured to have other profiles that can engage in a slidable relationship.

Figure 11:
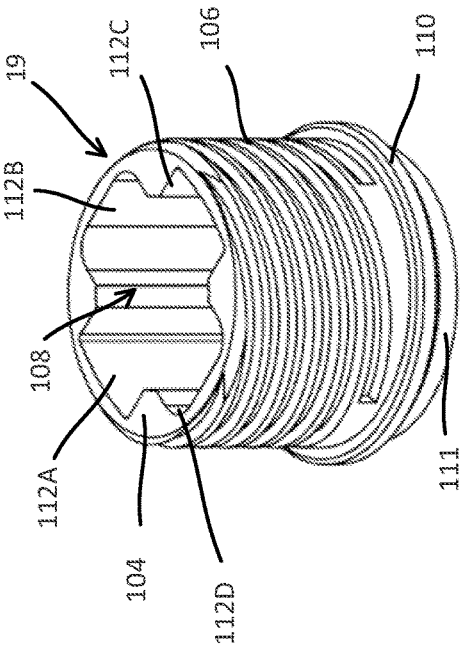
FIG. 11 is a perspective view of a threaded end of FIG. 2 according to at least one embodiment of the present disclosure.

FIG. 11 is a perspective view of the threaded end 19 of FIG. 2. The threaded end 19 can comprise an annular body 104, an external threading 106, an internal channel 108, a radial flange 110 and an axial extension 111. The internal channel 108 can comprise one or more lobes comprising lobes 112A-112D. It will be appreciated that in other embodiments the one or more lobes can comprise any number of lobes. The axial extension 111 can be configured to fit into the socket 61 (shown in FIG. 5). The radial flange 110 can be configured to have approximately the same outer diameter of the proximal portion 18. The external threading 106 can be configured to mate with internal threading of an internal channel 134 of the cap 34 (visible in FIG. 14). The lobes 112A and 112C can be configured to receive the coupling portions 24A and 24B of the inner slides 14A and 14B, respectively. The lobes 112B and 112D of the internal channel 108 can be configured to receive mating components of a reducer in two different orientations.

Figure 12:
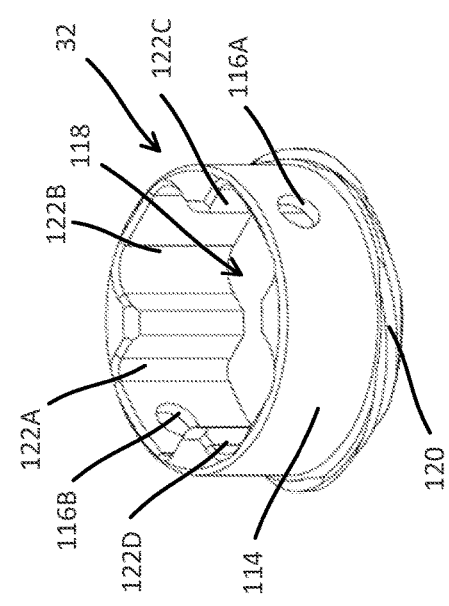
FIG. 12 is a perspective view of an inner ring of FIG. 2 according to at least one embodiment of the present disclosure.

FIG. 12 is a perspective view of the inner ring 32 of FIG. 2. The inner ring 32 can comprise an annular body 114, one or more bores comprising bores 116A and 116B, an internal channel 118 and a flange 120. The internal channel 118 can comprise one or more lobes comprising lobes 122A-122D. It will be appreciated that in other embodiments the one or more lobes can comprise any number of lobes and the one or more bores can comprise any number of bores. The bores 116A and 116B can be configured to receive the pins 36A and 36B to facilitate assembly of the cap assembly 16. The lobes 122A-122D of the internal channel 118 can be configured to align with the lobes 112A-112D of the threaded end 19 (shown in FIG. 11) to facilitate assembly with the coupling portions 24A and 24B of inner slides 14A and 14B and insertion of a feature of a reducer. The flange 120 can be configured to fit inside the internal channel 134 of cap 34 (visible in FIG. 14). The flange 120 can include external threading to allow for engagement with threading on the internal channel 134 of the cap 34 (shown in FIG. 14).

Figure 13:
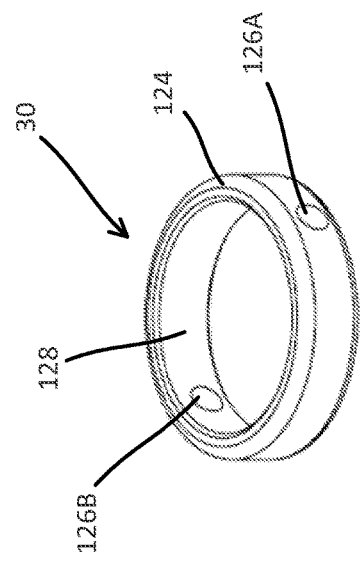
FIG. 13 is a perspective view of an outer ring of FIG. 2 according to at least one embodiment of the present disclosure.

FIG. 13 is a perspective view of the outer ring 30 of FIG. 2. The outer ring 30 can comprise an annular body 124, one or more bores comprising bores 126A and 126B and an internal channel 128. It will be appreciated that in other embodiments the one or more bores can comprise any number of bores. The annular body 124 can be configured to fit around the annular body 114 of the inner ring 32. The bores 126A and 126B can be configured to receive the pins 36A and 36B (shown in FIG. 2) to facilitate assembly of the cap assembly 16.

Figure 14:
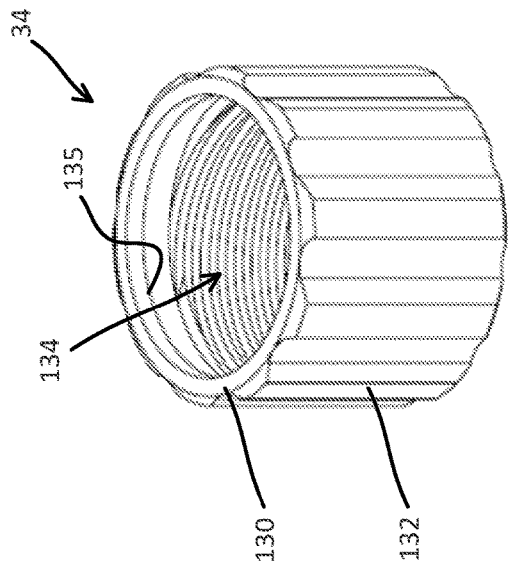
FIG. 14 is a perspective view of a cap of FIG. 2 according to at least one embodiment of the present disclosure.

FIG. 14 is a perspective view of the cap 34 of FIG. 2. The cap 34 can comprise an annular body 130, one or more grip features 132, an internal channel 134 and a flange 135. It will be appreciated that in other embodiments the one or more grip features can comprise any number of grip features. The annular body 130 can be configured to surround the annular body 104 of the threaded end 19. In particular, threading provided on the internal channel 134 can be configured to mate with the external threading 106 of the threaded end 19. In the illustrated embodiment, the one or more grip features 132 can comprise ribs to facilitate rotating of the cap 134 about the axis A. In other examples, the one or more grip features 132 can comprise knurling and the like.

In order to assemble the cap assembly 16 (shown in FIG. 1), the axial extension 111 (shown in FIG. 11) can be inserted into the socket 61 (shown in FIG. 5) so that the radial flange 110 is flush with the proximal portion 18 of the tower body 12. The inner slides 14A and 14B can be slid into the lobes 112A and 112C. The inner ring 32 can be positioned so that the bores 94A and 94B (shown in FIG. 8) of the inner slides 14A and 14B align with the bores 116A and 116B. The cap 34 can then be threaded onto the threaded end 19 such that the flange 135 sits on the flange 120. The outer ring 30 can be positioned adjacent to the flange 135 so that the bores 126A and 126B align with the bores 116A and 116B. The pins 36A and 36B can be inserted into the bores 126A and 126B and the bores 116A and 116B, respectively. The flange 135 of the cap 34 can be trapped between the flange 120 of the inner ring 32 and the outer ring 30. Thus, as the cap 34 is threaded up and down along the axis A, the inner slides 14A and 14B can be pushed and pulled along to activate features illustrated in FIG. 18 with the pedicle screw housing 204 (shown in FIG. 23).

Figure 15:
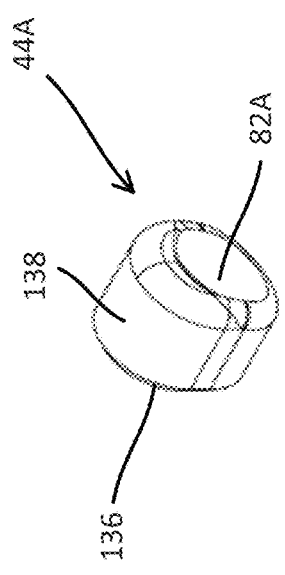
FIG. 15 is a perspective view of a bone anchor housing retainer of FIG. 7 according to at least one embodiment of the present disclosure.

FIG. 15 is a perspective view of the retainer 44A of FIG. 7. The retainer 44A can comprise a radially inner surface 82A and an external surface 136 of a body 138. The body 138 can be configured to be interference fit into the bore 52A or the bore 52B (shown in FIG. 7). The external surface 136 can be configured to be flush with the outer surface of the tower body 12. The inner surface 82A can be disposed at an angle to the external surface 136. The body 138 and the bores 52A and 52B can be oblong in shape such that the slope of the internal surface 82A can be directionally aligned relative to the axis A. The slope of the internal surface 82A can be oriented such that the internal surface 82A increases in height moving proximally and decrease in height moving distally. As such, the pedicle screw housing 204 (shown in FIG. 23) moving proximally into the tower body 12 can displace the deflectable arms 22A and 22B, but once inserted the pedicle screw housing cannot be pulled distally without active deflection of the arms 22A and 22B.

Figure 16:
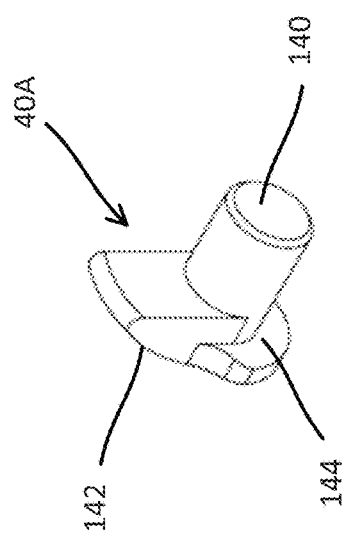
FIG. 16 is a perspective view of an arm ramp of FIG. 2 according to at least one embodiment of the present disclosure.

FIG. 16 is a perspective view of the arm ramp 40A of FIG. 2. The arm ramp 40A can comprise a post 140, a ramp 142 and a lock 144. The post 140 can be configured to be inserted into one of the bores 50A and 50B (shown in FIG. 7). The posts 140 and the bores 50A and 50B can be configured to have an interference fit. The posts 140 can engage the deflectable arms 22A and 22B and the arm ramp 40A can be oriented such that the ramps 142 moves a distance that increases in height moving proximally and decreases in height moving distally. As such, the deflectable arms 22A and 22B are displaced outward when slides 14A and 14B are moved proximally to engage the ramps 142. The lock 144 can comprise a flange extending out from the post 140 in the opposite direction of the ramp 142. The lock 144 can be configured to be positioned over one of the slides 14A and 14B to trap one of the deflectable arms 22A and 22B against one of the slides 14A and 14B, as shown in FIG. 19B.

Figure 17B:
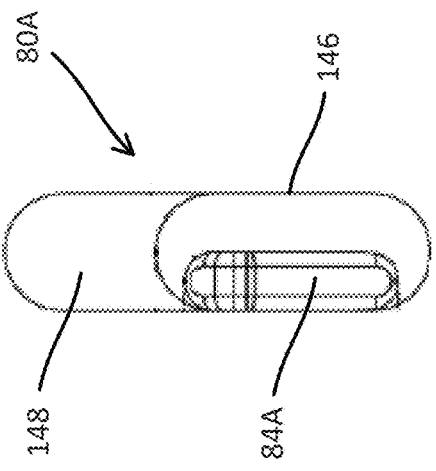
FIG. 17B is a front view of the bone anchor housing retainer of FIG. 17A according to at least one embodiment of the present disclosure.
Figure 17A:
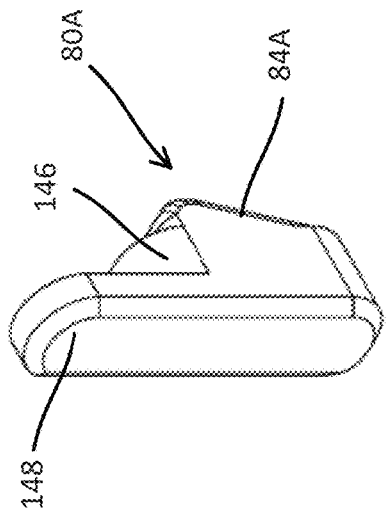
FIG. 17A is a perspective view of a bone anchor housing retainer of FIG. 7 according to at least one embodiment of the present disclosure.

FIG. 17A is a perspective view of the pedicle screw retainer 80A of FIG. 7. FIG. 17B is a front view of the pedicle screw retainer 80A of FIG. 17A. The body 146 can further comprise an extension 148. The extension 148 can be configured to be seated in one of the counterbores 85A and 85B (shown in FIG. 7).

Figure 18:
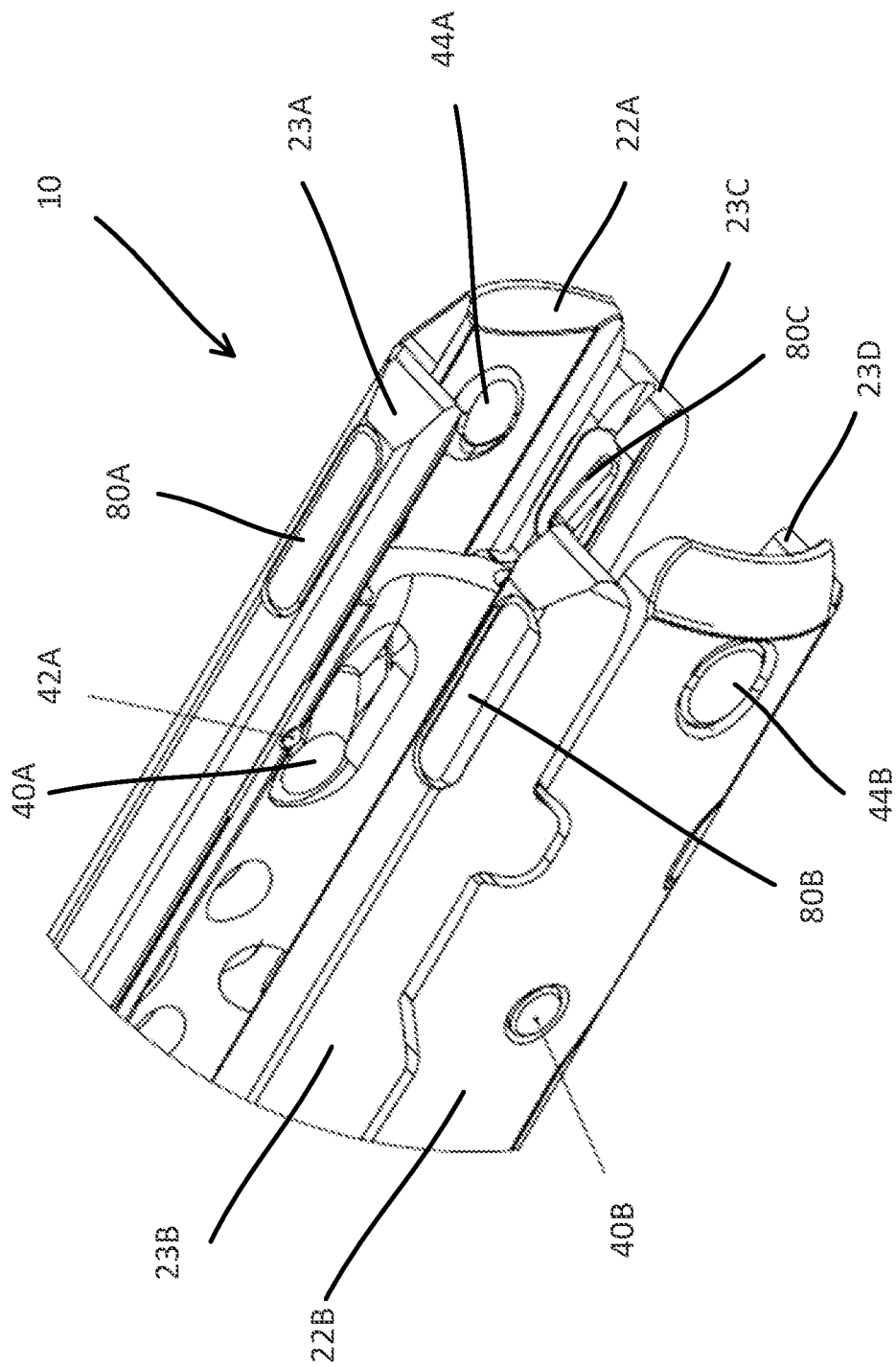
FIG. 18 is a perspective view of a distal end of an assembled bone anchor tower of the present application showing assembly of features configured to hold a bone anchor housing and splay deflectable arms and deflectable prongs of the tower body to release the bone anchor housing according to at least one embodiment of the present disclosure.

FIG. 18 is a perspective view of a distal end of an assembled pedicle screw tower 10 of the present application showing an assembly of features configured to hold the pedicle screw housing 204 (shown in FIG. 23) and splay the deflectable arms 22A and 22B and the deflectable prongs 23A-23D of the tower body 12 to release the pedicle screw housing 204.

FIG. 19A is a side view of the cap assembly 16 of FIG. 1 showing the cap 34 in a fully advanced position. The cap 34 can be abutted against the proximal portion 18 of the tower body 12. Thus, the cap 34 can be positioned to move the inner slides 14A and 14B (shown in FIG. 2) to their distal-most positions. FIGS. 19B and 19C show the distal end of tower 10 with the cap 34 in the position of FIG. 19A.

FIG. 19B is cross-sectional view of the distal end of the tower 10 of FIG. 1 showing the arm ramps 40A and 40B of the deflectable arms 22A and 22B locked with the windows 88 of the inner slides 14A and 14B and the retainers 44A and 44B of the deflectable arms 22A and 22B engaged with the pedicle screw housing 204. The retainers 44A and 44B can be disposed in the sockets 228A and 228B, respectively, of the housing 204. The locks 144 of the ramps 40A and 40B can be engaged with the corresponding flanges 150 on the windows 88 of the inner slides 14A and 14B to retain the deflectable arms 22A and 22B against the inner slides 14A and 14B, thereby preventing the deflectable arms 22A and 22B from being able to be deflected radially outward.

FIG. 19C is side view of the distal end of tower 10 of FIG. 1 showing rail segments 72B2 and 72D2 of the deflectable prongs 23B and 23D engaged with the slots 86A and 86B of the inner slide 14B and the pedicle screw retainers 80B and 80D of the deflectable prongs 23B and 23D engaged with the pedicle screw housing 204. The retainers 80B and 80D can be disposed in the sockets 224A and 224B, respectively, of the housing 204. The rail segment 72B2 can engage the slot segment 86A1. The rail segment 72B3 can engage the slot segment 86A2. The rail segment 72D2 can engage the slot segment 86B1. The rail segment 72D3 can engage the slot segment 86B2. Thus, the deflectable prongs 23B and 23D can be prevented from moving radially outward.

FIG. 20A is a side view of the cap assembly 16 of FIG. 1 showing the cap 34 in a partially retracted position. The cap 34 can be rotated to engage the threading 106 (shown in FIG. 11) to move away from the proximal portion 18 of the tower body 12 such that a portion of the threaded end 19 can be exposed. As the cap 34 moves, the inner slides 14A and 14B can be pulled proximally. FIGS. 20B and 20C show the distal end of the tower 10 with the cap 34 in the position of FIG. 20A.

FIG. 20B is cross-sectional view of the distal end of tower 10 of FIG. 1 showing the arm ramps 40A and 40B of the deflectable arms 22A and 22B positioned within the windows 88 of the inner slides 14A and 14B and the retainers 44A and 44B of the deflectable arms 22A and 22B engaged with the pedicle screw housing 204. The retainers 44A and 44B can still be disposed in the sockets 228A and 228B, respectively, of the housing 204. The locks 144 of the ramps 40A and 40B can be disengaged with the corresponding flanges 150 on the windows 88 of the inner slides 14A and 14B to allow the deflectable arms 22A and 22B to be capable of radial outward deflection.

FIG. 20C is side view of the distal end of tower 10 of FIG. 1 showing the rail segments 72B2 and 72D2 of the deflectable prongs 23B and 23D disengaged with the slots 86A and 86B of the inner slide 14B and the pedicle screw retainers 80B and 80D of the deflectable prongs 23B and 23D engaged with the pedicle screw housing 204. The retainers 80B and 80D can still be disposed in the sockets 224A and 224B, respectively, of the housing 204. The rail segment 72B2 can be disengaged from the slot segment 86A1. The rail segment 72B3 can be disengaged from the slot segment 86A2. The rail segment 72D2 can be disengaged from the slot segment 86B1. The rail segment 72D3 can be disengaged from the slot segment 86B2. Thus, the deflectable prongs 23B and 23D can be allowed to deflect radially outward.

Figure 21A:
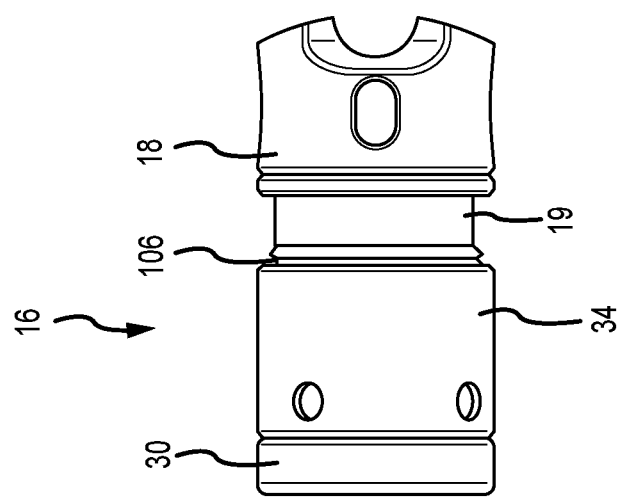
FIG. 21A is a side view of the cap assembly of FIG. 1 showing the cap in a fully retracted position to providing separating functionality with a pedicle screw housing according to at least one embodiment of the present disclosure.

FIG. 21A is a side view of the cap assembly 16 of FIG. 1 showing the cap 34 in a fully retracted position. The cap 34 can be rotated to engage the threading 106 (shown in FIG. 11) to move away from the proximal portion 18 of the tower body 12 such that a portion of the threaded end 19 and the threading 106 can be exposed. As the cap 34 moves, the inner slides 14A and 14B can be pulled proximally. FIGS. 21B and 21C show the distal end of the tower 10 with the cap 34 in the position of FIG. 21A.

FIG. 21B is cross-sectional view of the distal end of the tower 10 of FIG. 1 showing the arm ramps 40A and 40B of the deflectable arms 22A and 22B interfering with the windows 88 of the inner slides 14A and 14B. This causes the retainers 44A and 44B of the deflectable arms 22A and 22B to disengage with the pedicle screw housing 204 (not shown). The windows 88 of the inner slides 14A and 14B can be pushed onto the ramps 142 of the ramps 40A and 40B to push the deflectable arms 22A and 22B radially outward. Thus, as can be seen in FIG. 22, the retainers 44A and 44B can be deflected radially outward, so as to be capable of withdrawal from the sockets 228A and 228B, respectively, of the housing 204.

FIG. 21C is side view of the distal end of the tower 10 of FIG. 1 showing the rail segments 72B2 and 72D2 of the deflectable prongs 23B and 23D interfering with the prong pins 42B and 42D of the inner slide 14B. This causes the pedicle screw retainers 80B and 80D of the deflectable prongs 23B and 23D to disengage with the pedicle screw housing 204 (not shown). Thus, as can be seen in FIG. 22, the retainers 80B and 80D can be deflected radially outward, so as to be capable of withdrawal from the sockets 224A and 224B, respectively, of the housing 204.

Figure 22:
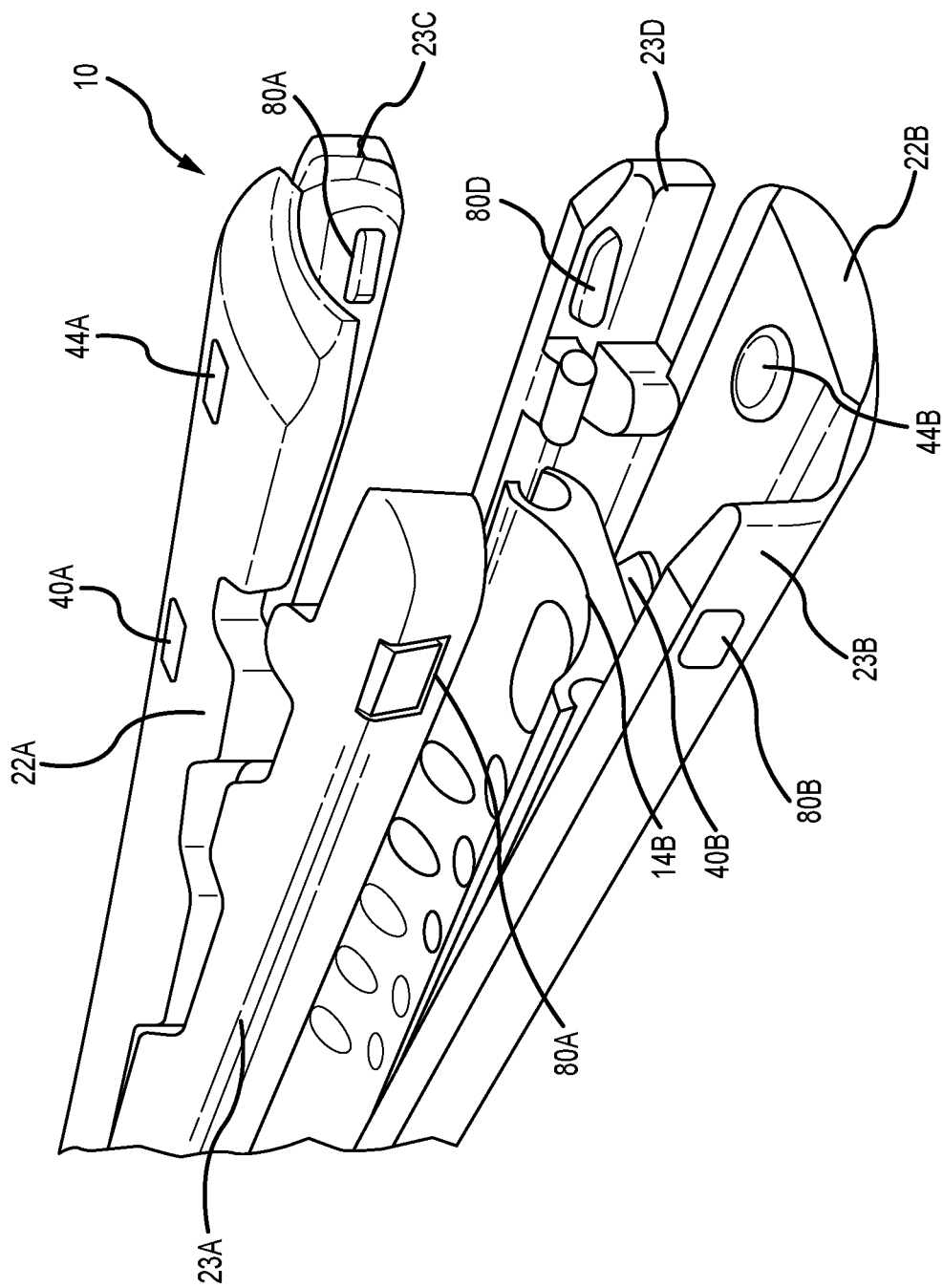
FIG. 22 is a perspective view of the distal end of the tower of FIGS. 21B and 21C with the deflectable arms and deflectable prongs in a splayed state according to at least one embodiment of the present disclosure.

FIG. 22 is a perspective view of the distal end of the tower 10 of FIGS. 21B and 21C with the deflectable arms 22A and 22B and the deflectable prongs 23A-23D in a splayed state so as to be pushed radially outward from the center axis A of the tower body 12 and away from the inners slides 14A and 14B. As such, spaces or gaps can form between the deflectable prongs 23A and 23C and the deflectable arm 22A, and between the deflectable prongs 23B and 23D and the deflectable arm 22B, thereby producing clearance for the pedicle screw housing 204 to move axially in and out of the tower body 12.

Figure 23:
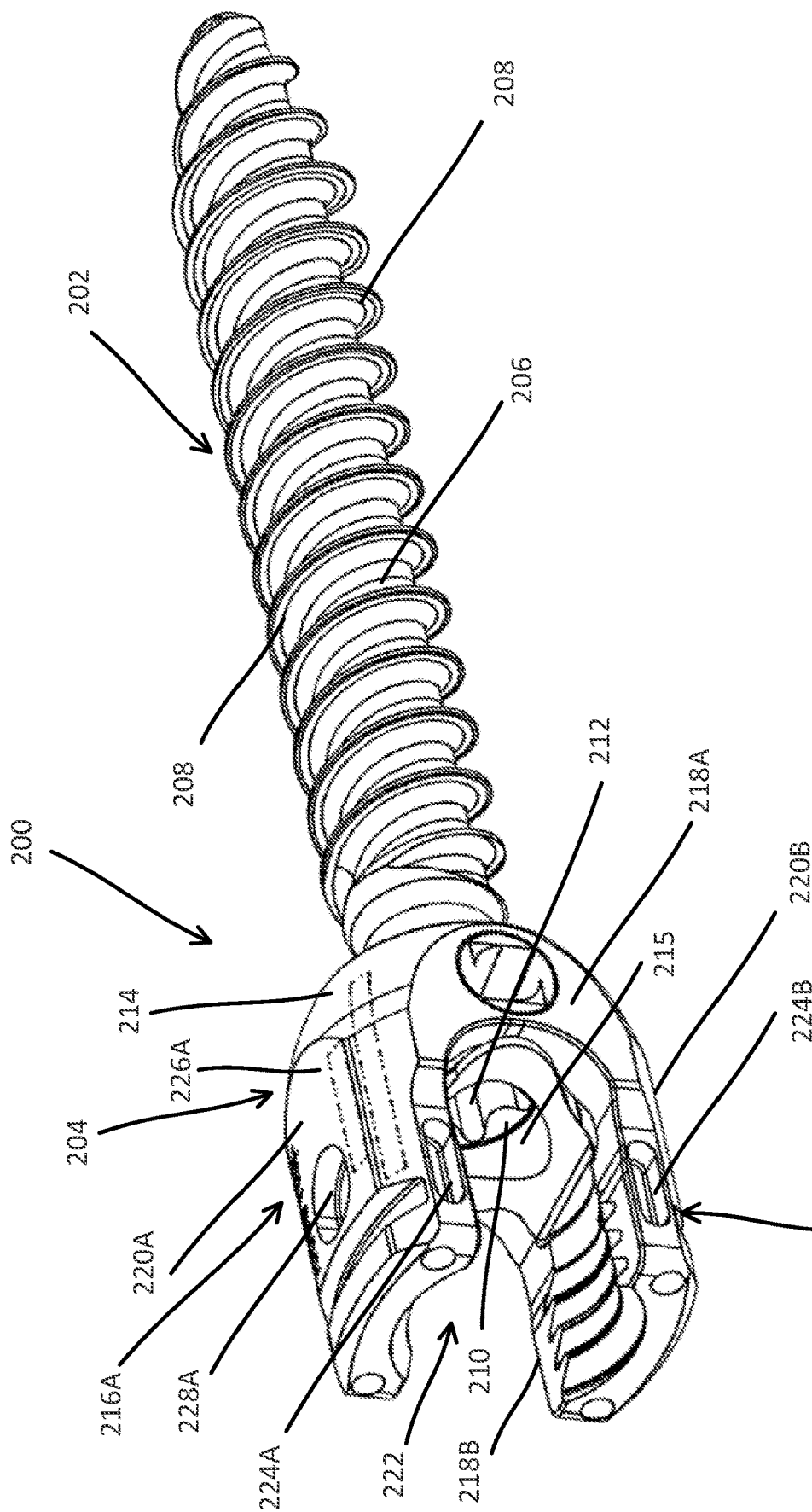
FIG. 23 is a perspective view of a bone anchor comprising a threaded fastener and a rod housing suitable for use with the bone anchor tower of FIGS. 1-22 according to at least one embodiment of the present disclosure.

FIG. 23 is a perspective view of the pedicle screw 200 (also referred to as a bone anchor) comprising a threaded fastener 202 and a rod housing 204. The threaded fastener 202 can comprise a shaft 206, a threading 208, a head 210 and a socket 212. The rod housing 204 can comprise a base portion 214, an aperture 215, a first extension 216A, a second extension 216B, a first open face 218A, a second open face 218B, a first closed face 220A, a second closed face 220B and a channel 222. The first open face 218A can comprise a first socket 224A and a second socket 224B. The first closed face 226A can comprise a first socket 228A.

The rod housing 204 can be rotated relative to the threaded fastener 202 to position the extensions 216A and 216B in different positions. The shaft 206 can be rotated within the base portion 214 via rotational engagement of the socket 212 with an instrument such as, for example, a screwdriver. A fixation element, such as a rod or tether, can be positioned between the extensions 216A and 216B and secured therein with a set screw. Although not seen in FIG. 23, the housing 204 can comprise counterpart sockets to the sockets 224A, 224B and 228A on the far side of the housing 204 on open and closed faces. The sockets 224A and 224B can be provide alongside a channel formed by the extensions 216A and 216B on the open face 218A, and the socket 228A can be formed on the closed face 226A. The socket 224A and its counterpart socket can lie in a plane transverse to the central axis A of the tower 10. The socket 224B and its counterpart socket can lie in a plane transvers to the central axis A of the tower 10. The socket 228A and its counterpart socket can lie in a plane transverse to the central axis A of the tower 10. The planes of the sockets 224A and 224B and their counterparts can be transverse to the plane of the socket 228A and its counterpart.

The systems, devices and methods discussed in the present application can be useful in performing spinal correction procedures using extenders or towers that can couple to bone anchor or pedicle screw housings. The present disclosure describes tower extenders that can attach to a bone anchor housing in multiple circumferential locations around the perimeter of the pedicle screw housing relative to a center axis of the tower extender. Further, the tower extenders can be attached axially to the housing without rotation of the tower extenders. In other words, the tower extenders can be pushed onto the housing to engage with the pedicle screw. The attachment points of the tower extenders can be arranged in pairs that are orthogonal to each other to allow for secure attachment to the bone anchor housing. The attachment points can comprise protrusions that can extend into mating recesses in the bone anchor housing. The reverse configuration can additionally be used. The protrusions can be mounted to deflectable members of the tower extender. The deflectable members can be freely deflectable to allow the tower extender to slip over the bone anchor housing. The deflectable members can additionally be prevented from deflecting to prevent the bone anchor housing from separating from the tower extender. The deflectable members can additionally be pushed radially outward to facilitate disengagement of the protrusions from the recesses. The deflectable members can be locked and pushed via axially sliding of a slide arrangement or actuation mechanism within the tower extender. As such, the tower extenders of the present disclosure can provide robust attachment to a pedicle screw housing to prevent undesirable detachment during a procedure, but can be easily operated and actuated by a control knob to prevent and allow detachment and attachment.

Turning to FIGS. 24A-54, a reducer 300 according to at least one embodiment of the present disclosure is described. FIG. 24A is a side view of the reducer 300 for the pedicle screw tower 10 (shown in FIG. 1) of the present disclosure. The reducer 300 comprises a palm handle 302, a reducer assembly 304 and a reducing shaft 306. The palm handle 302 can comprise a grip 314 and a button 315. FIG. 24B is a perspective view of the reducer 300 of FIG. 24A with the palm handle 302 removed to show a proximal end of a driver 308. The reducer assembly 304 can comprise a clutch mechanism 310 and a locking mechanism 312. FIGS. 24A and 24B are discussed concurrently below.

The reducer 300 can be used in conjunction with the pedicle screw tower 10 (shown in FIG. 1) to push an elongate stabilization member, such as a rod 522 (shown FIG. 54), into the pedicle screw housing 204 (shown in FIG. 23). For example, with the pedicle screw tower 10 attached to the housing 204, as shown in FIGS. 19B and 19C, the reducing shaft 306 can be inserted into the ring 30 (shown in FIG. 1) and the proximal socket 61 (shown in FIG. 5) of the tower body 12. The reducer 300 can be advanced along the tower 10 so that the locking mechanism 312 of the reducer assembly 304 attaches to the ports 54A-54B or 60A-60B (shown in FIGS. 3-5). The locking mechanism 312 can be operated to allow the reducer assembly 304 to slide freely over the tower body 12 and then to lock onto the tower body 12. The clutch mechanism 310 can be operated to allow the reducing shaft 306 to slide freely through the reducer assembly 304 until engaged with the stabilization member. The clutch mechanism 310 can then be adjusted to engage threading of the threaded shaft portion 330 on the reducing shaft 306. The palm handle 302 can be rotated to mechanically push the reducing shaft 306, as well as the stabilization member, into the pedicle screw housing 204. Thereafter, the driver 308 can be operated through the palm handle 302, or with the palm handle 302 removed, to push a closure device, e.g., a set screw or a closure device 521 (shown in FIG. 54), into engagement with the housing 204 to lock the stabilization member in engagement with the pedicle screw housing 204. The driver 308 can be spring loaded to position a pre-loaded closure device within the reducing shaft 306. The driver 308 can be advanced distally by an operator to engage the closure device with the pedicle screw housing 204.

As described with reference to FIGS. 26 and 46, the reducer 300 can incorporate a linearly biased and actuated driver, such as the driver 308 or a driver configured to "stab and grab", for holding a closure device within the reducing shaft 306 while reducing is being performed and that can subsequently be deployed via the driver 308 to attach to the housing 204 to hold a stabilization element within the housing 204.

As is described with reference to FIGS. 47-49, the locking mechanism 312 can be operated in three operating states to allow the reducer 300 to freely slide on the tower body 12 in an open state, to attach to the tower body 12 in an unlocked state, and to lock the tower body 12 in a locked state.

As described with reference to FIGS. 50-53, the clutch mechanism 310 can comprise a three-pawl chuck that can be operated in two operating states to allow the reducing shaft 306 to freely slide within the reducer assembly 304, and to engage threading on the reducing shaft 306 to allow the reducing shaft 306 to be mechanically pushed within the reducer assembly 304.

Figure 25:
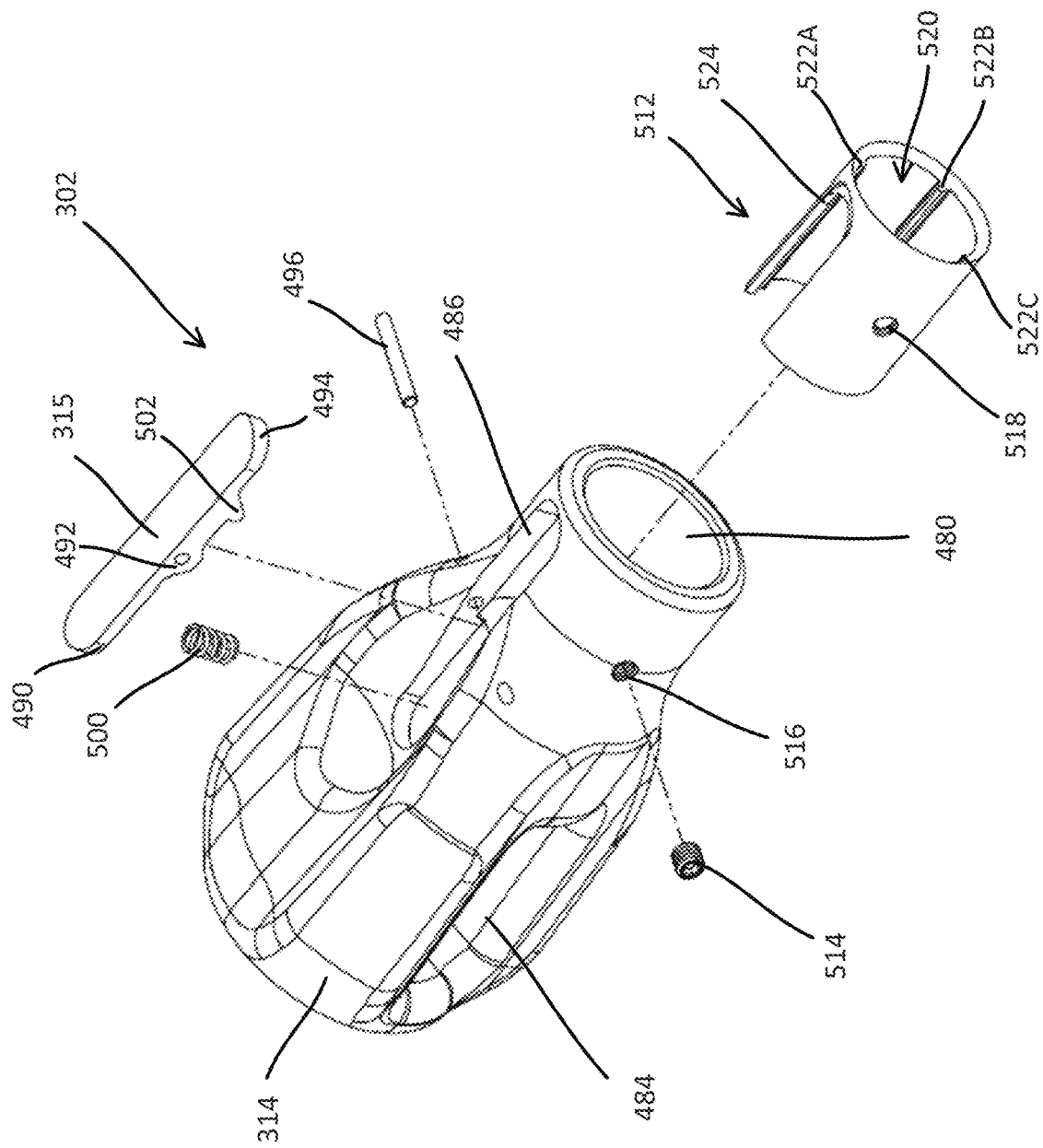
FIG. 25 is an exploded perspective view of the palm handle of FIG. 24A according to at least one embodiment of the present disclosure.

FIG. 25 is an exploded perspective view of the palm handle of FIG. 24A. The palm handle 302 can comprise a socket 480, a driver channel 482, one or more windows 484 and a button seat 486. It will be appreciated that in other embodiments the one or more windows can comprise any number of windows. A button 315 can be positioned in the button seat 486 and can comprise a first end 490, a pivot 492 and a second end 494. The button 315 can comprise an elongate body configured to rotate at the pivot 492 such as via a coupling of the button 315 to the palm handle 302 via a pin 496. A biasing element such as, for example, a spring 500 or another biasing element can be positioned between the first end 490 and the button seat 486. The second end 494 can include a tang 502 for engaging clutch the housing 319 (shown in FIGS. 31 and 32). An insert 512 can be positioned in the socket 480 and retained therein by a fastener 514 that can extend into a bore 516 to engage a bore 518. The fastener 514 can be threaded into engagement with the bores 516 and 518. The insert 512 can comprise a cylindrical body forming a passage 520 into which the clutch housing 319 (shown in FIG. 31) can be inserted. One or more lugs such as lugs 522A-522C can be positioned between adjacent lugs 354 of the clutch housing 319, as can be seen in FIG. 46. It will be appreciated that in other embodiments the one or more lugs can comprise any number of lugs. The insert 512 can include a cutout 524 to accommodate the button seat 486.

Figure 26:
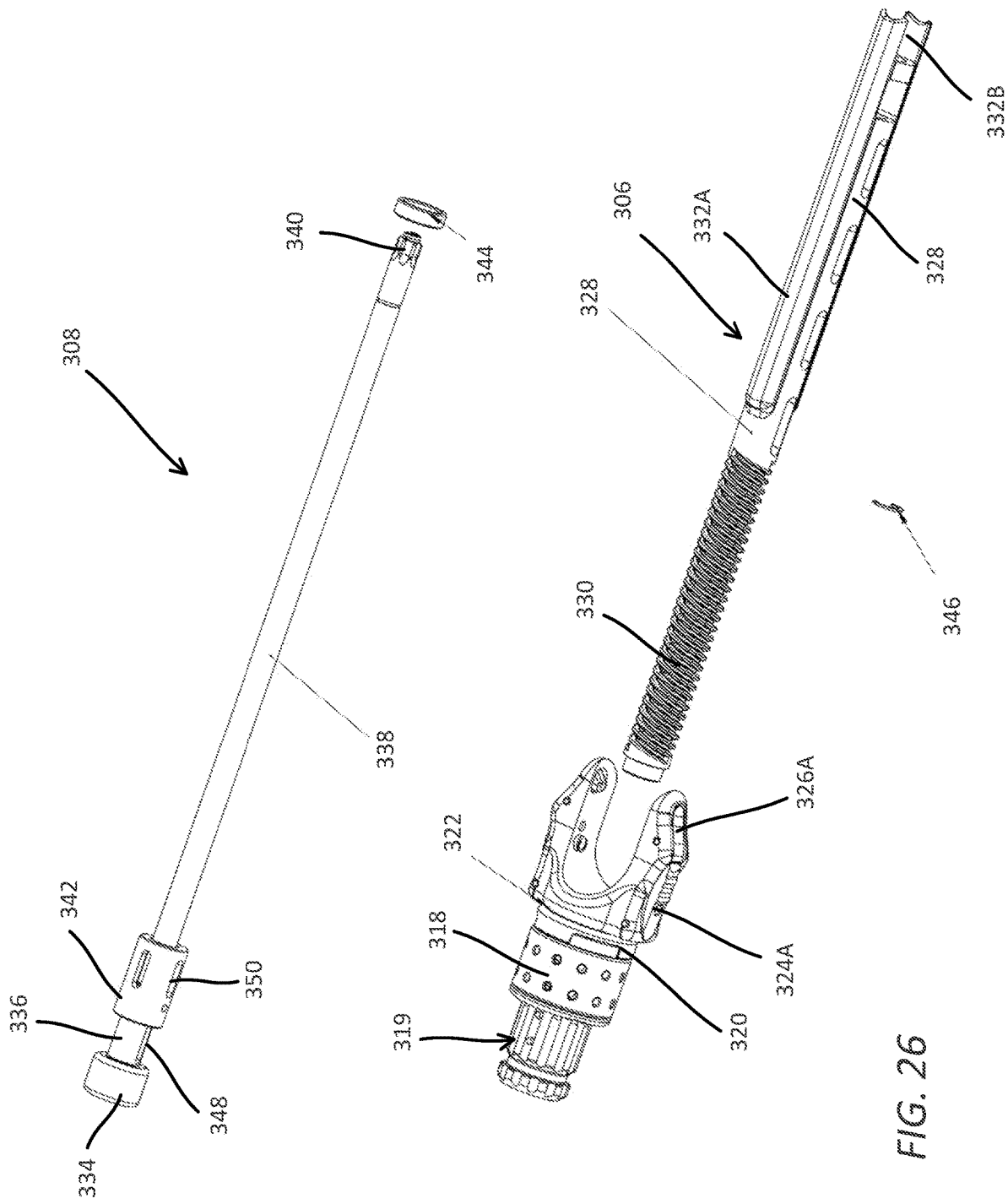
FIG. 26 is an exploded view of the reducer of FIG. 24B showing the reducer assembly, the reducing shaft and the driver according to at least one embodiment of the present disclosure.

FIG. 26 is an exploded view of reducer 300 of FIG. 24A showing the reducer assembly 304, the reducing shaft 306 and the driver 308. The reducer assembly 304 can comprise the clutch mechanism 310 and the locking mechanism 312. The clutch mechanism 310 can comprise clutch knob 318, the clutch housing 319 and the clutch washer 320. The locking mechanism 312 can comprise the reducer body 322, an upper release lever 324A and a lower release lever 326A. The reducing shaft 306 can comprise a shaft body 328, a threaded shaft portion 330, a first rail 332A and a second rail 332B. The driver 308 can comprise a knob 334, an actuation portion 336, shaft 338 and a tip 340. The driver 308 can be connected to a plunger 342, a ring 344 and a clip 346. The actuation portion 336 can comprise one or more slots such as slots 348 and the plunger 342 can comprise one or more slots such as slots 350.

The upper and lower release levers 324A and 326A of the reducer body 322 can be used to couple and uncouple the reducer assembly 304 from a pedicle screw extender, such as the tower 10 of FIG. 1. The shaft body 328 of the reducing shaft 306 can be inserted into a socket 374 (shown in FIG. 28) of the reducer body 322 such that the threaded shaft portion 330 extends proximally of the clutch housing 319. The clutch knob 318 can be rotated to a position to allow threading of the threaded shaft portion 330 to pass freely through the reducer body 322 and can be rotated to another position to allow threading of the threaded shaft portion 330 to engage the pawls 316A-316C (shown in FIG. 28) within the clutch housing 319. The driver 308 can be inserted into the proximal end of the threaded shaft portion 330 such that a tip 340 can be positioned between the rails 332A and 332B of the reducing shaft 306. The plunger 342 can be coupled to the actuation portion 336 and a spring 508 (shown in FIG. 46) can bias the shaft 338 proximally (shown in FIG. 26). The knob 334 can be linearly actuated by a user in the distal direction to move the shaft 338 distally from the retracted position to selectively engage a closure device with a pedicle screw housing.

Figure 27:
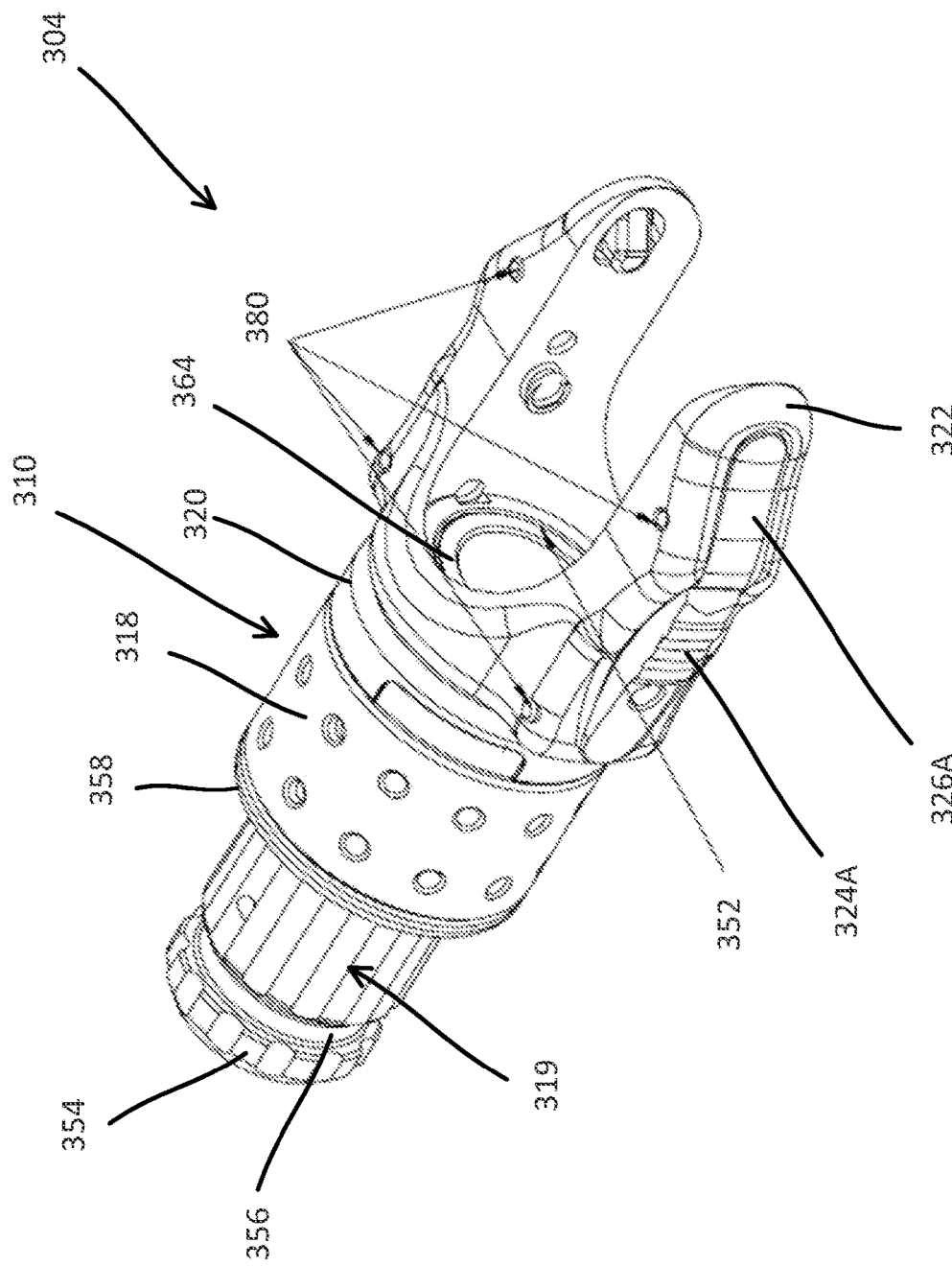
FIG. 27 is a perspective view of the reducer assembly of FIG. 26 comprising a clutch mechanism and a locking mechanism according to at least one embodiment of the present disclosure.
Figure 28:
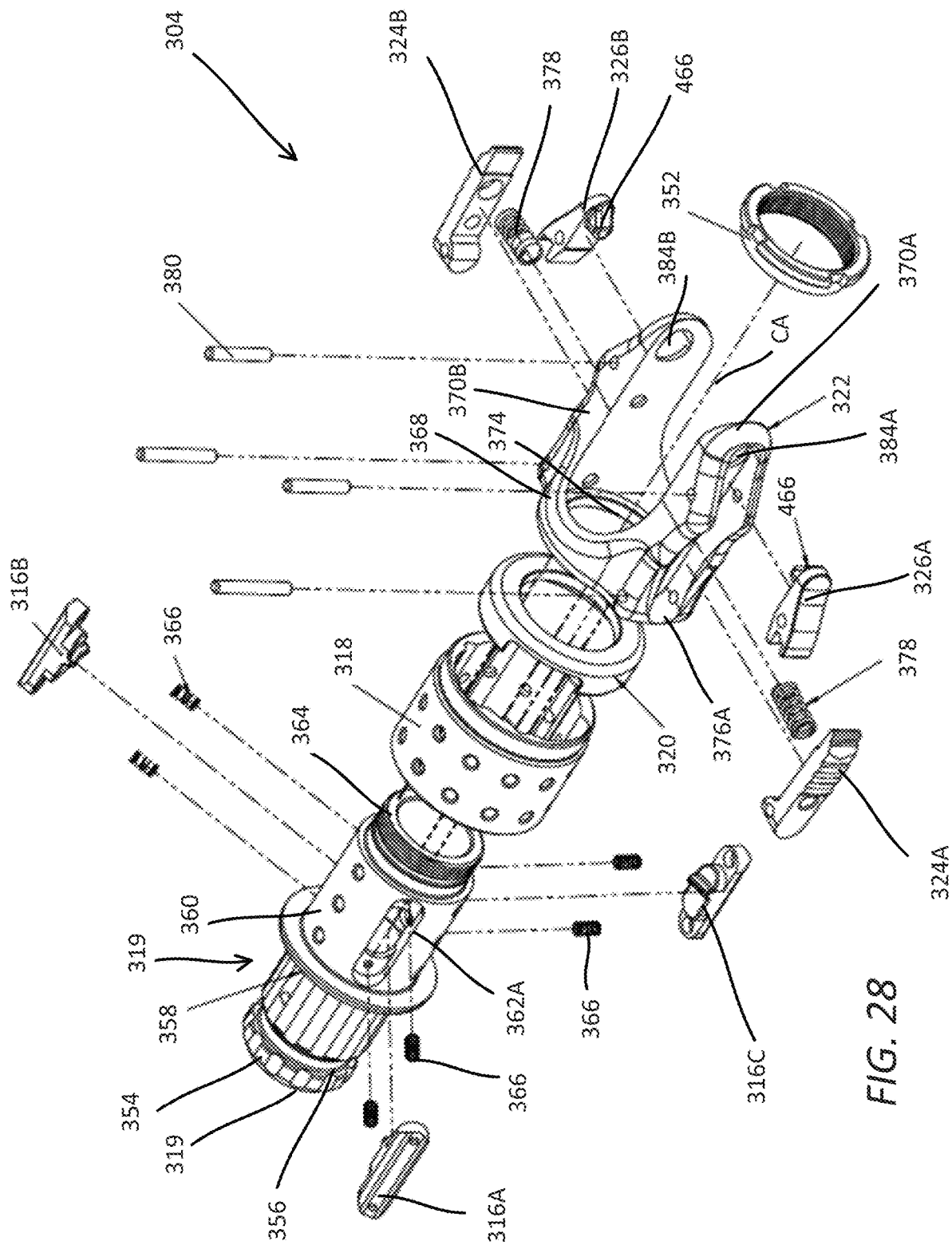
FIG. 28 is an exploded view of the reducer assembly of FIG. 27 according to at least one embodiment of the present disclosure.

FIG. 27 is a perspective view of the reducer assembly 304 of FIG. 26 comprising the clutch mechanism 310 and the locking mechanism 312. FIG. 28 is an exploded view of the reducer assembly 304 of FIG. 27. FIGS. 27 and 28 are discussed concurrently.

The clutch housing 319 can comprise one or more lugs such as lugs 354, a channel 356, flange 358, a cylinder portion 360, one or more windows such as windows 362A-362C and a threaded end 364. The clutch mechanism 310 can further comprise one or more pawls such as pawls 316A-316C and one or more springs such as springs 366. It will be appreciated that in other embodiments the one or more lugs can comprise any number of lugs, the one or more windows can comprise any number of windows, the one or more pawls can comprise any number of pawls, and the one or more springs can comprise any number of springs.

The reducer body 322 can comprise a ring portion 368, one or more legs such as legs 370A and 370B, a socket 374, one or more lever tracks such as lever tracks 376A and 376B, one or more springs such as springs 378 and one or more pins such as pins 380. The legs 370A and 370B can comprise one or more pin holes such as pin holes 382A and 382B and one or more lock holes such as lock holes 384A and 384B, respectively. It will be appreciated that in other embodiments the one or more lever tracks can comprise any number of lever tracks, the one or more springs can comprise any number of springs, the one or more pins can comprise any number of pins, the one or more pin holes can comprise any number of pin holes, and the one or more lock holes can comprise any number of lock holes.

The lugs 354 can be coupled in a mating fashion with a socket 480 (shown in FIG. 46) in the palm handle 304. The pawls 316A-316C can be positioned in the windows 362A-362C and the springs 366 or other resilient members can be positioned between the pawls 316A-316C and the backstops 396 (shown in FIG. 31) to bias the pawls 316A-316C to a retracted position away from a center axis CA (shown in FIG. 28) of the clutch housing 319. The clutch knob 318 can be positioned over the cylinder portion 360 to the retain pawls 316A-316C therein. The washer 320 can be positioned around the threaded end 364 to provide a bearing between the clutch housing 319 and the reducer body 322. The threaded end 364 can be inserted into the socket 374 and the fastener 352 can be used to secure clutch the housing 319 to the reducer body 322 via a threaded engagement. The clutch housing 319 and the reducer body 322 can rotate relative to each other about the center axis CA of the reducer 300. The upper release levers 324A and 324B and the lower release levers 326A and 326B can be attached to the lever tracks 376A and 376B, respectively, via the pins 380. Thus, each of the upper release levers 324A and 324B and the lower release levers 326A and 326B can be pivotable about one of the pins 380 to move the rockers 466 in and out of the lock holes 384A and 384B, respectively. The springs 378 (or other resilient members) can be used to bias the upper release levers 324A and 324B away from the center axis of the reducer body 322. As explained with reference to FIGS. 47-49, the upper release levers 324A and 324B and the lower release levers 326A and 326B can be configured to interact, respectively, to provide three different levels of functionality to the rockers 466.

FIG. 29 is a perspective view of the reducer body 322 of the reducer assembly 304 of FIG. 28. FIG. 30 is a cross-sectional view of the reducer body 322 of FIG. 29. FIGS. 28 and 29 are discussed concurrently. The reducer body 322 can comprise the ring portion 368, the legs 370A and 370B, the socket 374, the lever tracks 376A and 376B, the pin holes 382A and 382B and the lock holes 384A and 384B, as discussed previously. The reducer body 322 can further comprise an end flange 386, one or more side surfaces such as side surfaces 388A and 388B, one or more bores such as bores 390A and 390B and bores 392A and 392B. It will be appreciated that in other embodiments the one or more side surfaces can comprise any number of side surfaces and the one or more bores can comprise any number of bores.

The reducer body 322 can comprise a platform upon which other components of the reducer 300 can be mounted or coupled. The threaded end 364 (shown in FIG. 31) of the clutch housing 319 (shown in FIG. 31) can be inserted into the socket 374 and can be attached thereto using the fastener 352 (shown in FIG. 28). The fastener 352 can rest against the end flange 386. Thus, the tower body 12 (shown in FIG. 1) can be inserted into the space between the legs 370A and 370B to allow for coupling of the tower body 12 to the reducer body 322. The ring 30 (shown in FIG. 1) can rest against the fastener 352, as shown in FIGS. 47-49. The side surfaces 388A and 388B of the legs 370A and 370B that face each other can be curved to match the curvature of tower body 12. The outer surfaces 373A and 373B of the legs 370A and 370B facing away from the central axis CA can be ergonomically contoured. For example, the legs 370A and 370B can include one or more protrusions such as protrusions 375A and 375B that can be used by a user to push against the reducer 300 with fingers, etc. It will be appreciated that in other embodiments the one or more protrusions can comprise any number of protrusions.

The upper and lower release levers 324A, 324B, 326A, 326B can be seated in the lever tracks 376A and 376B, respectively, to allow the rockers 466 (shown in FIG. 45) to penetrate the lock holes 384A and 384B. The pin holes 382A can receive the pins 380 to couple the upper release lever 324A to the lever track 376A and the pin holes 382B can receive the pins 380 to couple the upper release lever 324B to the lever track 376B. The bores 390A and 390B and the bores 392A and 392B can facilitate cleaning of the reducer body 322, such as by eliminating dead air space to allow cleaning and sterilizing material, e.g., steam, to reach spaces within the reducer body 322.

Figure 32:
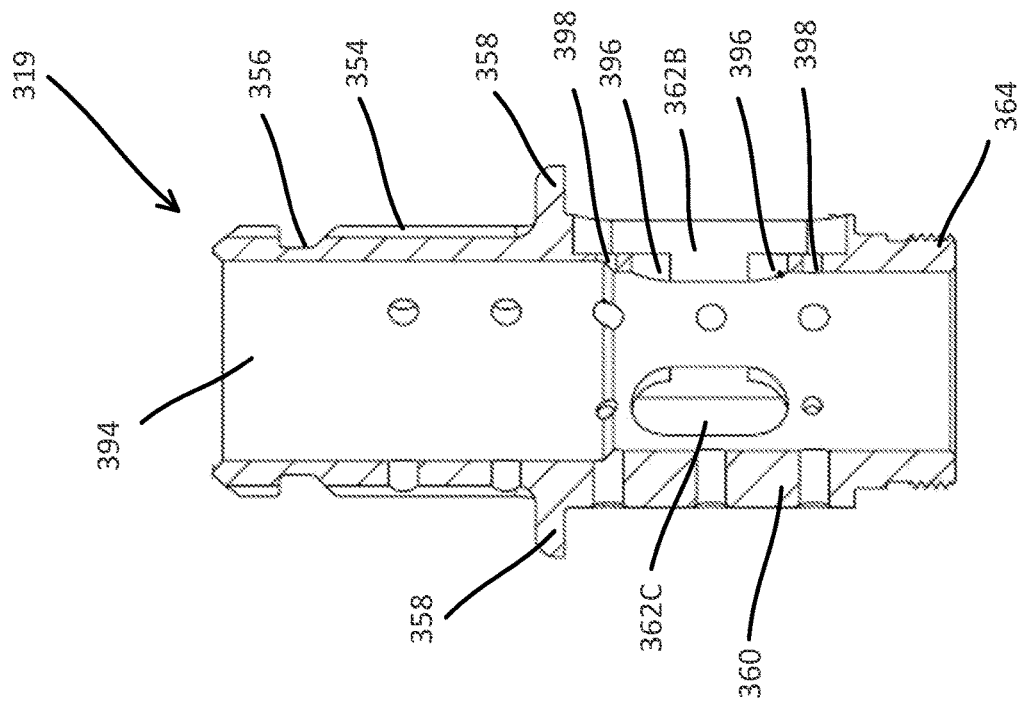
FIG. 32 is a cross-sectional view of the clutch housing of FIG. 31 according to at least one embodiment of the present disclosure.
Figure 31:
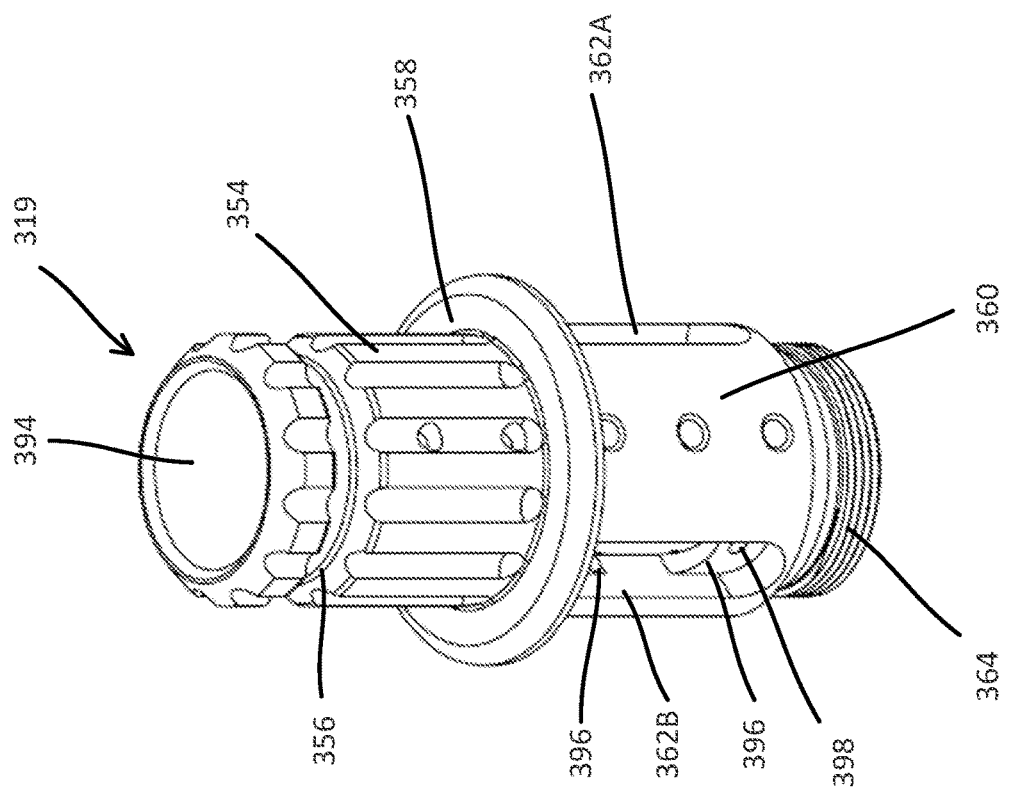
FIG. 31 is a perspective view of a clutch housing of the reducer assembly of FIG. 28 according to at least one embodiment of the present disclosure.

FIG. 31 is a perspective view of the clutch housing 319 of the reducer assembly 304 of FIG. 28. FIG. 32 is a cross-sectional view of the clutch housing 319 of FIG. 31. FIGS. 31 and 32 are discussed concurrently. The clutch housing 319 can comprise the lugs 354, the channel 356, the flange 358, the cylinder portion 360, the windows 362A-362C and the threaded end 364. The clutch housing 319 can further comprise a channel 394, one or more backstops such as backstops 396 and one or more bores such as bores 398. It will be appreciated that in other embodiments the one or more backstops can comprise any number of backstops and the one or more bores can comprise any number of bores. The clutch housing 319 can additionally include other bores to facilitate cleaning of the clutch housing 319, such as by eliminating dead air space to allow cleaning and sterilizing material, e.g., steam, to reach spaces within the clutch housing 319.

The threaded end 364 can include external threading configured to mate with internal threading on the fastener 352. The threaded end 364 can be sized to fit into the socket 374 (shown in FIG. 30) of the reducer body 322.

The cylinder portion 360 can engage the ring portion 368 (shown in FIG. 30) of the reducer body 322. The cylinder portion 360 can be sized to fit within the clutch knob 318. The clutch knob 318 can rest against the flange 358. The flange 358 can have an outer diameter that is approximately the same size as the outer diameter of the clutch knob 318.

Figure 41:
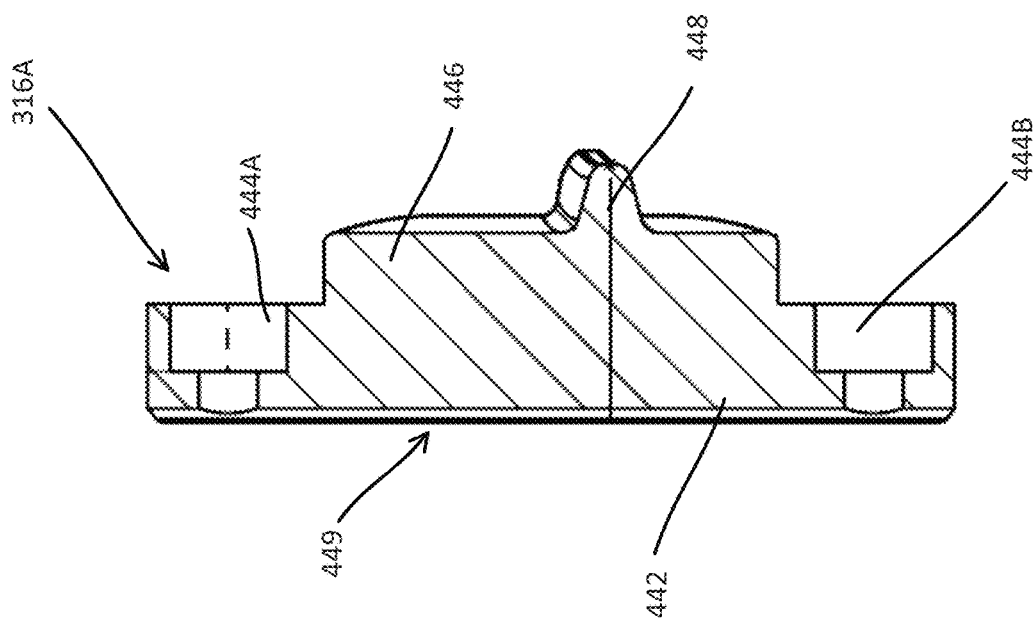
FIG. 41 is a cross-sectional view of the pawl of FIG. 40 according to at least one embodiment of the present disclosure.
Figure 40:
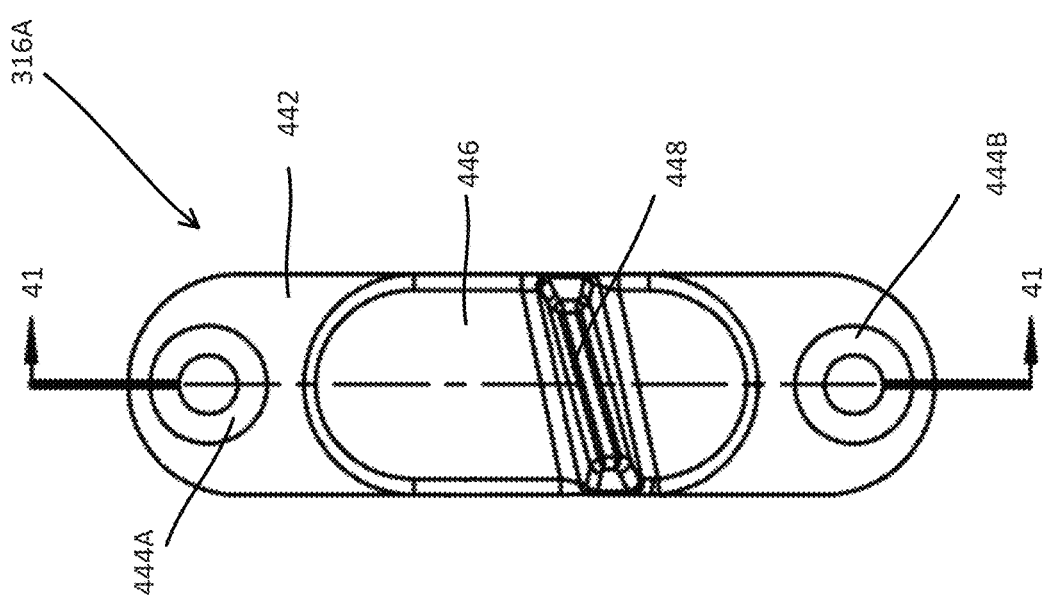
FIG. 40 is a front view of a pawl for the clutch mechanism of FIG. 27 according to at least one embodiment of the present disclosure.

The windows 362A-362C can be sized to receive the pawls 316A-316C (shown in FIGS. 40 and 41). The windows 362A-362C can be equally spaced about the perimeter of the cylinder portion 360 such that the pawls will push the reducing shaft 306 toward the center axis CA. The outer perimeter shape of the pawls 316A-316C can be sized to mate with the outer shape of the windows 362A-362C. The backstops 396 can be positioned at ends of the windows 362A-362C to prevent the pawls 316A-316C from passing through the windows 362A-362C. The backstops 396 can additionally be used as surfaces for which the springs 366 (shown on FIG. 28) can push off. The bores 398 can receive the springs 366 to prevent separation of the springs 366 from the reducer assembly 304. The bores 398 can align with the bores 444A and 444B in the pawls 316A-316C (shown in FIGS. 40 and 41).

The lugs 354 can be formed in the cylinder portion 360 on an opposite side of the flange 358 as the windows 362A-362C. The lugs 354 and the cylinder portion 360 can be sized to fit within the socket 480 (shown in FIG. 46) of the palm handle 302. The lugs 354 can form grooves therebetween to provide rotational grips to a user of the reducer 300 when the palm handle 302 is removed. In additional examples, the socket 520 (shown in FIG. 25 or 46) of the palm handle 302 can include the mating lugs 522A-522C to fit between the lugs 354 to prevent relative rotation between the palm handle 302 and the clutch housing 319. The channel 356 can extend around the cylinder portion 360 across the lugs 354. The tang 502 of the button 315 (shown in FIG. 46) can be positioned within the channel 356 to allow the palm handle 302 to be axially restrained on the clutch housing 319.

FIG. 33 is a first side view of the reducing shaft 306 of FIGS. 24-26. FIG. 34 is a second side view of the reducing shaft 306 of FIGS. 24-26. FIG. 35 is an end view of the reducing shaft 306 of FIGS. 24-26 from a proximal position looking distally. FIGS. 33-35 are discussed concurrently. The reducing shaft 306 can comprise the shaft body 328, the threaded shaft portion 330, the first rail 332A, the second rail 332B, an end 400, one or more windows such as windows 402, a bracket 404, and a drive seat 406.

The shaft body 328 can comprise an elongate, cannulated body that extends from the end 400 to the drive seat 406. The end 400 can comprise a circular land or projection that can receive the ring 344 (shown in FIG. 25). In additional examples, the end 400 can be threaded to receive mating threading on the ring 344 (shown in FIG. 26). The drive seat 406 can comprise arcuate surfaces at the ends of the rails 332A and 332B that are shaped to abut a circular stabilization member, such as an elongate rod 522 (shown in FIG. 54) that, in some examples, may be rigid. The threaded shaft portion 330 can extend from the end 400 along a length and can comprise external threading for engaging mating threading of the pawls 316A-316C (shown in FIG. 28). The shaft body 328 can comprise a cylindrical body configured to fit within the opening 58 (shown in FIG. 4) between the extenders 20A and 20B of the tower body 12. The rails 332A and 332B can extend along opposite sides of the shaft body 328 and can extend beyond the cylindrical portion of the shaft body 328. The rails 332A and 332B can comprise elongate protrusions configured to fit within the lobes 112B and 112D of the threaded end 19 (shown in FIG. 11) on the tower 10. The windows 402 can extend along the shaft body 328 between the rails 332A and 332B. The windows 402 can allow for passage of cleaning material, e.g., steam, into the interior of the shaft body 328. The bracket 404 can be located between the rails 332A and 332B and can include a socket or bore through which the driver 308 can extend. The bracket 404 can provide alignment of the driver 308 centrally between the rails 332A and 332B to facilitate insertion of the driver tip 340 with a housing of a pedicle screw.

FIG. 36 is a perspective view of the clutch knob 318 of the reducer assembly 304 of FIG. 27. FIG. 37 is a cross-sectional view of the clutch knob 318 of FIG. 36. FIGS. 36 and 37 are discussed concurrently. The clutch knob 318 can comprise an annular body 410, a passage 412, one or more ramps such as ramps 414A, 414B and 414C, one or more bumps such as bumps 415A, 415B and 415C, bumps 416A, 416B and 416C, one or more pads such as pads 418A, 418B and 418C, a flange 420 and one or more bores such as bores 422. It will be appreciated that in other embodiments the one or more ramps can comprise any number of ramps, the one or more bumps can comprise any number of bumps, the one or more pads can comprise any number of pads, and the one or more bores can comprise any number of bores.

Figure 50:
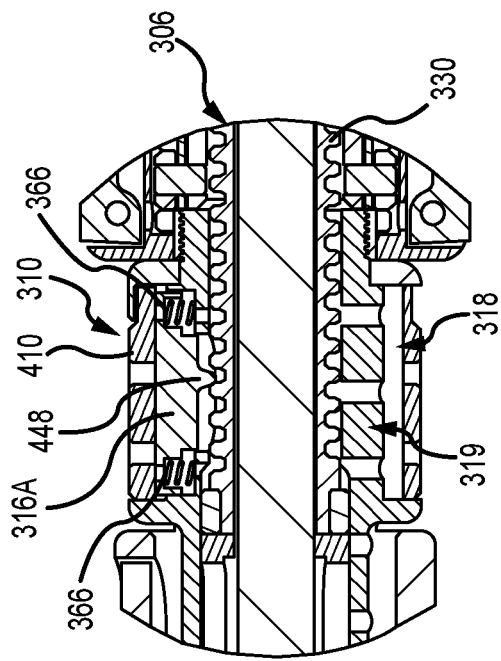
FIG. 50 is a close-up longitudinal cross-sectional view of the clutch mechanism of FIG. 24A in an unlocked state according to at least one embodiment of the present disclosure.
Figure 52:
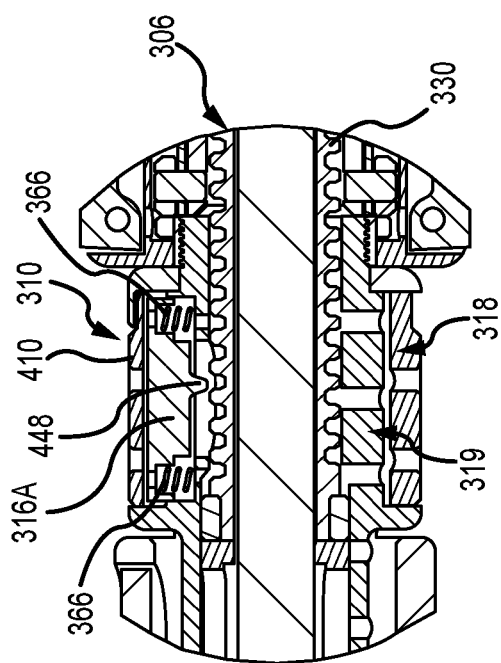
FIG. 52 is a close-up longitudinal cross-sectional view of the clutch mechanism of FIG. 24A in a locked state according to at least one embodiment of the present disclosure.
Figure 51:
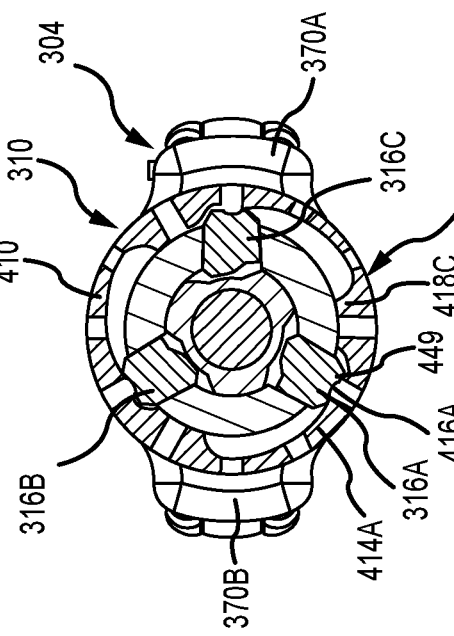
FIG. 51 is a close-up axial cross-sectional view of the clutch mechanism of FIG. 24A in an unlocked state according to at least one embodiment of the present disclosure.
Figure 53:
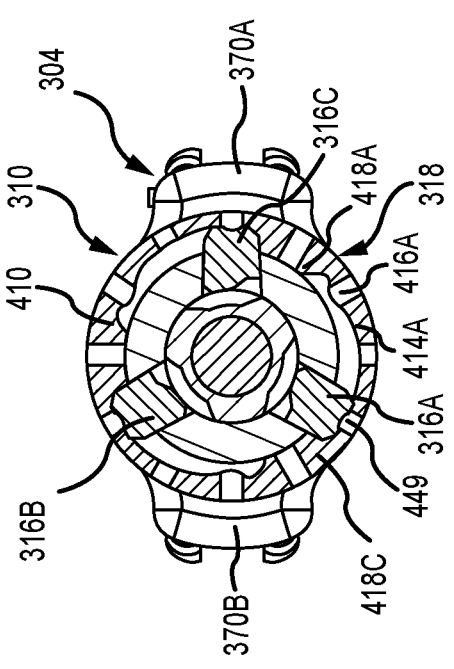
FIG. 53 is a close-up axial cross-sectional view of the clutch mechanism of FIG. 24A in a locked state according to at least one embodiment of the present disclosure.

The annular body 410 can be sized to circumscribe the clutch housing 319. The annular body 410 can comprise a user control configured to engage and disengage the reducer assembly 304 with the reducing shaft 306 by controlling a positioning of the pawls 316A-316C. The inner diameter surfaces of the annular body 410 can comprise inner tracks for engaging the pawls 316A-316C. Specifically, the ramps 414A-414C can be configured to provide the annular body 410 with varying levels of thickness relative to the central axis CA that can be used to push the pawls 316A-316C further into the windows 362A-362C as the clutch knob 318 is rotated by a user. The pads 418A-418C can comprise arcuate surfaces configured to ride against the cylinder portion 360 of the clutch housing 319 in portions between the windows 362A-362C. The pads 418A-418C can maintain the clutch knob 318 centered on the clutch housing 319. Exterior-facing surfaces of the pawls 316A-316C can ride against the ramps 414A-414C. The bumps 415A-415C can comprise projections or protrusions at the thinner ends of the ramps 414A-414C to hold the pawls 316A-316C in positions where the pawls 316A-316C are disengaged with threading of the threaded shaft portion 330 (note, the bumps 415A-415C are omitted from FIGS. 50 and 51). The bumps 416A-416C can comprise projections or protrusions at the thicker ends of the ramps 414A-414C to hold the pawls 316A-316C in positions where the pawls 316A-316C are engaged with threading of the threaded shaft portion 330, as can be seen in FIGS. 52 and 53. As such, the reducing shaft 306 can be moved in the axial direction within the clutch mechanism 304 via rotation of the clutch housing 319. From the engaged position, the clutch knob 318 can be rotated clock-wise (relative to the orientation of FIG. 37) to move the thinner portions of the ramps 414A-414C to engage the pawls 316A-316C. As such, the springs 366 can push against the backstops 396 to push the pawls 316A-316C away from the threaded shaft portion 330, as can be seen in FIGS. 50 and 51. As such, the reducing shaft 306 can be freely moved in the axial direction within the clutch housing 319. The ramps 414A-414C can extend over approximately less than 25% of the clutch knob 318 between the bumps 416A-416C and the pads 418A-418C such that the pawls 316A-316C can go from being fully withdrawn from the reducing shaft 306 to fully engaged with the reducing shaft 306 in a quarter turn of the clutch knob 318 or less. The the flange 420 can seat within clutch washer 320 (shown in FIG. 25). The bores 422 can allow for can allow for passage of cleaning material, e.g., steam, into the interior of the clutch knob 318.

FIG. 38 is a side view of the plunger 342 for a closure top starter of the driver 308 of FIG. 26. FIG. 39 is a cross-sectional view of the plunger 342 of FIG. 38. FIGS. 38 and 39 are discussed concurrently. The plunger 342 can comprise a cylindrical body 430, a passage 432, one or more slots such as slots 350, one or more bores such as bores 434 and a rim 436.

The plunger 342 can comprise a body that attaches to the actuation portion 336 of the driver 308 to control relative axial location of the driver 308 to the reducing shaft 306. The pin 504 can be fixedly attached to the plunger 342, but the driver 308 can move relative to the pin 504 via the slots 348. Thus, the driver 308 will advance distally with the reducing shaft 306 under the power of the pawls 316A-316C. However, once full reduction has been achieved, the driver 308 can be advanced further under manual axial power via a compression of the spring 508 (shown in FIG. 46) such as by the application of axial force from a driver inserted into the socket 510 (shown in FIG. 46).

The internal passage 432 can be sized to receive the actuation portion 336 of the driver 308 (shown in FIG. 26), while the rim 436 can be sized to receive the shaft 338. The end surface 506 (shown in FIG. 46) of the actuation portion 336 can abut the rim 436 when the driver 308 is in the fully extended position. The bores 434 can be sized to receive the pin 504 (shown in FIG. 46). The spring 508 (shown in FIG.

Figure 46:
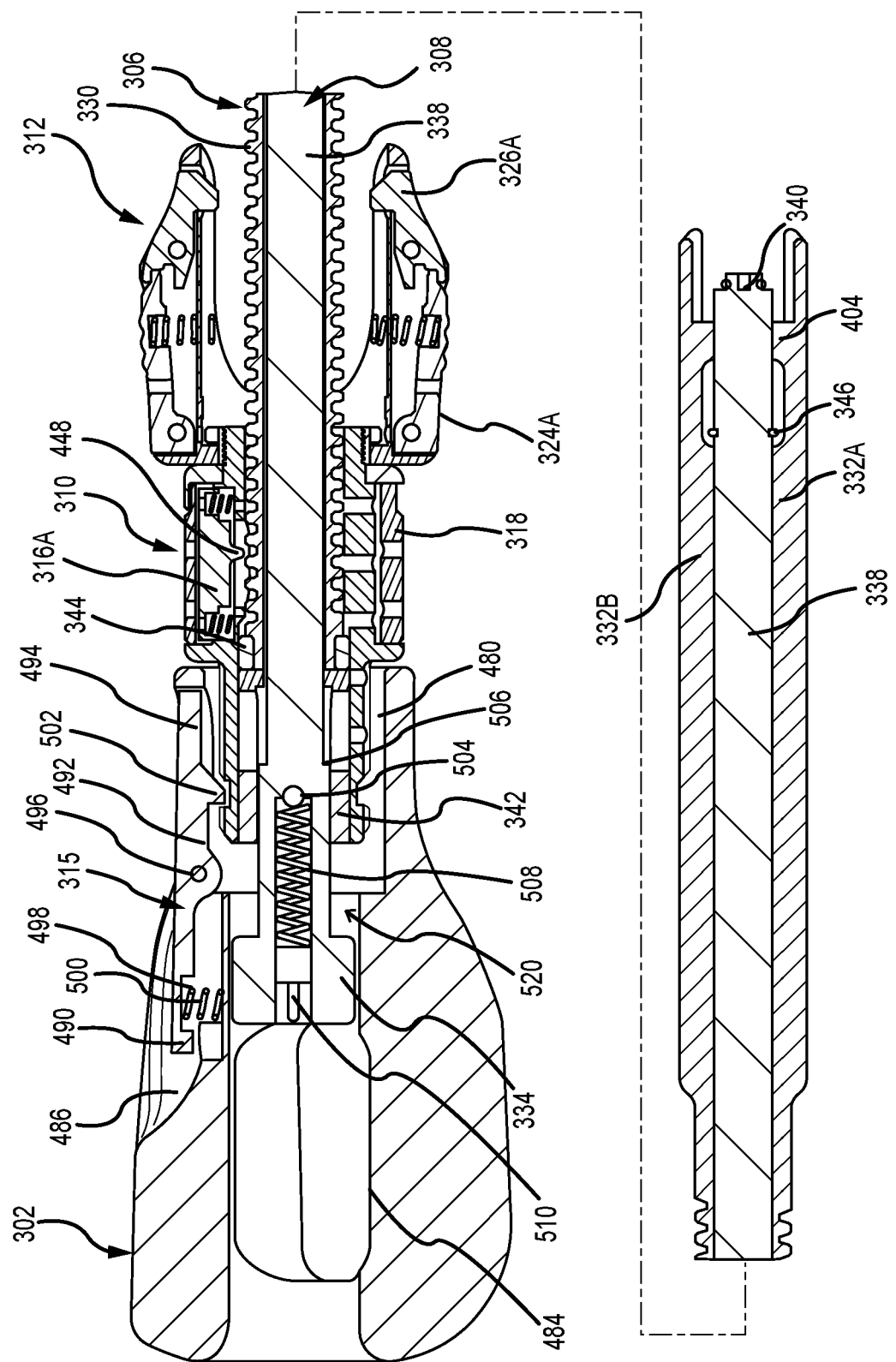
FIG. 46 is a cross-sectional view of the reducer of FIG. 24A showing a clutch mechanism, a locking mechanism and a driver mechanism according to at least one embodiment of the present disclosure.

46) can be positioned against the pin 504 to bias the driver 308 in a proximal direction (e.g., to the left relative to FIG. 46). The windows 350 can comprise elongate openings through the cylindrical body 430 to allow for visibility of the driver 308 therein.

With reference to FIG. 46, before a reduction operation, the driver 308 can be advanced by compressing the spring 508 to expose the tip 340 to grab a closure mechanism, e.g., a set screw. The spring 508 can be released such that the tip 340 and the closure mechanism are retracted between the rails 332A and 332B. Thereafter, a reduction procedure can be conducted to reduce a stabilization element with the reducing shaft 306. Once the stabilization element is positioned within the pedicle screw housing, the driver 308 can again be manually advanced to compress the spring 508 to engage the closure mechanism with the pedicle screw housing. Torque can be applied to the driver 308 via the socket 510 to advance the closure mechanism into the pedicle screw housing.

FIG. 40 is a front view of the pawl 316A for the clutch mechanism 319 of FIG. 27. FIG. 41 is a cross-sectional view of the pawl 316A of FIG. 40. FIGS. 40 and 41 are discussed concurrently. The pawl 316A can comprise a body 442, one or more sockets such as sockets 444A and 444B, a guide 446 and a thread 448. The pawls 316B and 316C (FIG. 28) can be configured similarly as the pawl 316A. It will be appreciated that in other embodiments the one or more sockets can comprise any number of sockets.

The pawl 316A can be configured to keep the thread 448 properly oriented for engagement with threading of the threaded shaft portion 330. Thus, the body 442 of the pawl 316A can be elongated in the axial direction of the reducer 300 and the tower 10 to prevent rotational misalignment (relative to the orientation of FIG. 40) of the thread 448. Likewise, the body 442 can have a thickness to maintain engagement with the window 362A in the clutch housing 319 (shown in FIG. 28) and prevent radial misalignment relative to the central axis of the reducer 300. The body 442 can maintain engagement with the window 362A regardless of the position of the pawl 316A controlled by the clutch knob 318. The body 442 can include a depression 449 (shown in FIGS. 51 and 53) to allow for engagement with the protrusions 416A-416C and/or the protrusions 415A-415C (shown in FIG. 37). The guide 446 can have a thickness sufficient to extend the thread 448 into engagement with the threaded shaft portion 330 when in the extended position and to fully disengage the thread 448 from the threaded shaft portion 330 in the retracted position. The guide 446 is axially shorter than the body 442 to allow space for the sockets 444A and 444B to allow the pawl 316A to engage with the springs 366 (shown in FIG. 28). The sockets 444A and 444B can comprise bores into the body 442 to receive the springs 366 and maintain the springs 366 in engagement with the pawl 316A. The thread 448 can comprise a segment of threading configured to mate with the threaded shaft portion 330. The thread 448 can have sufficient thickness and a pitch to engage with threading on the threaded shaft portion 330.

Figure 43:
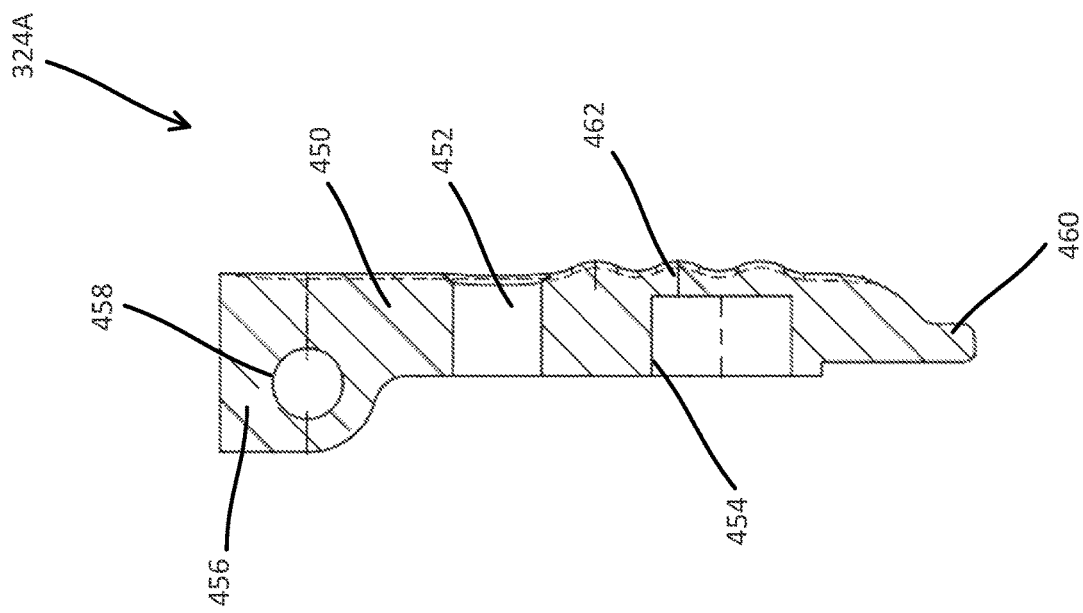
FIG. 43 is a cross-sectional view of the upper release lever of FIG. 42 according to at least one embodiment of the present disclosure.
Figure 42:
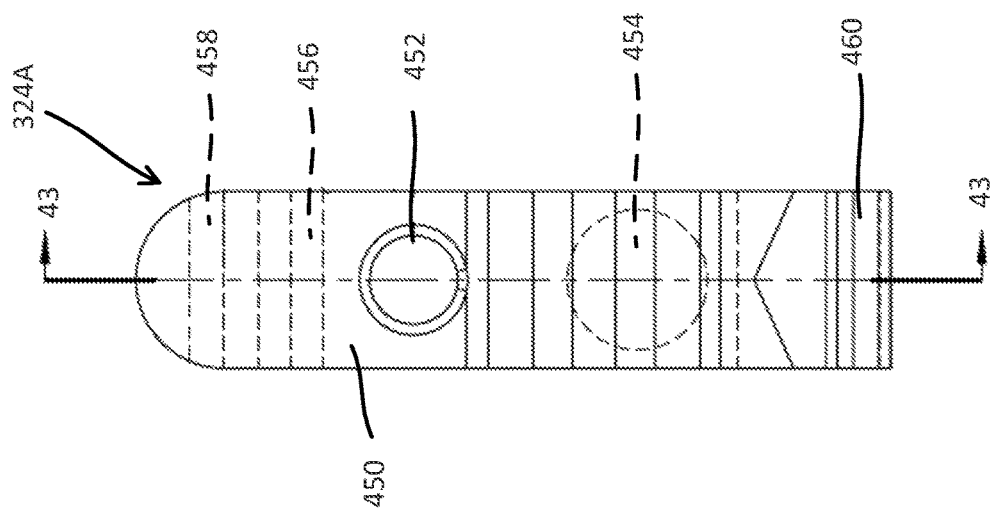
FIG. 42 is a front view of an upper release lever for the locking mechanism of FIG. 27 according to at least one embodiment of the present disclosure.

FIG. 42 is a front view of the upper release lever 324A for the locking mechanism 312 of FIG. 27. FIG. 43 is a cross-sectional view of the upper release lever 324A of FIG. 42. FIGS. 42 and 43 are discussed concurrently. The upper release lever 324A can comprise a body 450, a bore 452, a socket 454, a hinge 456, a pivot bore 458, a tooth 460 and one or more undulations 462. It will be appreciated that in other embodiments the one or more undulations can comprise any number of undulations. The upper release lever 324B can be configured similarly as the upper release lever 324A.

The body 450 can extend from a first end at the pivot bore 458 to a second end at the tooth 460. The first end can be thickened to allow for the pivot bore 458. The body 450 can extend from the first end toward one side of the pivot bore 458 to allow the tooth 460 space to pivot. The bore 452 can be located in a middle portion of the body 450 and can comprise a through-bore configured to extend from an exterior surface of the upper release lever 324A to an interior surface of the upper release lever 324A. The socket 454 can be located in a middle portion of the body 450 and can comprise a blind end bore configured to receive the spring 378 (shown in FIG. 28). The socket 454 can be located away from the pivot bore 458 to provide rotational force or torque about the pivot bore 458. The tooth 460 can extend axially from the second end of the body 450 in a direction transverse to the pivot axis. The tooth 460 can extend in line with the axis of the body 450 (shown in FIG. 48) and can thus project parallel to the center axis CA of the reducer 300 when the reducer body 322 is aligned with the axis, but the tooth 460 can be projected toward the reducer body 322 (shown in FIG. 49) or away from reducer body 322 (shown in FIG. 47) as the body 450 is pivoted at the pivot bore 458. As such, the tooth 460 can be pivoted into three different positions to engage with the lower release lever 326A.

Figure 45:
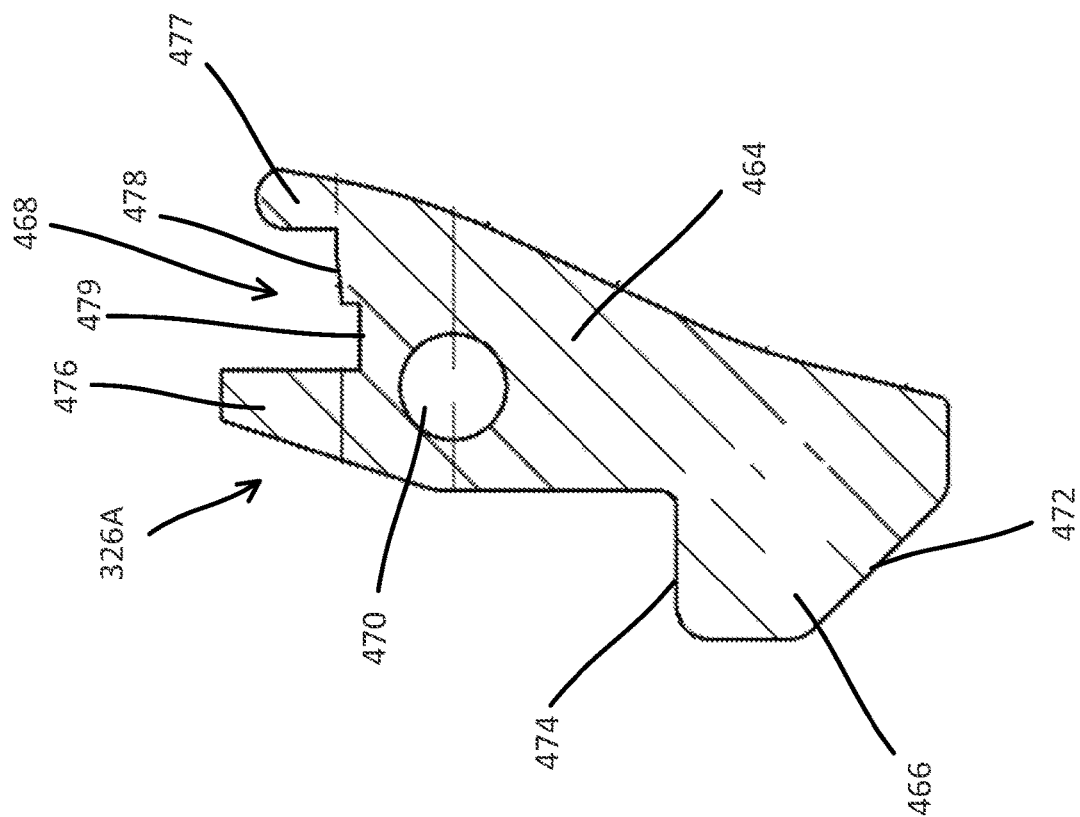
FIG. 45 is a cross-sectional view of the lower release lever of FIG. 44 according to at least one embodiment of the present disclosure.
Figure 44:
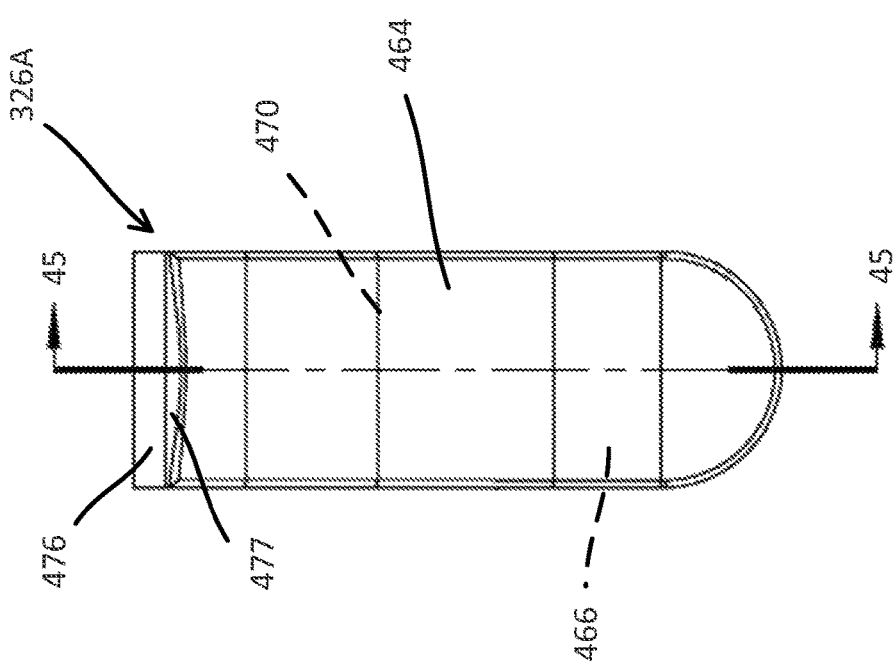
FIG. 44 is a front view of a lower release lever for the locking mechanism of FIG. 27 according to at least one embodiment of the present disclosure.

FIG. 44 is a front view of the lower release lever 326A for the locking mechanism 312 of FIG. 27. FIG. 45 is a cross-sectional view of the lower release lever 326A of FIG. 44. FIGS. 44 and 45 are discussed concurrently. The lower release lever 326A can comprise a body 464, a rocker 466, a socket 468 and a pivot bore 470. The lower release lever 326B can be configured similarly as the lower release lever 326A.

The body 464 can extend from a first end at the rocker 466 to a second end at the socket 468. The pivot bore 470 can be located in a central or middle portion of the body 464 to allow the rocker 466 and the socket 468 to each move closer to and further away from the reducer body 322 (shown in FIG. 27). The rocker 466 can comprise a tooth or projection that can extend through the lock hole 384A (shown in FIG. 30) to engage the tower body 12 (shown in FIG. 1). The distal or leading end 472 of the rocker 466 can comprise a planar surface angled or slanted relative to the center axis CA of the reducer 300 to allow the reducer 300 to be axially pushed down onto the tower body 12. However, the proximal or trailing end 474 of the rocker 466 can comprise a planar surface orthogonal to the center axis CA of the reducer 300 to inhibit or prevent axially movement of the reducer 300 up from the tower body 12.

The socket 468 can comprise a first flange 476, a second flange 477, a trough 478 and a channel 479. The first flange 476 can have an angled outer surface to facilitate the first flange 476 lying flush with the lever track 376A (shown in FIG. 28) when the lower release lever 326A is rotated (shown in FIG. 49). The second flange 477 can be rounded to facilitate rotation against surfaces of the upper release lever 324A (see FIGS. 47 and 49). The first flange 476 and second flange 477 can form inner and outer surfaces for engaging inner and outer surfaces of the tooth 460 of the upper release lever 324A in the radial direction relative to the center axis CA of the reducer 300. The trough 478 and the channel 479 can comprise axial surfaces for engaging the distal tip of the tooth 460. Thus, depending on the rotational positions of the upper release lever 324A and the lower release lever 326A, the tooth 460 can engage the second flange 477 and the trough 478 (shown in FIG. 47), the first flange 476 (shown in FIG. 48) or the first flange 476 and the channel 479 (shown in FIG. 49).

FIG. 46 is a cross-sectional view of the reducer 300 of FIG. 24A showing the clutch mechanism 310, the locking mechanism 312 and the driver 308. The reducer 300 can be connected to the palm handle 302. The palm handle 302 can comprise the socket 480, the driver channel 482, the windows 484 and the button seat 486, as previously described. The button 315 can be positioned in the button seat 486 and can comprise the first end 490, the pivot 492 and the second end 494. The button 315 can comprise an elongate body configured to rotate at the pivot 492 such as via coupling of the button 315 to the palm handle 302 via the pin 496. The first end 490 can include the bore 498 against which the spring 500 or another biasing element can be positioned to push against the button seat 486. The second end 494 can include the tang 502 for engaging the clutch housing 319 (shown in FIGS. 31 and 32). The socket 510 can be located in the knob 334 of the driver 308 to receive a tool such as, for example, a torque wrench to rotate the driver 308. The relative lengths of components of the reducer 300 can be selected such that alignment of various features can indicate that the reducing shaft 306 has reached full reduction. For example, the proximal end of the knob 334 can align with the bottom of the windows 484 when r the educing shaft 306 is fully extended and the driver 308 is retracted, which can be seen through the windows 484 when the palm handle 302 is attached. Additionally, the proximal end of the plunger 342 can align with the proximal end of the clutch housing 319 when the reducing shaft 306 is fully extended, which can be seen when the palm handle 302 is removed.

Figure 47:
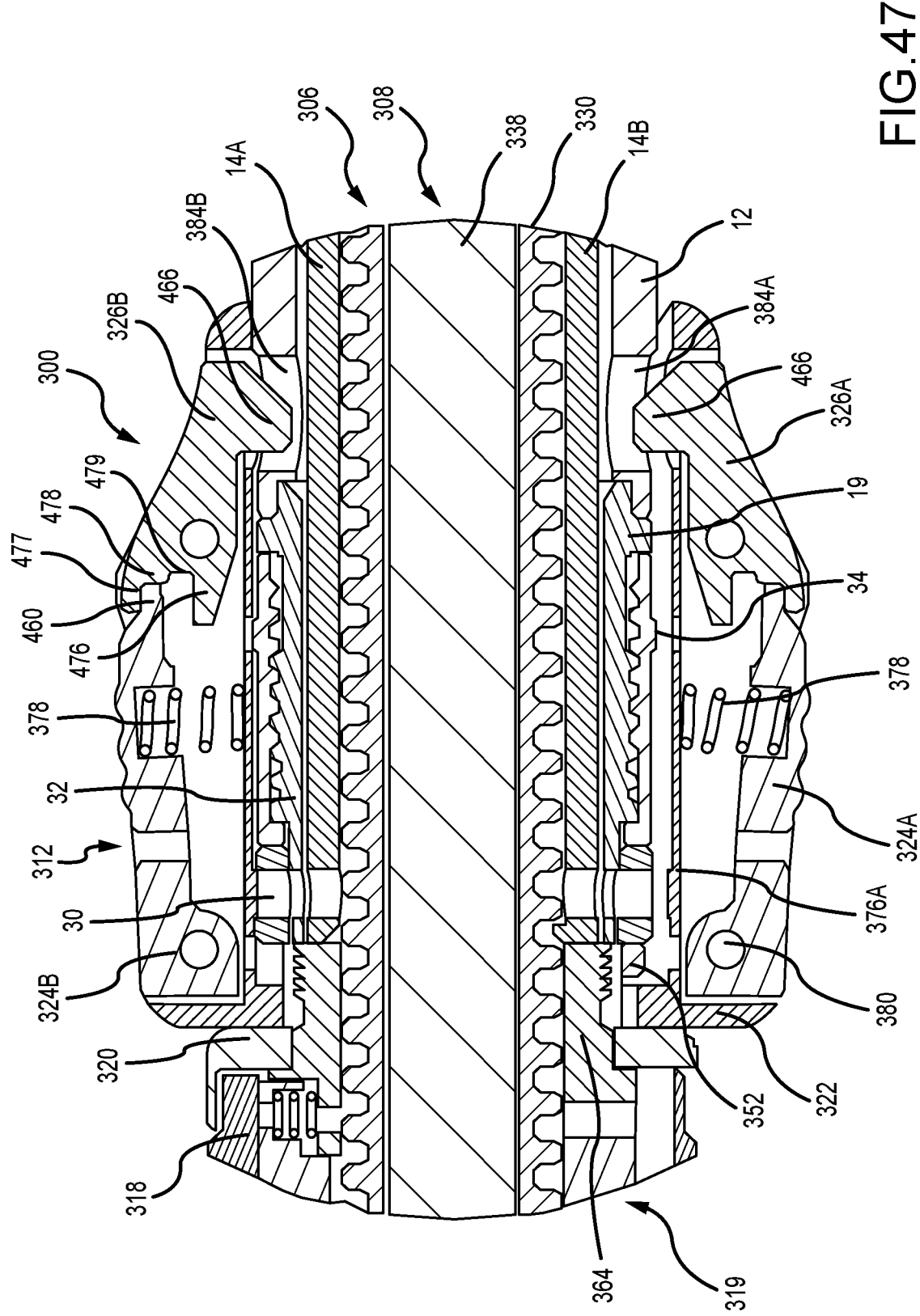
FIG. 47 is a close-up longitudinal cross-sectional view of the locking mechanism of FIG. 46 in a locked state according to at least one embodiment of the present disclosure.

FIG. 47 is a close-up cross-sectional view of the locking mechanism 312 of FIG. 46 in a locked state. In the locked state, the springs 378 can rotate the upper release levers 324A and 324B outward such that the teeth 460 rotate the lower release levers 326A and 326B outward. In such a configuration, the teeth 460 push against the outer flanges 477 and the trough 478. As such, the rockers 466 are constrained such that forces acting on the ends 472 and 474 (shown in FIG. 45) from the tower body 12 cannot change the relative position of the teeth 460 relative to the socket 468 (FIG. 45). Thus, the reducer body 322 cannot be moved axially along the tower 10 without pressing of the upper release levers 324A and 324B inward. Interaction of the upper release levers 324A and 324B and the lower release levers 326A and 326B in the locked position of FIG. 47 provides a robust coupling with the tower body 12 such that the reducer 300 will not be displaced from the tower 10 during operation of the reducer 300 without undue force.

Figure 48:
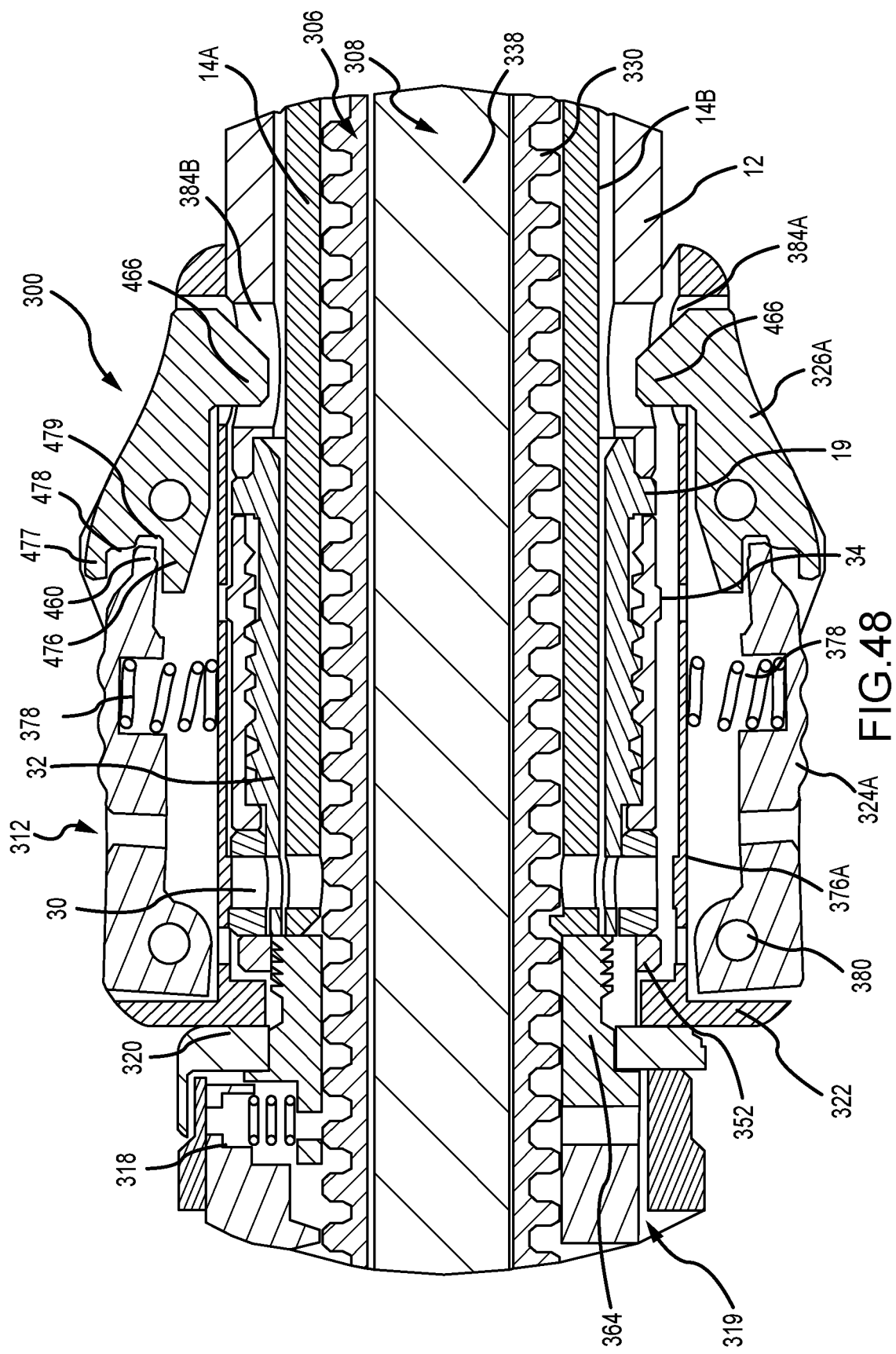
FIG. 48 is a close-up longitudinal cross-sectional view of the locking mechanism of FIG. 46 in an unlocked state according to at least one embodiment of the present disclosure.

FIG. 48 is a close-up cross-sectional view of the locking mechanism 312 of FIG. 46 in an unlocked state. In the unlocked state, the springs 378 can be pushed inward by application of force to the upper release levers 324A and 324B by a user. In the unlocked state, the springs 378 are partially compressed. As such, the teeth 460 can be moved to interact with the inner flange 476. As such, application of force to the end 474 (shown in FIG. 45) via the tower body 12 will not cause the rockers 466 to be displaced from the lock holes 384A and 384B such that the reducer 300 cannot be advanced proximally off the tower body 12. However, application of force to the end 472 via the tower body 12 will cause the rockers 466 to be displaced from the lock holes 384A and 384B such that the reducer 300 can be advanced distally into position on the tower body 12.

Figure 49:
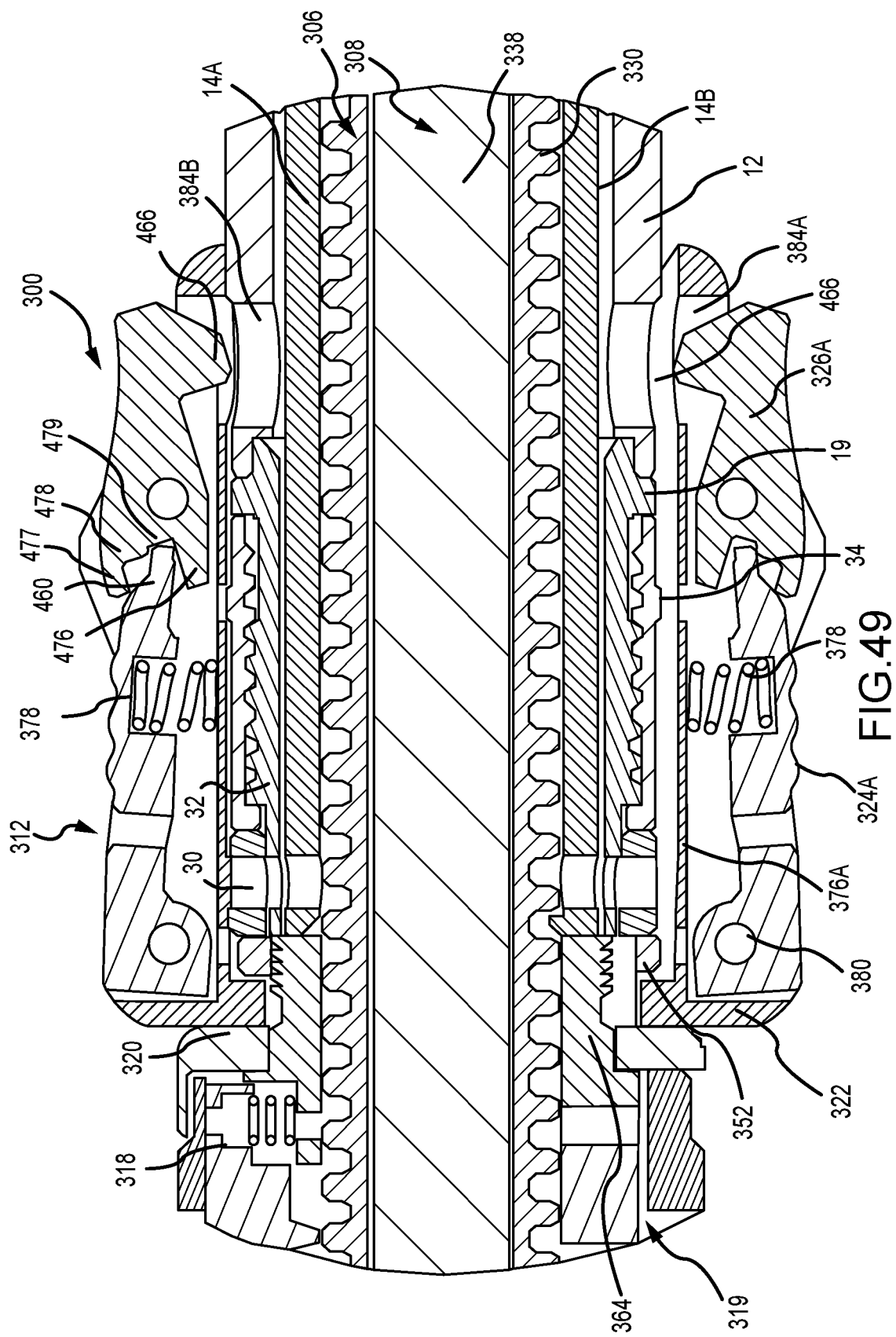
FIG. 49 is a close-up longitudinal cross-sectional view of the locking mechanism of FIG. 46 in an open state according to at least one embodiment of the present disclosure.

FIG. 49 is a close-up cross-sectional view of the locking mechanism 312 of FIG. 46 in an open state. In the open state, the springs 378 can be pushed inward by application of force to the upper release levers 324A and 324B by a user to fully compressed positions. As such, the teeth 460 can be moved to interact with the inner flange 476 and the channel 479. As such, the rockers 466 can be manually withdrawn from the lock holes 384A and 384B to allow the reducer 300 to be pulled proximally off the tower body 12.

FIG. 50 is a close-up cross-sectional view of the clutch mechanism 310 of FIG. 24A in an unlocked state. FIG. 51 is a close-up cross-sectional view of the clutch mechanism 310 of FIG. 24A in an unlocked state. FIGS. 50 and 51 are discussed concurrently.

The body 410 of clutch knob 318 can be rotated such that the thinner portion of the ramps 414A-414C and/or the protrusions 415A-415C are engaged with the pawls 316A-316C. As such, the springs 366 can push the pawls 316A-316C away from the threaded shaft portion 330, thereby also withdrawing the thread 448 from engagement with the threading of the threaded shaft portion 330. The reducing shaft 306 can therefore freely move in the axial direction within the clutch housing 319. As such, the reducer 300 can be quickly attached to the reducing shaft 306 in a position to begin reduction of a stabilization member without having to manually crank the clutch housing 319 to engage the stabilization member.

FIG. 52 is a close-up cross-sectional view of the clutch mechanism 310 of FIG. 24A in a locked state. FIG. 53 is a close-up cross-sectional view of the clutch mechanism 310 of FIG. 24A in a locked state. FIGS. 52 and 53 are discussed concurrently.

The body 410 of the clutch knob 318 can be rotated such that the thicker portion of the ramps 414A-414C and/or the protrusions 416A-416C are engaged with the pawls 316A-316C. As such, the clutch knob 318 can overcome the forces of the springs 366 to push the pawls 316A-316C into the threaded shaft portion 330, thereby also pushing the threads 448 into engagement with the threading of the threaded shaft portion 330. The reducing shaft 306 can therefore only move in the axial direction within the clutch housing 319 via rotation of the clutch housing 319. The clutch housing 319 can be rotated about the center axis CA of the reducer 300 to push the reducing shaft 306 and reduce the stabilization member.

Figure 54:
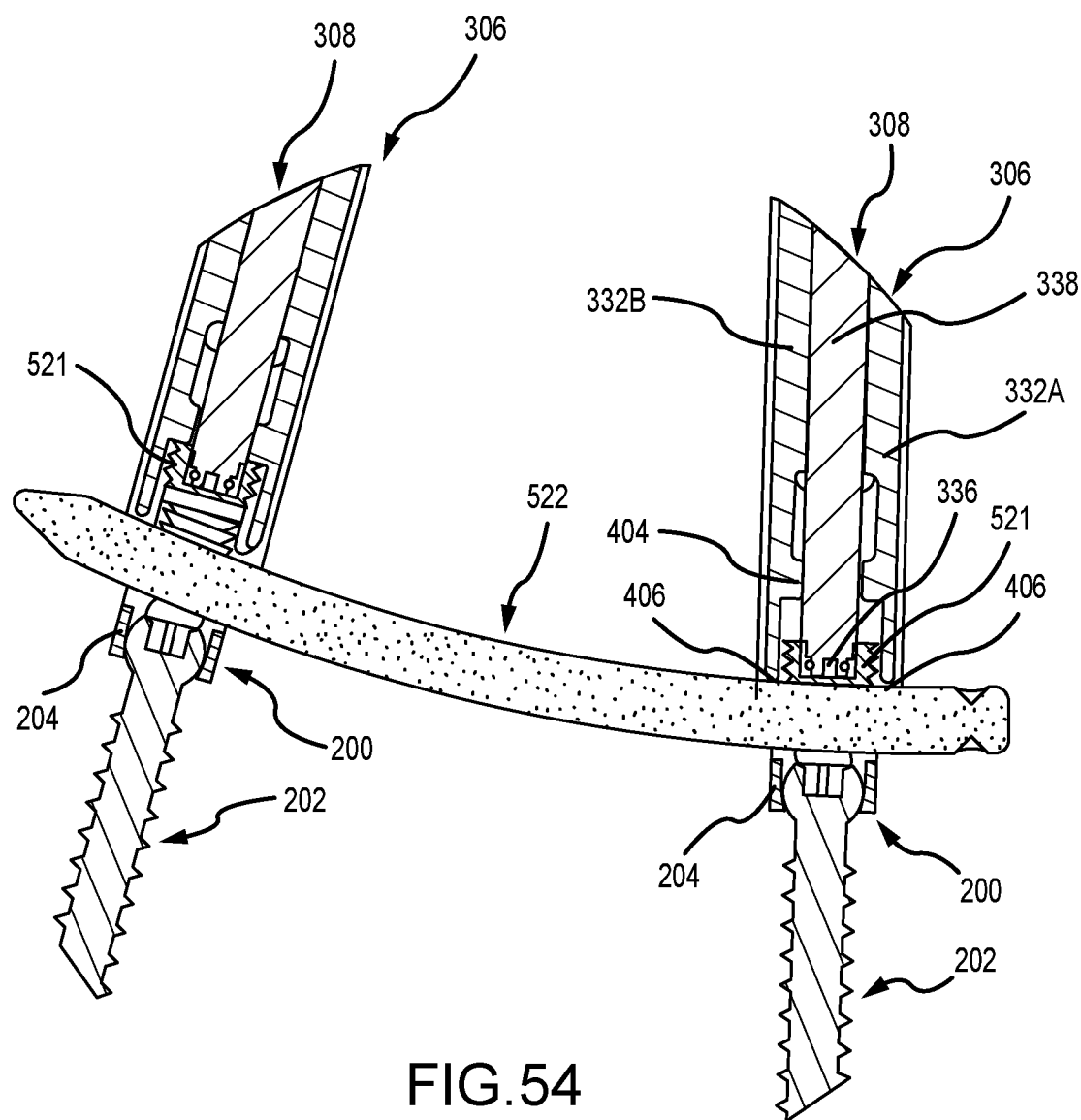
FIG. 54 is a cross-sectional view of a reducer mechanism of the present disclosure being used to attach a closure device to a pedicle screw housing using a driver and a reducing shaft according to at least one embodiment of the present disclosure.

FIG. 54 is a cross-sectional view of the reducer 300 of the present disclosure being used to attach the closure device 521 to the pedicle screw housing 204 having the rod 522 therein using the driver 308 and the reducing shaft 306.

The rails 332A and 332B of the reducing shaft 306 can be pushed distally or downward via the reducer 300 to push the rod 522 into the pedicle screw housing 204. For example, rotation of the clutch housing 319 relative to the reducer body 322 with the threads 448 engaged with the reducing shaft 306, can cause the drive seats 406 to extend further away from the reducer body 322 to provide reducing action. Additionally, the driver 308 can be advanced to push the closure device 521, e.g., a set screw, into engagement with the pedicle screw housing 204. The driver 308 can be rotated to cause the closure device 521 to rotate and engage threading within the pedicle screw housing 204 to lock the rod 522 into engagement with the pedicle screw housing 204. Thereafter, the tower 10 and the reducer 300 can be removed from the pedicle screw housing 204 and the rod 522 will remain seated in the housing 204 via the closure device 521.

The systems, devices and methods discussed in the present application can be useful in performing spinal surgical procedures using extenders for bone anchors or pedicle screws. The present disclosure describes extenders that provide easy and robust coupling to bone anchors or pedicle screws and facilitate minimally invasive implantation of a pedicle screw. The extenders are also capable of attaching axially to, for example, a pedicle screw without rotational motion between the pedicle screw tower and the pedicle screw. In other words, the pedicle screw tower may be pushed onto the pedicle screw to thereby releasably attach the pedicle screw tower to the pedicle screw. Additionally, the pedicle screw tower can attach radially around the pedicle screw. The present disclosure, for example, provides for extenders can include a plurality of pairs of deflectable members that attach to a bone anchor housing at different circumferential locations. A control knob can be set to allow the deflectable members to freely deflect, to lock the deflectable members to prevent deflection and to push the deflectable members radially outward. Further, the pedicle screw tower may be moved between a first position to lock onto a pedicle screw housing, a second position to allow deflectable arms deflectable prongs of the tower to slip onto a pedicle screw housing by deflecting, and a third position to push the deflectable arms and the deflectable prongs outward to release a pedicle screw housing via a knob.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

VARIOUS NOTES & EXAMPLES

Example 1 is an extender tower couplable to a bone anchor, the extender tower comprising: an outer tower body extending along a longitudinal axis from a proximal portion to a distal portion, the tower body comprising: first and second deflectable arms at the distal portion configured to engage with a housing of a bone anchor; first and second ramp-locks located on the first and second deflectable arms, respectively; and a threaded portion located at the proximal portion; a cap configured to engage the threaded portion; a first inner slide comprising a first coupling portion configured to engage the cap and a first window configured to engage the first ramp-lock; and a second inner slide comprising a second coupling portion configured to engage the cap and a second window configured to engage the second ramp-lock; wherein the cap can be rotated to: move the first and second inner slides to engage the first and second ramp-locks to push the first and second deflectable arms outward; and move the first and second inner slides to engage the first and second ramp-locks to prevent outward movement of the first and second deflectable arms.

In Example 2, the subject matter of Example 1 optionally includes wherein the outer tower body further comprises: first and second deflectable prongs extending alongside the first deflectable arm; and third and fourth deflectable prongs extending alongside the second deflectable arm.

In Example 3, the subject matter of Example 2 optionally includes wherein the first and second deflectable arms and the first through fourth deflectable prongs include features for engaging a housing of a fastener.

In Example 4, the subject matter of any one or more of Examples 2-3 optionally include wherein: the first inner slide includes first and second actuation features to push the first and second deflectable prongs outward; and the second inner slide includes third and fourth actuation features to push the third and fourth deflectable prongs outward.

In Example 5, the subject matter of Example 4 optionally includes wherein the first through fourth actuation features comprise pins configured to engage ramps of the first through fourth prongs.

In Example 6, the subject matter of any one or more of Examples 2-5 optionally include wherein: the first and second deflectable arms are configured to mate with closed faces of the bone anchor housing; and the first through fourth deflectable prongs are configured to mate with open faces of the bone anchor housing.

In Example 7, the subject matter of any one or more of Examples 1-6 optionally include wherein the tower body further comprises first and second rails extending axially alongside the first deflectable arm; and the first inner slide comprises first and second slots configured to receive the first and second rails.

In Example 8, the subject matter of Example 7 optionally includes wherein: the first and second rails comprise a plurality of intermittent rail segments; and the first and second slots comprises a plurality of intermittent slot segments.

In Example 9, the subject matter of Example 8 optionally includes wherein the plurality of intermittent rail segments and the plurality of intermittent slot segments are configured to, when engaged, permit axial sliding and prevent radial and circumferential displacement.

Example 10 is an extender tower for a bone anchor, the extender tower comprising: an outer tower body extending along a longitudinal axis, the tower body comprising: first and second deflectable arms disposed in opposing arrangement in a first radial direction; first and second deflectable prongs disposed in opposing arrangement in a second radial direction; a slide arrangement configured to slide within the outer tower body to engage the first and second deflectable arms and the first and second deflectable prongs; and a cap connected to the slide arrangement and configured to move axially relative to the outer tower body to move the slide arrangement; wherein the slide engagement is configured to engage the first and second deflectable arms and the first and second deflectable prongs in different axial positions including: a first axial position configured to radially interlock the slide arrangement with the first and second deflectable arms and the first and second deflectable prongs; a second axial position configured to allow the first and second deflectable arms and the first and second deflectable prongs to freely deflect; and a third axial position configured to push the first and second deflectable arms and the first and second deflectable prongs radially outward.

In Example 11, the subject matter of Example 10 optionally includes wherein the first and second deflectable arms are configured to deflect in a plane disposed orthogonal to a plane in which the first and second deflectable prongs are configured to deflect.

In Example 12, the subject matter of any one or more of Examples 10-11 optionally include third and fourth deflectable prongs.

In Example 13, the subject matter of any one or more of Examples 10-12 optionally include wherein the slide arrangement can comprise first and second inner slides having slots configured to slide with rails of the outer tower body.

In Example 14, the subject matter of Example 13 optionally includes wherein the first and second inner slides include windows configured to engage with ramps of the first and second deflectable arms to push the first and second deflectable arms radially outward.

In Example 15, the subject matter of any one or more of Examples 13-14 optionally include wherein the first and second inner slides include features configured to engage with protrusions of the first and second deflectable prongs to push the first and second deflectable prongs radially outward.

Example 16 is a method of operating a tower extender in conjunction with a bone anchor housing, the method comprising: positioning a plurality of deflectable members of a distal end of the tower extender proximate the bone anchor housing; pushing the distal end of the tower extender into engagement with the bone anchor housing to flex the plurality of deflectable members around the bone anchor housing to attach the tower extender relative to the bone anchor housing; rotating a knob to lock the plurality of deflectable members from deflecting away from the bone anchor housing; performing a portion of a surgical procedure with the tower extender; rotating the knob to deflect the plurality of deflectable members away from the bone anchor housing; and puling the tower extender away from the bone anchor housing.

In Example 17, the subject matter of Example 16 optionally includes wherein pushing the distal end of the tower extender into engagement with the bone anchor housing to flex the plurality of deflectable members around the bone anchor housing to attach the tower extender relative to the bone anchor housing comprises: rotating the knob to a position wherein the plurality of deflectable members are freely deflectable.

In Example 18, the subject matter of any one or more of Examples 16-17 optionally include wherein pushing the distal end of the tower extender into engagement with the bone anchor housing to flex the plurality of deflectable members around the bone anchor housing to attach the tower extender relative to the bone anchor housing comprises: deflecting first and second pairs of deflectable members radially outward relative to an axis of the tower extender, wherein the first and second pairs of deflectable members are aligned orthogonally to each other.

In Example 19, the subject matter of any one or more of Examples 16-18 optionally include wherein rotating a knob to lock the plurality of deflectable members from deflecting away from the bone anchor housing comprises: pushing a slide along the tower extender to interlock with each of the plurality of deflectable members to prevent radially outward deflection.

In Example 20, the subject matter of any one or more of Examples 16-19 optionally include wherein rotating the knob to deflect the plurality of deflectable members away from the bone anchor housing comprises: Pushing a slide along the tower extender to push each of the plurality of deflectable members radially outward.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present invention also contemplates examples in which only those elements shown or described are provided. Moreover, the present invention also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An extender tower configured to couple to a bone anchor, the extender tower comprising:
   an outer tower body extending along a longitudinal axis from a proximal portion to a distal portion, the tower body comprising:
      first and second deflectable arms at the distal portion configured to engage with a housing of a bone anchor;
      first and second ramp-locks located on the first and second deflectable arms, respectively;
      a threaded portion located at the proximal portion;
      first and second deflectable prongs extending alongside the first deflectable arm; and
      third and fourth deflectable prongs extending alongside the second deflectable arm;
   a cap configured to engage the threaded portion;
   a first inner slide comprising a first coupling portion configured to engage the cap and a first window configured to engage the first ramp-lock; and
   a second inner slide comprising a second coupling portion configured to engage the cap and a second window configured to engage the second ramp-lock;
   wherein the cap can be rotated to:
      move the first and second inner slides to engage the first and second ramp-locks to push the first and second deflectable arms outward; and
      move the first and second inner slides to engage the first and second ramp-locks to prevent outward movement of the first and second deflectable arms.

2. The extender tower of claim 1, wherein the first and second deflectable arms and the first through fourth deflectable prongs include features for engaging the housing of the bone anchor.

3. The extender tower of claim 1, wherein:
   the first inner slide includes first and second actuation features to push the first and second deflectable prongs outward; and
   the second inner slide includes third and fourth actuation features to push the third and fourth deflectable prongs outward.

4. The extender tower of claim 3, wherein the first through fourth actuation features comprise pins configured to engage ramps of the first through fourth prongs.

5. The extender tower of claim 1, wherein:
   the first and second deflectable arms are configured to mate with closed faces of the bone anchor housing; and
   the first through fourth deflectable prongs are configured to mate with open faces of the bone anchor housing.

6. The extender tower of claim 1, wherein
   the tower body further comprises first and second rails extending axially alongside the first and second deflectable prongs; and
   the first inner slide comprises first and second slots configured to receive the first and second rails.

7. The extender tower of claim 6, wherein:
   the first and second rails comprise a plurality of intermittent rail segments; and
   the first and second slots comprises a plurality of intermittent slot segments.

8. The extender tower of claim 7, wherein the plurality of intermittent rail segments and the plurality of intermittent slot segments are configured to, when engaged, permit axial sliding and prevent radial and circumferential displacement.

9. An extender tower for a bone anchor, the extender tower comprising:
   an outer tower body extending along a longitudinal axis, the tower body comprising:
      first and second deflectable arms disposed in opposing arrangement in a first radial direction;
      first and second deflectable prongs disposed in opposing arrangement in a second radial direction;
   a slide arrangement configured to slide within the outer tower body to engage the first and second deflectable arms and the first and second deflectable prongs; and
   a cap connected to the slide arrangement and configured to move axially relative to the outer tower body to move the slide arrangement;
   wherein the slide arrangement is configured to engage the first and second deflectable arms and the first and second deflectable prongs in different axial positions including:
      a first axial position configured to radially interlock the slide arrangement with the first and second deflectable arms and the first and second deflectable prongs;
      a second axial position configured to allow the first and second deflectable arms and the first and second deflectable prongs to freely deflect; and
      a third axial position configured to push the first and second deflectable arms and the first and second deflectable prongs radially outward.

10. The extender tower of claim 9, wherein the first and second deflectable arms are configured to deflect in a plane disposed orthogonal to a plane in which the first and second deflectable prongs are configured to deflect.

11. The extender tower of claim 9, further comprising third and fourth deflectable prongs.

12. The extender tower of claim 9, wherein the slide arrangement comprises first and second inner slides having slots configured to slide with rails of the outer tower body.

13. The extender tower of claim 12, wherein the first and second inner slides include windows configured to engage with ramps of the first and second deflectable arms to push the first and second deflectable arms radially outward.

14. The extender tower of claim 12, wherein the first and second inner slides include features configured to engage with protrusions of the first and second deflectable prongs to push the first and second deflectable prongs radially outward.

15. An extender tower configured to couple to a bone anchor, the extender tower comprising:
   an outer tower body extending along a longitudinal axis from a proximal portion to a distal portion, the tower body comprising:
      first and second deflectable arms at the distal portion configured to engage with a housing of a bone anchor;
      first and second ramp-locks located on the first and second deflectable arms, respectively;
      a threaded portion located at the proximal portion;
      first and second deflectable prongs extending alongside the first deflectable arm; and
      third and fourth deflectable prongs extending alongside the second deflectable arm;
   a cap configured to engage the threaded portion, the cap having an annular body and one or more grip features disposed on the annular body;
   a first inner slide comprising a first coupling portion configured to engage the cap and a first window configured to engage the first ramp-lock, wherein the first inner slide includes first and second actuation features to push the first and second deflectable prongs outward; and a second inner slide comprising a second coupling portion configured to engage the cap and a second window configured to engage the second ramp-lock, wherein the second inner slide includes third and fourth actuation features to push the third and fourth deflectable prongs outward;

wherein the cap can be rotated to:
move the first and second inner slides to engage the first and second ramp-locks to push the first and second deflectable arms outward; and
move the first and second inner slides to engage the first and second ramp-locks to prevent outward movement of the first and second deflectable arms.

16. The extender tower of claim 15, wherein the first and second deflectable arms and the first through fourth deflectable prongs include features for engaging the housing of the bone anchor.

17. The extender tower of claim 15, wherein the first through fourth actuation features comprise pins configured to engage ramps of the first through fourth prongs.

18. The extender tower of claim 15, wherein:
the first and second deflectable arms are configured to mate with closed faces of the bone anchor housing; and
the first through fourth deflectable prongs are configured to mate with open faces of the bone anchor housing.

* * * * *